(12) United States Patent
Teranishi et al.

(10) Patent No.: US 10,350,310 B2
(45) Date of Patent: Jul. 16, 2019

(54) INDOCYANINE COMPOUND, SYNTHESIS METHOD AND PURIFICATION METHOD THEREOF, DIAGNOSTIC COMPOSITION USING THE INDOCYANINE COMPOUND, AND DEVICE FOR MEASURING BIOKINETICS AND DEVICE FOR VISUALIZING CIRCULATION USING THE DIAGNOSTIC COMPOSITION

(71) Applicants: NATIONAL UNIVERSITY CORPORATION MIE UNIVERSITY, Tsu-shi (JP); NATIONAL UNIVERSITY CORPORATION NAGOYA UNIVERSITY, Nagoya-shi (JP)

(72) Inventors: Katsunori Teranishi, Tsu (JP); Hitoshi Hirata, Nagoya (JP); Tetsuya Arai, Nagoya (JP)

(73) Assignees: NATIONAL UNIVERSITY CORPORATION MIE UNIVERSITY, Tsu-shi (JP); NATIONAL UNIVERSITY CORPORATION NAGOYA UNIVERSITY, Nagoya-shi (JP)

( * ) Notice: Subject to any disclaimer, the term of this patent is extended or adjusted under 35 U.S.C. 154(b) by 0 days.

(21) Appl. No.: 16/101,544

(22) Filed: Aug. 13, 2018

(65) Prior Publication Data
US 2018/0353626 A1 Dec. 13, 2018

Related U.S. Application Data

(60) Continuation of application No. 15/438,047, filed on Feb. 21, 2017, now Pat. No. 10,086,090, which is a
(Continued)

(30) Foreign Application Priority Data

Jan. 28, 2010 (JP) .................................. 2010-017255
Jun. 10, 2010 (JP) .................................. 2010-132923

(51) Int. Cl.
*A61B 5/00* (2006.01)
*A61B 8/00* (2006.01)
*A61B 10/00* (2006.01)
*A61K 49/00* (2006.01)
*C08B 37/16* (2006.01)
(Continued)

(52) U.S. Cl.
CPC ........ *A61K 49/0054* (2013.01); *A61B 5/0071* (2013.01); *A61B 5/0205* (2013.01); *A61B 5/026* (2013.01); *A61B 5/201* (2013.01); *A61B 5/415* (2013.01); *A61B 5/418* (2013.01); *A61B 5/7275* (2013.01); *A61B 5/7425* (2013.01); *A61K 49/0032* (2013.01); *A61K 49/0034* (2013.01); *A61K 49/0093* (2013.01); *A61M 5/007* (2013.01); *C08B 37/0012* (2013.01); *C08B 37/0015* (2013.01); *C09B 23/0066* (2013.01); *C09B 23/086* (2013.01); *C09B 68/485* (2013.01); *A61B 5/0275* (2013.01);
(Continued)

(58) Field of Classification Search
None
See application file for complete search history.

(56) References Cited

U.S. PATENT DOCUMENTS 5,877,310 A 3/1999 Reddington et al.
6,136,612 A 10/2000 Della Ciana et al.
(Continued)

FOREIGN PATENT DOCUMENTS

EP 0 876 428 11/1998
EP 977 766 2/2000
(Continued)

OTHER PUBLICATIONS

Written Opinion dated May 4, 2011 in Application No. PCT/JP2011/000489 (English Translation).
(Continued)

*Primary Examiner* — Michael G. Hartley
*Assistant Examiner* — Melissa J Perreira
(74) *Attorney, Agent, or Firm* — Oblon, McClelland, Maier & Neustadt, L.L.P.

(57) ABSTRACT

The present invention aims at providing a novel indocyanine compound solving problems of conventionally used indocyanine green, such as solubility in water or physiological saline, a synthesis method and a purification method thereof, and a diagnostic composition including the novel indocyanine compound. Further, provided are a method for evaluating biokinetics of the novel indocyanine compound and a device for measuring biokinetics, and a method and a device for visualizing circulation of fluid such as blood in a living body, which utilize the diagnostic composition. Also, found are a novel indocyanine compound in which a hydrophobic moiety in a near-infrared fluorescent indocyanine molecule is included in a cavity of a cyclic sugar chain cyclodextrin to cover the hydrophobic moiety in the indocyanine molecule with the glucose, and a synthesis method and a purification method thereof. Furthermore, found are a method for fluorescence-imaging an organ other than liver by intravenous administration, a method for evaluating biokinetics of the novel indocyanine compound, a device for measuring biokinetics, and a method and a device for visualizing circulation of fluid such as blood in a living body, utilizing the diagnostic composition including the novel indocyanine compound.

8 Claims, 16 Drawing Sheets

Related U.S. Application Data division of application No. 14/616,117, filed on Feb. 6, 2015, now Pat. No. 9,844,606, which is a continuation of application No. 13/575,810, filed as application No. PCT/JP2011/000489 on Jan. 28, 2011, now Pat. No. 9,056,131.

(51) Int. Cl.
```
C09B 23/01      (2006.01)
C09B 23/08      (2006.01)
A61B 5/0205     (2006.01)
A61B 5/026      (2006.01)
A61B 5/20       (2006.01)
A61M 5/00       (2006.01)
C09B 67/00      (2006.01)
A61B 5/0275     (2006.01)
```

(52) U.S. Cl.
CPC ......... *A61B 2576/00* (2013.01); *A61K 49/001* (2013.01); *A61K 49/0017* (2013.01); *C09B 68/41* (2013.01)

(56) References Cited

U.S. PATENT DOCUMENTS

| | | |
|---|---|---|
| 6,939,532 B2 | 9/2005 | Achilefu et al. |
| 7,488,468 B1 | 2/2009 | Miwa et al. |
| 8,343,463 B2 | 1/2013 | Dow et al. |
| 9,056,131 B2 | 6/2015 | Teranishi et al. |
| 9,844,606 B2 | 12/2017 | Teranishi et al. |
| 2004/0202611 A1 | 10/2004 | Achilefu et al. |
| 2005/0182321 A1 | 8/2005 | Frangioni et al. |
| 2007/0104649 A1 | 5/2007 | Fischer et al. |
| 2008/0154102 A1 | 6/2008 | Frangioni et al. |
| 2008/0312539 A1 | 12/2008 | Dorshow et al. |

FOREIGN PATENT DOCUMENTS

| | | |
|---|---|---|
| EP | 1 113 822 | 7/2001 |
| JP | 2000-95758 | 4/2000 |
| JP | 2001-524969 | 12/2001 |
| JP | 2002-531377 A | 9/2002 |
| JP | 2004-513893 A | 5/2004 |
| JP | 2011-173859 | 9/2011 |
| WO | WO 97/13810 | 4/1997 |
| WO | WO 98/49176 | 11/1998 |
| WO | WO 00/16810 | 3/2000 |
| WO | WO 2007/025768 A1 | 3/2007 |
| WO | WO 2008/016139 A1 | 2/2008 |

OTHER PUBLICATIONS

Mitsuo Kusano, et al., "All About Indocyanine Green (ICG) Fluorescence Navigation Surgery Chasing Flouorescing Lymph Nodes, Vessels, and Organs", Inter Media Co., 2008, 10 pages.
"Diagnogreen Chusha-yo 25 mg" Tenpu Bunsho, 2008, pp. 1-4 (English Translation).
R. C. Benson, et al., "Fluorescence Properties of Indocyanine Green as Related to Angiography", Phys. Med. Biol., vol. 23, No. 1, 1978, pp. 159-163.
Shin Yoneya, et al., "Binding Properties of Indocyanine Green in Human Blood", IOVS, vol. 39, No. 7, 1998, pp. 1286-1290.
Yunpeng YE, et al., "Synthesis and Characterization of a Macrocyclic Near-Infrared Optical Scaffold", J. Am. Chem. Soc., vol. 125, 2003, pp. 7766-7767.
Katsunori Teranishi, et al., "Regiospecific Alkylation Dependent on Alkyl Chain Length of N-Bromoalkylphthalimides and the Efficient Preparation of 2-O-Aminoalkyl Cyclomaltooligosaccharides (Cyclodextrins)", ITE Letters on Batteries, New Technologies and Medicine, 1, 2000, pp. 53-60.
Michael O'Shaughnessy, et al., "Microcirculatory Consequences of Microvascular Surgery", Microsurgery,1994, 15, pp. 405-412.
Ralph J.P.M Franken, et al., "Anatomy of the Feeding Blood Vessels of the Cremaster Muscle in the Rat", Microsurgery, 1996, 17, pp. 402-408.
B. Riefke, et al., "In vivo characterization of cyanine dyes as contrast aents for near-infrared imaging", SPIE, vol. 2927, 1996, pp. 199-208.
Igor L. Medintz, et al., "Self-assembled nanoscale biosensors based on quantum dot FRET donors", Nature Materials, vol. 2, No. 9, 2003, pp. 630-638.
Igor L. Medintz, et al., "A Fluorescence Resonance Energy Transfer Sensor Based on Maltose Binding Protein", Bioconjugate Chemistry, vol. 14, 2003, pp. 909-918.
Katsunori Teranishi, "Chemical effects by cyclodextrin-conjugation on near-infrared fluorescent compound, indocyanine green molecule", Cyclodextrin Symposium Koen Yoshishu, Sep. 6, 2010, pp. 140-141 (English Summary).
Christin Perlitz, et al., "Comparison of Two Tricarbocyanine-Based Dyes for Fluorescence Optical Imaging", Journal of Fluorescence, vol. 15, No. 3, May 2005, DOI: 10.1007/s10895-005-2636-x, pp. 443-454.
Akira Nakayama, et al., Functional Near-Infrared Fluorescence Imaging for Cardiac Surgery and Targeted Gene Therapy, Molecular Imaging, vol. 1, No. 4, Oct. 2002, pp. 365-377.
Eiichi Tanaka, et al., Real-Time Intraoperative Ureteral Guidance Using Invisible Near-Infrared Fluorescence, The Journal of Urology, vol. 178, 2197-2202, Nov. 2007.
Office Action dated Jun. 2, 2016 in Chinese Patent Application No. 201180006735.X (with English language translation).
Extended European Search Report dated Jun. 6, 2016 in Patent Application No. 11736813.4.
Suresh I. Prajapati, et al., "Crimson carrier, A long-acting contrast agent for in vivo near-infrared imaging of injured and diseased muscle", Muscle & Nerve, vol. 42, No. 2, XP055274925, 2010, pp. 245-251.
Teresa C. Barros, et al., "Polymethine cyanine dyes in β-cyclodextrin solution: multiple equilibria and chemical oxidation", Journal of Physical Organic Chemistry, vol. 23, No. 10, XP055139106, Mar. 26, 2010, pp. 893-903.
Chinese Examination Decision with letter from Chinese representative dated Nov. 28, 2016 in patent application No. 201180006735.X with English translation.
English translation of International Preliminary Report on Patentability (Chapter II) issued in PCT/JP2011/000489, dated Nov. 1, 2012, 6 pp.
Office Action dated Aug. 29, 2014 in corresponding Chinese Patent Application No. 201180006735.X with English translation, 13 pp.
Decision of Rejection dated Feb. 3, 2015 in Chinese Patent Application No. 201180006735.X (with English language translation).
Office Action dated Jan. 4, 2019, in corresponding Chinese Patent Application No. 201710146571.X (with machine English-language Translation).

ICG                chem.20

ICG                chem.20

INDOCYANINE COMPOUND, SYNTHESIS METHOD AND PURIFICATION METHOD THEREOF, DIAGNOSTIC COMPOSITION USING THE INDOCYANINE COMPOUND, AND DEVICE FOR MEASURING BIOKINETICS AND DEVICE FOR VISUALIZING CIRCULATION USING THE DIAGNOSTIC COMPOSITION

CROSS REFERENCES TO RELATED APPLICATIONS

This application is a continuation of U.S. patent application Ser. No. 15/438,047, filed Feb. 21, 2017, now allowed, which is a divisional of U.S. patent application Ser. No. 14/616,117, filed Feb. 6, 2015, now U.S. Pat. No. 9,844,606; which is a continuation of U.S. patent application Ser. No. 13/575,810, filed Jul. 27, 2012, now U.S. Pat. No. 9,056,131; which is the National Stage of the International Patent Application No. PCT/JP2011/000489, filed Jan. 28, 2011, the disclosures of which are incorporated herein by reference in their entireties. This application claims priority to Japanese Patent Application No. 2010-017255, filed Jan. 28, 2010; and Japanese Patent Application No. 2010-132923, filed Jun. 10, 2010, the disclosures of which are incorporated herein by reference in their entireties.

TECHNICAL FIELD

The present invention relates to a novel indocyanine compound which is a green pigment useful for medical diagnostic technologies, medical surgical technologies, scientific measurement and analysis technologies, printing technologies, writing technologies, coating technologies, dyestuffs technologies and dyeing technologies, and has a property capable of emitting near-infrared fluorescence, a synthesis method and a purification method thereof, and a diagnostic composition. More particularly, the present invention relates to a cyclic sugar chain cyclodextrin-bonded indocyanine compound which is a green pigment and has a property capable of emitting near-infrared fluorescence, a synthesis method and a purification method thereof, and a diagnostic composition using the indocyanine compound, a device for measuring biokinetics and a device for visualizing a circulation using the diagnostic composition.

BACKGROUND ART

Indocyanine compounds which are green pigments and emit near-infrared fluorescence have hitherto been synthesized, and they have various applications such as pigments for dyeing used in surgeries of vitreous body of the eye, pigments used in medicines for testing liver functions, pigment used in medicines for testing circulatory functions, pigments used for surgical operations, and near-infrared fluorescent compounds used for surgical operation in medical fields; dyeing of proteins or sugars and compounds for fluoresceination in scientific fields; and pigments in printing technologies. Of these indocyanine compounds, a compound which is called as an indocyanine green (hereinafter referred to as "ICG") has been used as a medicine for testing liver functions or circulatory functions for nearly 50 years. ICG has recently been used for medical operations or medical diagnoses, utilizing its property of high light-permeability from a biological tissue, by topically administrating ICG to a body such as a blood vessel, lymph vessel, brain, eye, stomach, breast, esophagus, skin or another site and observing the near-infrared fluorescence of ICG, which is a trial run yet though, as the application of ICG other than the medicines for testing liver functions or circulatory function (Non Patent Document 1).

PRIOR ART TECHNICAL DOCUMENTS

Non Patent Document

Non Patent Document 1: "All of ICG fluorescence Navigation Surgery", supervised and edited by Mitsuo Kusano, Intermedica Co., Ltd, (published on November, 2008).
Non Patent Document 2: URL (https://www.daiichisankyo-.co.jp/med/contents/di/dg2/pi/pdf/pi_dg2_0909.pdf) of Internet Homepage in which an attached document to "(trademark) Diagnogreen for injection 25 mg" (Daiichi Sankyo Company, Limited) is provided.
Non Patent Document 3: R. C. Benson, H. A. Kues, Phys. Med. Biol., 23, 159-163 (1978).
Non Patent Document 4: S. Yoneyama, T. Saito, Y. Komatsu, I. Koyama, K. Takahashi, J. Duvoll-Young, IOVS, 37, 1286-1290 (1998).
Non Patent Document 5: Y. Ye, W. P. Li, C. J. Anderson, J. Kao, G. V. Nikiforovich, S. Achilefu, J. Am. Chem. Soc., 125, 7766-7767 (2003).
Non Patent Document 6: K. Teranishi and S. Tanabe, ITE Letters on Batteries, New Technologies & Medicine, 1, 53-60 (2000).
Non Patent Document 7: MICHAEL O'SHAUGHNESSY et al: 1994 Wiley-Liss, Inc MICROSURGERY 15: 40 S 412 1994.
Non Patent Document 8: RALPH J. P. M et al: 1997 Wiley-Liss, Inc. MICROSURGERY 17: 402-408 1996.

SUMMARY OF THE INVENTION

Problems to be Solved by the Invention

A green chromophore (a chemical structure necessary for exhibiting green) and a near-infrared fluorophore (a chemical structure necessary for exhibiting near-infrared fluorescence) of ICG, however, are hydrophobic, and thus sulfonyl groups are bonded to the side-chain terminus to render them water-soluble. This gives many problems described below to the conventional ICG.

When ICG preparation is used in medical applications, distilled water is generally added to 25 mg of ICG in an amount of about 5 mL to 10 mL, and the ICG is dissolved by vibration agitation. If the ICG is not completely dissolved, vomiturition, nausea, fever or a shock-like symptom may sometimes occur (Non Patent Document 2). Additionally, it is impossible to initially dissolve it in another aqueous solution such as physiological saline because of insolubilization (Non Patent Document 2).

ICG is water-soluble because sulfonyl groups are bonded thereto, as described above, but it has a surface activity because of its chemical structure in which there are many hydrophobic hydrocarbon groups, and thus it has a property of adsorbing to lipids. When it is administered to a biological tissue such as a blood vessel or an organ, accordingly, it adheres to the injected site, it is leaked by mistake or it is flown backward, whereby it may sometimes adhere to an undesired biological tissue. ICG adhering to the biological tissue cannot be easily removed from the biological tissue by wiping it away or sucking it, leading to a possibility in which a surgical operation or a medical diagnosis is interfered.

ICG has a property of assembling molecules in an aqueous solution. ICG, thus, has a low fluorescence intensity in an aqueous solution, though the property is one of primary factors (Non Patent Documents 3 and 4).

In addition, ICG becomes insolubilized as time advances after it is dissolved in water, and thus it is difficult to store it in the state of an aqueous solution for a long term. In addition, at a low temperature, freeze preservation thereof promotes the insolubilization.

ICG preparation includes 5% or less NaI, and has a defect in which it may cause iodine hypersensitivity (Non Patent Document 2).

When ICG is intravenously injected, it is promptly accumulated in a liver and excreted through the liver, and accordingly, fluorescence imaging of another organ such as a kidney, ureter, bladder, urethra, heart or lung is difficult.

In addition, when ICG is intravenously injected, it transfers with blood and it transfers a little to peripheral tissues, and accordingly it is difficult to observe the transfer to an interstitial tissue.

The present invention aims at solving the problems of the conventional ICG described above, in other words, the present invention aims at providing a novel indocyanine compound which is a green pigment and exhibits near-infrared fluorescence, characterized by a high solubility in water or physiological saline, easy removal from a biological tissue, a low molecule association in an aqueous solution, a high near-infrared fluorescence intensity in an aqueous solution, and fluorescence imaging of an organ other than liver such as kidney, ureter, bladder, urethra, heart or lung. The present invention further provides a chemical synthesis method and a purification method of the novel indocyanine compound having the features described above. To provide a diagnostic composition including the novel indocyanine compound is also a problem to be solved by the invention. Furthermore, the present invention aims at providing a device for measuring biokinetics capable of evaluating biokinetics of the novel indocyanine compound, concerning a horizontal equilibrium in a living body, and a method and device for visualizing a circulation of blood, lymph fluid, urine or other fluid in a living body, utilizing the diagnostic composition.

Means of Solving the Problem

The present inventors have repeated painstaking studies in order to solve the problems described above; as a result, they have found a compound exhibiting near-infrared fluorescence, which can be used in a surgical operation or medical diagnosis utilizing the property of exhibiting near-infrared fluorescence, and have solved the problems of ICG described above.

The present inventors have found a novel indocyanine compound which is a green pigment characterized by a high solubility in water or physiological saline, easy removal from a biological tissue, a low molecule association in an aqueous solution, a high near-infrared fluorescence intensity in an aqueous solution, and exhibition of near-infrared fluorescence; and have completed the present invention. Further, they have found a chemical synthesis method and a purification method of the novel indocyanine compound, and have completed the present invention. Furthermore, they have provided a diagnostic composition including the novel indocyanine compound. Still further, they have provided a method for fluorescence imaging an organ other than liver even in intravenous administration by utilizing the diagnostic composition. Still further, they have provided a method for evaluating biokinetics of the novel indocyanine compound, concerning a horizontal equilibrium in a living body and a device for measuring biokinetics, and a method and a device for visualizing circulation of blood, lymph fluid, urine or other fluid in a living body.

A first novel indocyanine compound of the present invention is a compound in which a cyclic sugar chain cyclodextrin is covalently bonded to a green chromophore (a chemical structure necessary for exhibiting green) and a near-infrared fluorophore (a chemical structure necessary for exhibiting near-infrared fluorescence) of ICG. Further, a second novel indocyanine compound of the invention is a novel indocyanine compound which is characterized in that a naphthyl moiety which is a hydrophobic moiety of an indocyanine structure is included in a cavity of a cyclodextrin to cover a naphthyl moiety which is a hydrophobic moiety with a hydrophilic glucose group, thereby three-dimensionally hydrophilizing many regions of the indocyanine molecule structure. ICG is characterized by having a surfactant-like property in which it has both hydrophobic moieties and hydrophilic property caused by sulfonyl groups; whereas, the compound of the invention is characterized by having no surfactant-like property because the hydrophobic moieties in its molecule is covered with the cyclodextrins. In more detail, the present inventions are:

<1> A cyclodextrin-bonded indocyanine compound in which an indocyanine is covalently bonded to a cyclic sugar chain cyclodextrin, which is represented by the following chemical formula 1:

[Chem. 1]

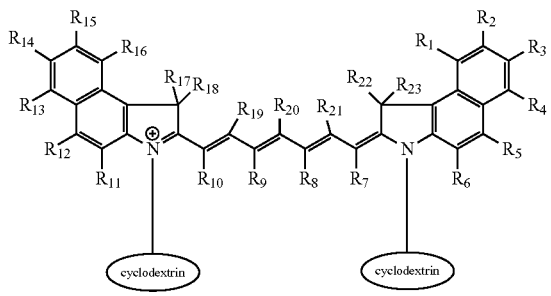

(1)

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$ and $R_{23}$ are a hydrogen atom, an alkyl group, an aryl group, a halogen atom, an alkoxyl group, an amino group, a carboxyl group, a formyl group, a sulfonyl group, a sulfonic acid group, a phosphate group, an alkyloxycarbonyl group, an aryloxycarbonyl group, an alkylcarbonyl group, an arylcarbonyl group, or a heterocyclic ring; when a hydrogen ion on the substituents (the carboxylic acid, the sulfonic acid and the phosphoric acid) dissociates, a metal ion such as a sodium ion, a potassium ion, a magnesium ion or a calcium ion may be substituted for the hydrogen ion; the amino group is also selected from primary, secondary, tertiary and quaternary groups (a substituent bonded to the nitrogen atom includes an alkyl group, and the like); a cyclic structure of $CH_2$, $CH_2CH_2$, $CH_2CH_2CH_2$ or $CH_2CH_2CH_2CH_2$ is selected as the groups $R_8$ and $R_9$; and a functional group of an alkyl group, an aryl group, a halogen atom, an alkoxy group, an amino group, a carboxyl group, a formyl group, a sulfonyl group, a sulfonic acid group, a phosphate group, an alkyloxycarbonyl group, an aryloxycarbonyl group, an alkylcarbonyl group, an arylcarbonyl group or a heterocyclic ring is also substituted for the hydrogen atom on the alkyl groups.

<2> A cyclodextrin-bonded indocyanine compound in which at least a part of a naphthyl group of an indocyanine is included in a cavity of a cyclodextrin, represented by the following chemical formula 2:

[Chem. 2]

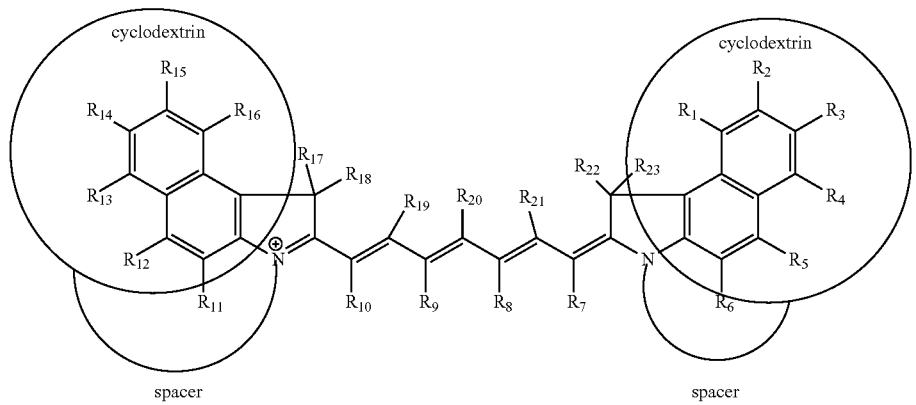

(2)

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$ and $R_{23}$ are a hydrogen atom, an alkyl group, an aryl group, a halogen atom, an alkoxyl group, an amino group, a carboxyl group, a formyl group, a sulfonyl group, a sulfonic acid group, a phosphate group, an alkyloxycarbonyl group, an aryloxycarbonyl group, an alkylcarbonyl group, an arylcarbonyl group, or a heterocyclic ring; when a hydrogen ion on the substituents (the carboxylic acid, the sulfonic acid and the phosphoric acid) dissociates, a metal ion such as a sodium ion, a potassium ion, a magnesium ion or a calcium ion may be substituted for the hydrogen ion; the amino group is also selected from primary, secondary, tertiary and quaternary groups; a cyclic structure of $CH_2$, $CH_2CH_2$, $CH_2CH_2CH_2$ or $CH_2CH_2CH_2CH_2$ is also selected as the groups $R_8$ and $R_9$; and a functional group of an alkyl group, an aryl group, a halogen atom, an alkoxy group, an amino group, a carboxyl group, a formyl group, a sulfonyl group, a sulfonic acid group, a phosphate group, an alkyloxycarbonyl group, an aryloxycarbonyl group, an alkylcarbonyl group, an arylcarbonyl group or a heterocyclic ring is also substituted for the hydrogen atom on the alkyl groups.

<3> The cyclodextrin-bonded indocyanine compound in which an indocyanine is covalently bonded through an amide bond to a cyclic sugar chain cyclodextrin, represented by the chemical formula 1, wherein the compound is a cyclodextrin-bonded indocyanine compound represented by the following chemical formula 3:

[Chem. 3]

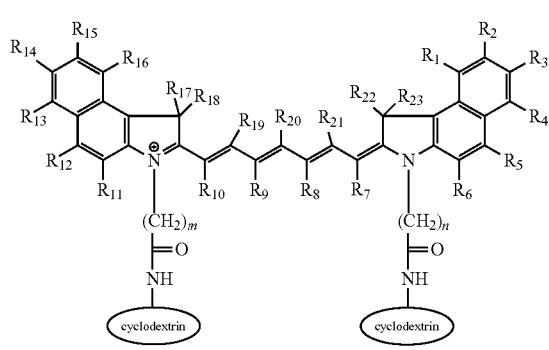

(3)

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$ and $R_{23}$ are a hydrogen atom, an alkyl group, an aryl group, a halogen atom, an alkoxyl group, an amino group, a carboxyl group, a formyl group, a sulfonyl group, a sulfonic acid group, a phosphate group, an alkyloxycarbonyl group, an aryloxycarbonyl group, an alkylcarbonyl group, an arylcarbonyl group, or a heterocyclic ring; when a hydrogen ion on the substituents (the carboxylic acid, the sulfonic acid and the phosphoric acid) dissociates, a metal ion such as a sodium ion, a potassium ion, a magnesium ion or a calcium ion may be substituted for the hydrogen ion; the amino group is also selected from primary, secondary, tertiary and quaternary groups; m and n are an integer of 1 or more and 6 or less; a cyclic structure of $CH_2$, $CH_2CH_2$, $CH_2CH_2CH_2$ or $CH_2CH_2CH_2CH_2$ is also selected as the groups $R_8$ and $R_9$; and a functional group of an alkyl group, an aryl group, a halogen atom, an alkoxy group, an amino group, a carboxyl group, a formyl group, a sulfonyl group, a sulfonic acid group, a phosphate group, an alkyloxycarbonyl group, an aryloxycarbonyl group, an alkylcarbonyl group, an arylcarbonyl group or a heterocyclic ring is also substituted for the hydrogen atom on the alkyl groups.

<4> The cyclodextrin-bonded indocyanine compound in which an indocyanine is covalently bonded through an amide bond to a cyclic sugar chain cyclodextrin, represented by the chemical formula 2, wherein the compound is a cyclodextrin-bonded indocyanine compound represented by the following chemical formula 4:

[Chem. 4]

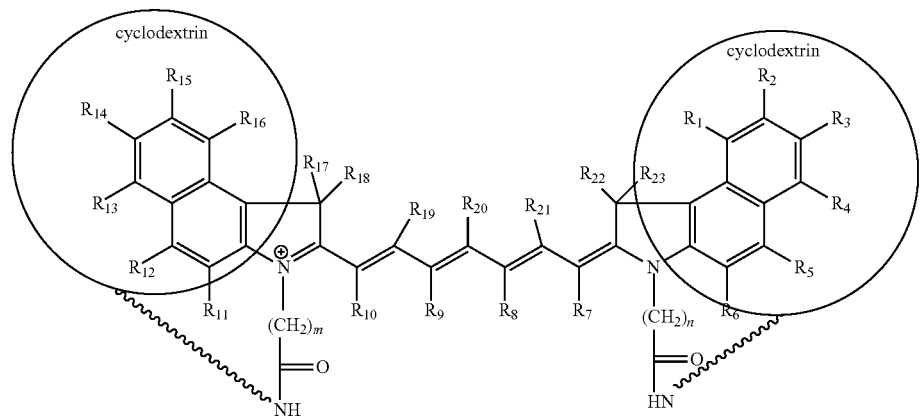

(4)

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$ and $R_{23}$ are a hydrogen atom, an alkyl group, an aryl group, a halogen atom, an alkoxyl group, an amino group, a carboxyl group, a formyl group, a sulfonyl group, a sulfonic acid group, a phosphate group, an alkyloxycarbonyl group, an aryloxycarbonyl group, an alkylcarbonyl group, an arylcarbonyl group, or a heterocyclic ring; when a hydrogen ion on the substituents (the carboxylic acid, the sulfonic acid and the phosphoric acid) dissociates, a metal ion such as a sodium ion, a potassium ion, a magnesium ion or a calcium ion may be substituted for the hydrogen ion; the amino group is also selected from primary, secondary, tertiary and quaternary groups; m and n are an integer of 1 or more and 6 or less; a cyclic structure of $CH_2$, $CH_2CH_2$, $CH_2CH_2CH_2$ or $CH_2CH_2CH_2CH_2$ is also selected as the groups $R_8$ and $R_9$; and a functional group of an alkyl group, an aryl group, a halogen atom, an alkoxy group, an amino group, a carboxyl group, a formyl group, a sulfonyl group, a sulfonic acid group, a phosphate group, an alkyloxycarbonyl group, an aryloxycarbonyl group, an alkylcarbonyl group, an arylcarbonyl group or a heterocyclic ring is also substituted for the hydrogen atom on the alkyl groups.

<5> The cyclodextrin-bonded indocyanine compound represented by the chemical formula 3, which is a cyclodextrin-bonded indocyanine compound represented by the following chemical formula 5:

[Chem. 5]

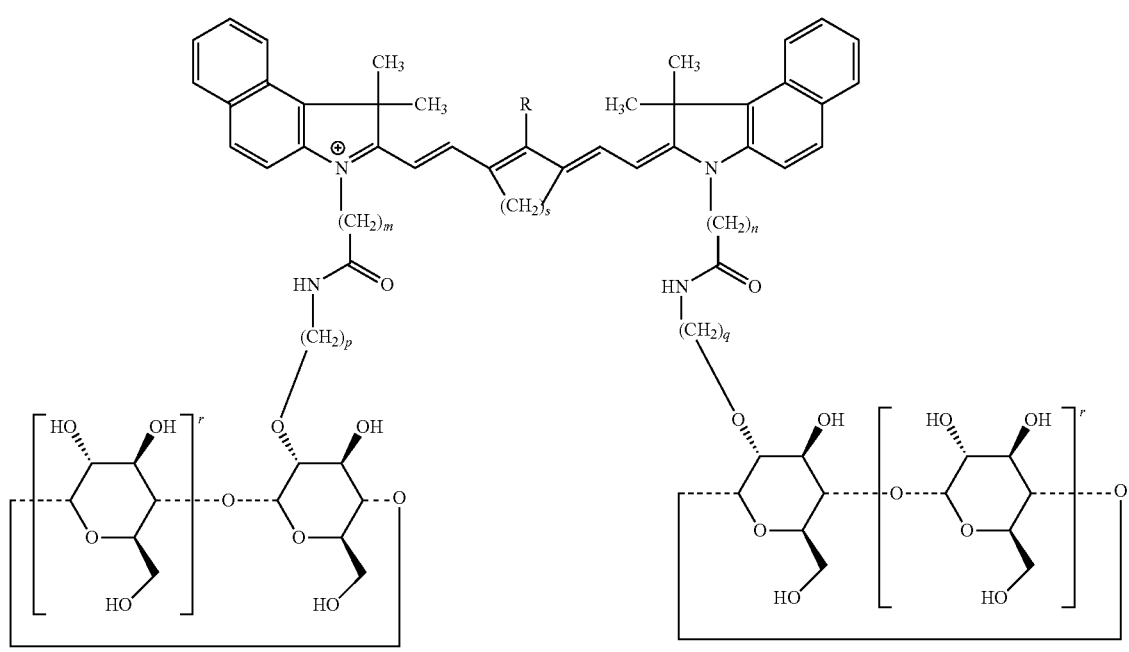

(5)

wherein m, n, p and q are an integer of 2 or more and 6 or less; r is an integer of 5 or more and 7 or less; s is an integer of 0 or more and 4 or less; and R is a hydrogen atom, an alkyl group, an aryl group, a halogen atom, an alkoxy group, an amino group, a carboxyl group, a formyl group, a sulfonyl group, a sulfonic acid group, an alkyloxycarbonyl group, an aryloxycarbonyl group, an alkylcarbonyl group, an arylcarbonyl group or a heterocyclic ring.

<6> The cyclodextrin-bonded indocyanine compound represented by the chemical formula 4, which is a cyclodextrin-bonded indocyanine compound represented by the following chemical formula 6:

[Chem. 6]

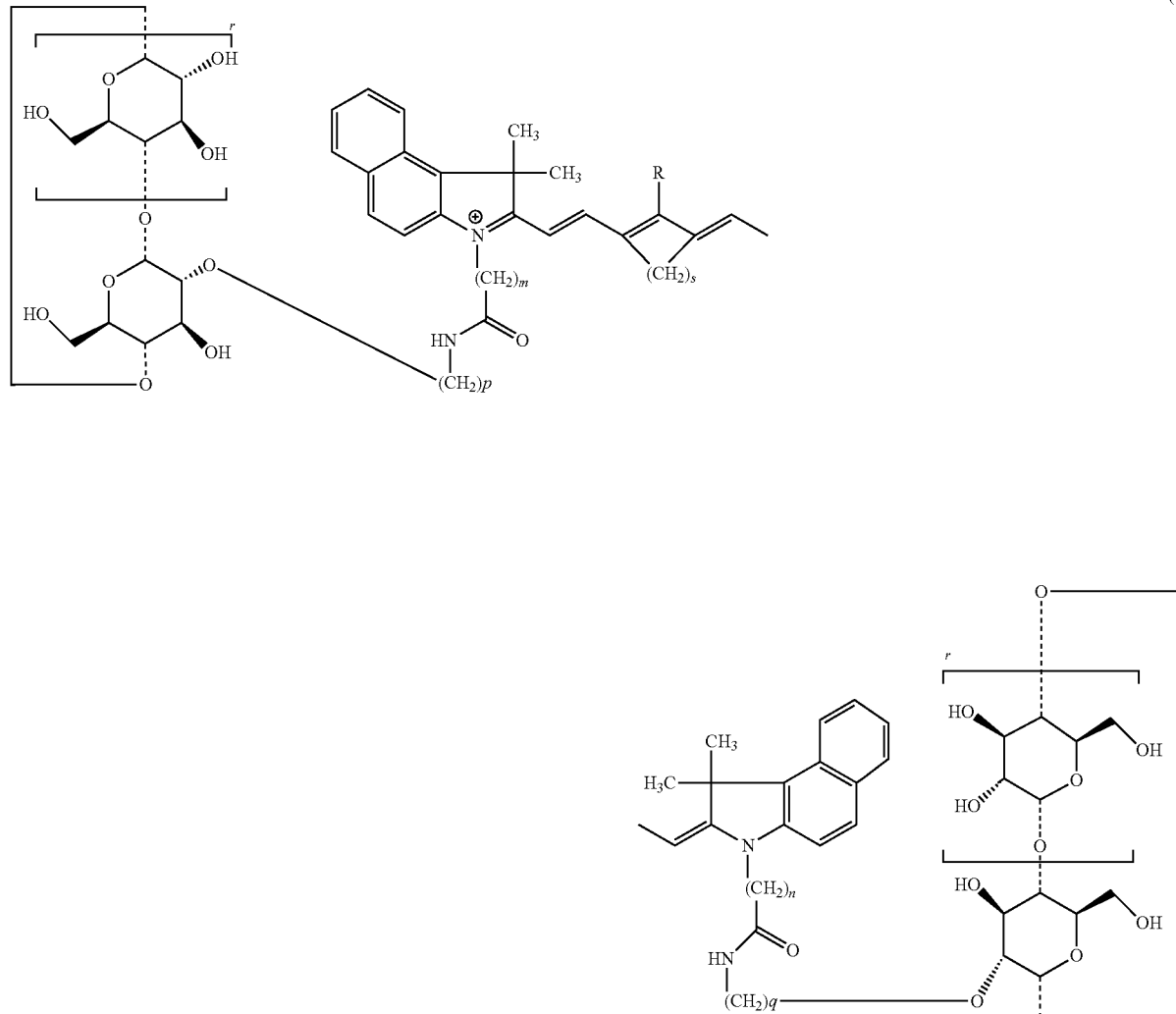

(6)

wherein m, n, p and q are an integer of 2 or more and 6 or less; r is an integer of 5 or more and 7 or less; s is an integer of 0 or more and 4 or less; and R is a hydrogen atom, an alkyl group, an aryl group, a halogen atom, an alkoxy group, an amino group, a carboxyl group, a formyl group, a sulfonyl group, a sulfonic acid group, an alkyloxycarbonyl group, an aryloxycarbonyl group, an alkylcarbonyl group, an arylcarbonyl group or a heterocyclic ring.

<7> The cyclodextrin-bonded indocyanine compound represented by the chemical formula 3, which is a cyclodextrin-bonded indocyanine compound represented by the following chemical formula 7:

[Chem. 7]

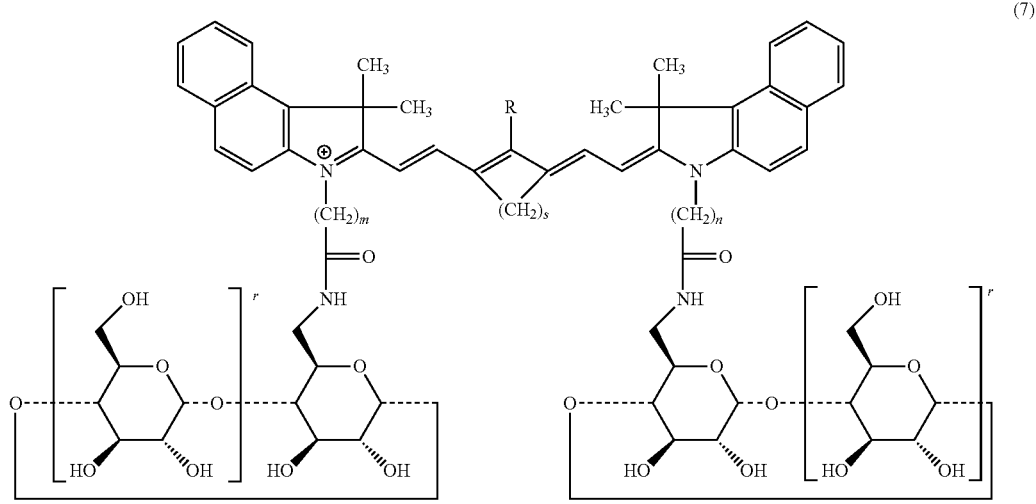

(7)

wherein m and n are an integer of 2 or more and 6 or less; r is an integer of 5 or more and 7 or less; s is an integer of 0 or more and 4 or less; and R is a hydrogen atom, an alkyl group, an aryl group, a halogen atom, an alkoxy group, an amino group, a carboxyl group, a formyl group, a sulfonyl group, a sulfonic acid group, an alkyloxycarbonyl group, an aryloxycarbonyl group, an alkylcarbonyl group, an arylcarbonyl group or a heterocyclic ring.

<8> The cyclodextrin-bonded indocyanine compound represented by the chemical formula 4 which is a cyclodextrin-bonded indocyanine compound represented by the following chemical formula 8:

[Chem. 8]

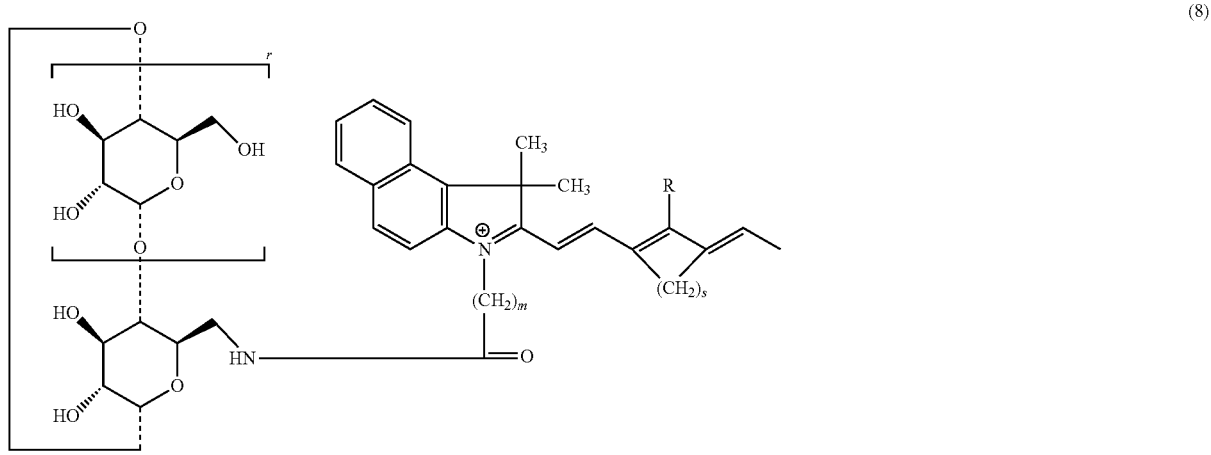

(8)

-continued

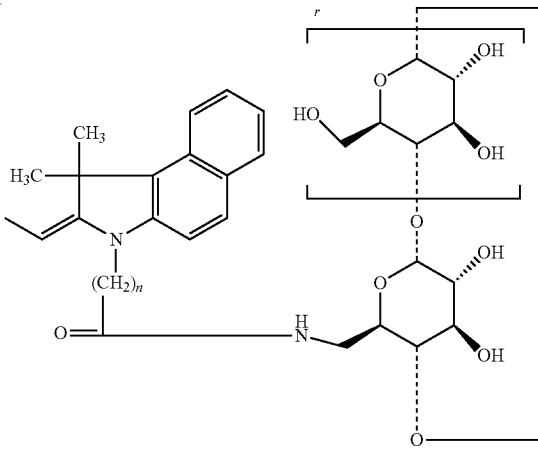

(20)

wherein m and n are an integer of 2 or more and 6 or less; r is an integer of 5 or more and 7 or less; s is an integer of 0 or more and 4 or less; and R is a hydrogen atom, an alkyl group, an aryl group, a halogen atom, an alkoxy group, an amino group, a carboxyl group, a formyl group, a sulfonyl group, a sulfonic acid group, an alkyloxycarbonyl group, an aryloxycarbonyl group, an alkylcarbonyl group, an arylcarbonyl group or a heterocyclic ring.

<9> The cyclodextrin-bonded indocyanine compound represented by the chemical formula 3, which is a cyclodextrin-bonded indocyanine compound represented by the following chemical formula 9:

[Chem. 9]

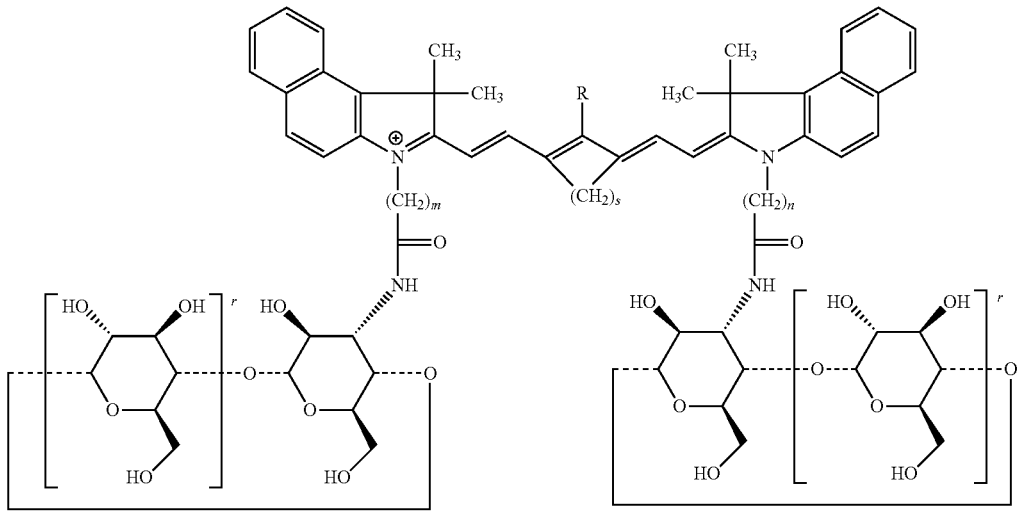

(9)

wherein m and n are an integer of 2 or more and 6 or less; r is an integer of 5 or more and 7 or less; s is an integer of 0 or more and 4 or less; and R is a hydrogen atom, an alkyl group, an aryl group, a halogen atom, an alkoxy group, an amino group, a carboxyl group, a formyl group, a sulfonyl group, a sulfonic acid group, an alkyloxycarbonyl group, an aryloxycarbonyl group, an alkylcarbonyl group, an arylcarbonyl group or a heterocyclic ring.

<10> The cyclodextrin-bonded indocyanine compound represented by the chemical formula 4, which is a cyclodextrin-bonded indocyanine compound represented by the following chemical formula 10:

[Chem. 10]

(10)

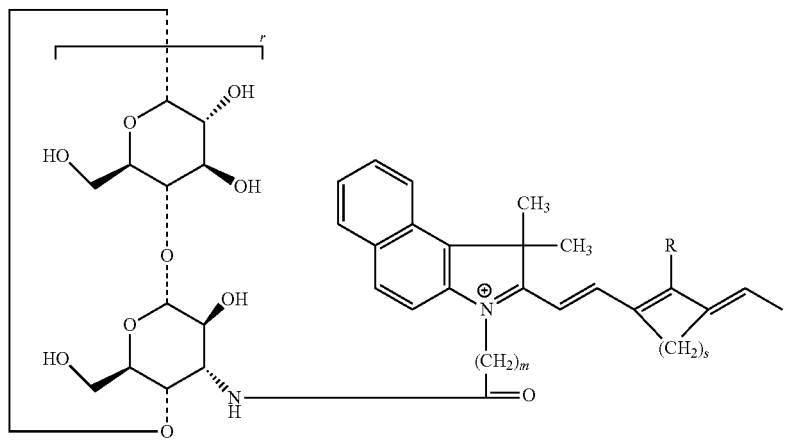

wherein m and n are an integer of 2 or more and 6 or less; r is an integer of 5 or more and 7 or less; s is an integer of 0 or more and 4 or less; and R is a hydrogen atom, an alkyl group, an aryl group, a halogen atom, an alkoxy group, an amino group, a carboxyl group, a formyl group, a sulfonyl group, a sulfonic acid group, an alkyloxycarbonyl group, an aryloxycarbonyl group, an alkylcarbonyl group, an arylcarbonyl group or a heterocyclic ring.

<11> The cyclodextrin-bonded indocyanine compound represented by the chemical formula 3, which is a cyclodextrin-bonded indocyanine compound represented by the following chemical formula 11:

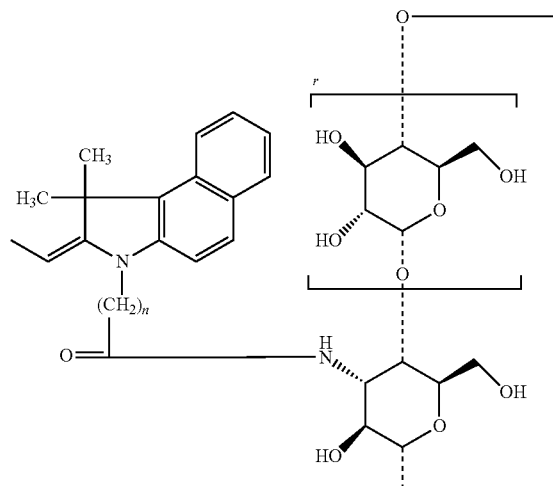

[Chem. 11]

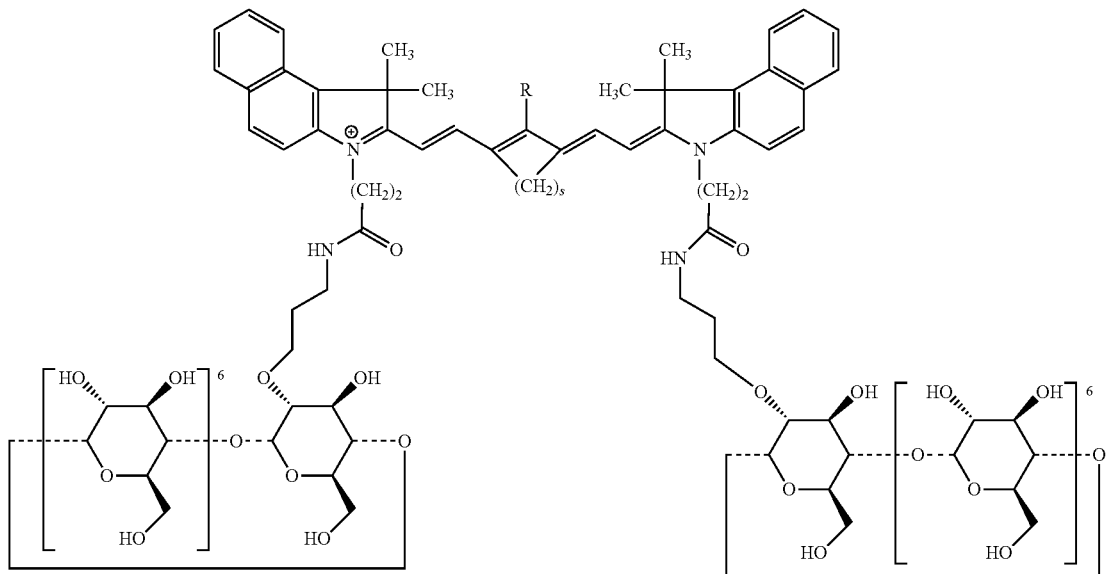

(11)

wherein s is an integer of 0 or more and 4 or less; and R is a hydrogen atom, an alkyl group, an aryl group, a halogen atom, an alkoxy group, an amino group, a carboxyl group, a formyl group, a sulfonyl group, a sulfonic acid group, an alkyloxycarbonyl group, an aryloxycarbonyl group, an alkylcarbonyl group, an arylcarbonyl group or a heterocyclic ring.

<12> The cyclodextrin-bonded indocyanine compound represented by the chemical formula 4, which is a cyclodextrin-bonded indocyanine compound represented by the following chemical formula 12:

<13> A chemical synthesis method of the cyclodextrin-bonded indocyanine compound represented by any one of the chemical formulae described above (chemical formulae 1, 3, 5, 7, 9 and 11), including: (1) a step of mixing an indocyaninecarboxylic acid compound with an aminocyclodextrin in a medium, and (2) a step of a dehydration-condensation reaction of the mixture by addition of a dehydration-condensing agent thereto.

[Chem. 12]

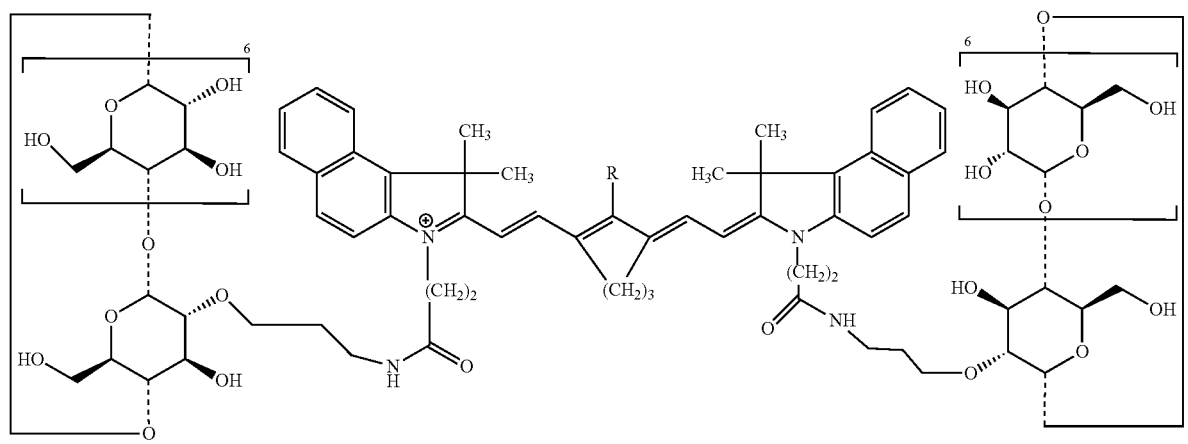

(12)

wherein s is an integer of 0 or more and 4 or less; and R is a hydrogen atom, an alkyl group, an aryl group, a halogen atom, an alkoxy group, an amino group, a carboxyl group, a formyl group, a sulfonyl group, a sulfonic acid group, an alkyloxycarbonyl group, an aryloxycarbonyl group, an alky- <14> A chemical synthesis method of the cyclodextrin-bonded indocyanine compound represented by any one of the chemical formulae described above (chemical formulae 2, 4, 6, 8, 10 and 12), including a step of subjecting the cyclodextrin-bonded indocyanine compound represented by any one of the chemical formulae described above (chemical formulae 1, 3, 5, 7, 9 and 11) to an inclusion reaction in water.

<15> A purification method of the cyclodextrin-bonded indocyanine compound represented by any one of the chemical formulae described above (chemical formulae 1 to 12), including a step of purifying the compound by a column chromatography eluting it with a medium including HCl.

<16> A diagnostic composition which is an aqueous solution including the cyclodextrin-bonded indocyanine compound represented by any one of the chemical formulae 1 to 12, and is used by infusing it into a body.

<17> The diagnostic composition according to the item <16>, which does not substantially include iodine.

<18> A device for measuring biokinetics of a cyclodextrin-bonded indocyanine compound including:
excitation light-irradiating means of irradiating excitation light to the cyclodextrin-bonded indocyanine compound in apart of a living body to which the diagnostic composition according to item <16> or <17> is administered;
fluorescence intensity-measuring means of measuring an intensity of fluorescence emitted by the cyclodextrin-bonded indocyanine compound which has been excited by the excitation light-irradiating means; and
biokinetics-calculating means of calculating a transfer speed of the cyclodextrin-bonded indocyanine compound in the part of the living body into and/or out of interstitial tissue fluid by obtaining a change with time in the fluorescence intensity from the fluorescence intensities acquired by the fluorescence intensity-measuring means with time.

<19> A device for visualizing circulation including: excitation light-irradiating means of irradiating excitation light to a cyclodextrin-bonded indocyanine compound in a part of a living body to which the diagnostic composition according to item <16> or <17> is administered;
fluorescence-imaging means of obtaining distribution state data of the cyclodextrin-bonded indocyanine compound in the living body by two-dimensionally acquiring a fluorescence intensity emitted by the cyclodextrin-bonded indocyanine compound which has been excited by the excitation light-irradiating means;
morphological imaging means of obtaining morphological data of the part of the living body by two-dimensionally acquiring an intensity of light having a wavelength other than the fluorescence wavelength emitted by the cyclodextrin-bonded indocyanine compound; and
displaying means of displaying a distribution state of the cyclodextrin-bonded indocyanine compound in the part of the living body by overlapping the morphological data obtained by the morphological imaging means with the distribution state data obtained by the fluorescence-imaging means.

<20> The device for visualizing circulation according to item <19>9, wherein the displaying means displays an area in which a distribution quantity of the cyclodextrin-bonded indocyanine compound is lower than a predetermined standard in the part of the living body as a necrosis area.

<21> The device for measuring biokinetics according to item <18>, which further includes tumescence progression-predicting means of predicting a degree of tumescence which will advance in future from the transfer speed into or out of the interstitial tissue fluid in the part of the living body.

<22> The device for measuring biokinetics according to item <21>, wherein the tumescence progression-predicting means predicts a degree of tumescence progression corresponding to the transfer speed into the interstitial tissue fluid after a predetermined time course until the cyclodextrin-bonded indocyanine compound is dispersed in blood in a whole body from the administration of the diagnostic composition.

<23> A device for measuring biokinetics including:
excitation light-irradiating means of irradiating excitation light to a cyclodextrin-bonded indocyanine compound in a part of a living body or a control moiety to which the diagnostic composition according to item <16> or <17> is administered;
fluorescence intensity-measuring means of measuring an intensity of fluorescence emitted by the cyclodextrin-bonded indocyanine compound which has been excited by the excitation light-irradiating means;
biokinetics-calculating means of calculating a transfer speed of the cyclodextrin-bonded indocyanine compound in the part of the living body into and/or out of interstitial tissue fluid by obtaining a change with time in the fluorescence intensity from the fluorescence intensities acquired by the fluorescence intensity-measuring means with time; and
tumescence progression-predicting means of predicting a degree of tumescence which will advance in future from the transfer speed into or out of the interstitial tissue fluid in the part of the living body,
wherein the tumescence progression-predicting means is means of
obtaining a relationship between a volume of blood flowing in the control moiety and a volume of blood flowing in the part of the living body, from a change in the fluorescence intensity in the part of the living body and a change in the fluorescence intensity in the control moiety up to a predetermined time until the cyclodextrin-bonded indocyanine compound is dispersed in blood in a whole body after the administration of the diagnostic composition,
calculating a degree of the change in the fluorescence intensity in the part of the living body comparing with the change in the fluorescence intensity in the control moiety, using the relationship after the predetermined time course, and
predicting a degree of tumescence progression corresponding to the degree of the change calculated above.

<24> A device for measuring biokinetics including: excitation light-irradiating means of irradiating excitation light to a cyclodextrin-bonded indocyanine compound in an organ of a living body to which the diagnostic composition according to item <16> or <17> is administered;
fluorescence intensity-measuring means of measuring an intensity of fluorescence emitted by the cyclodextrin-bonded indocyanine compound which has been excited by the excitation light-irradiating means; and
biokinetics-calculating means of evaluating biokinetics of the cyclodextrin-bonded indocyanine compound in the organ from the fluorescence intensity acquired by the fluorescence intensity-measuring means with time.

<25> The device for measuring biokinetics according to item <24>, wherein the organ is any one of kidney, ureter, bladder and urethra.

Effect of the Invention

A compound can be provided from the cyclodextrin-bonded indocyanine compound represented by the chemical formula 1 or chemical formula 2 of the present invention which is a green pigment and exhibits near-infrared fluorescence characterized in that a solubility in water or physiological saline is higher than that of ICG, it can be easily removed from a biological tissue, a molecule association is low in an aqueous solution, a near-infrared fluorescence intensity is high in an aqueous solution, fluorescence imaging of organs other than liver can be performed, and it includes no iodine. In addition, the synthesis method of the cyclodextrin-bonded indocyanine compound of the present invention can provide a useful synthesis of the cyclodextrin-bonded indocyanine compound. Additionally, the purification method of the cyclodextrin-bonded indocyanine compound of the present invention can provide a useful purification of the cyclodextrin-bonded indocyanine compound. Further, the cyclodextrin-bonded indocyanine compound of the present invention shows a sufficient solubility even if it does not include iodine, and, accordingly, it can provide a diagnostic composition including no iodine which leads to iodine hypersensitivity. This diagnostic composition shows a biobehavior different from a diagnostic composition including conventional ICG alone, and thus can provide various useful devices utilizing the properties.

MODE FOR CARRYING OUT THE INVENTION

Figure 1:
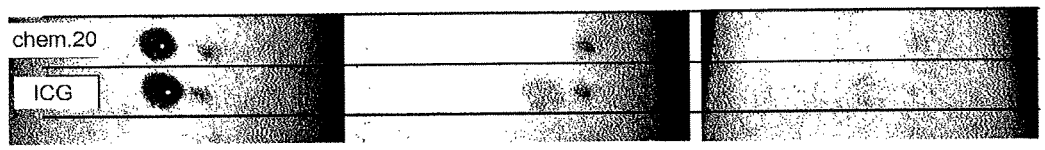
FIG. 1 shows results of adsorption tests of ICG and the isomerization equilibrium compound (TK1) represented by the chemical formula 19 or 20 to human skin. It shows a state immediately after application of 1 mM aqueous solution (0.03 mL) including ICG or the isomerization equilibrium compound (TK1) represented by the chemical formula 19 or 20 to an arm (a left photograph), a state immediately after washing it with water 5 minutes later (a middle photograph), and a state immediately after rubbing it and washing it with water (a right photograph), wherein a point at a right side is a marker by a red pen.

The diagnostic composition of the present invention can be used in diagnosis even if iodine is not included by employing the cyclodextrin-bonded indocyanine compound of the present invention described below as a pigment. The diagnostic composition can be substituted for a diagnostic composition including an indocyanine green which has hitherto been used. The application thereof may include, for example, liver function test drugs, circulatory function test drugs, and the like. In addition, the composition can be applied to medical operations and medial diagnosis in which near-infrared fluorescence emitted by administration thereof to a body such as a blood vessel, lymph vessel, brain, eye, stomach, breast, esophagus, skin, kidney, ureter, bladder, urethra, lung, heart, or other moiety is observed. It is considered that the pigment included in the diagnostic composition of the invention has a low binding property to a living body, and it can label a necessary moiety over along time. The diagnostic composition may include a salt as an isotonizing agent and other additives if necessary. A form in which the ingredients are arbitrarily dissolved may be employed, in addition to a form which is previously prepared in the state of an aqueous solution. This diagnostic composition can be administered by an injection, infusion, application or oral administration.

This diagnostic composition can be preferably used when a circulation of an aqueous solution such as blood, lymph fluid, interstitial tissue fluid, or urine is visualized. The visualization of the circulation of blood can be used, for example, in a determination of necrosis by evaluating a peripheral circulation, an evaluation of tissue engagement after a revascularization or transplant operation, a diagnosis of blood circulation failure, or the like. In addition, it is applicable to an eyeground imaging, an evaluation of a cerebral circulation, an imaging during an operation in a brain surgical operation, an identification of a sentinel lymph node in a cancer (a breast cancer, esophagus cancer, stomach cancer, colon cancer, prostate cancer, skin cancer, and the like), an evaluation of lymphedema, an intraoperative cholangiography, a marking of tumor, a coronary artery imaging, an abdominal blood vessel imaging (hepatic artery, abdominal aorta, digestive tract blood flow, and the like), in these filed, the visualization has hitherto been performed. The composition also enables a fluorescence imaging of a kidney and excretory system such as kidney, ureter, bladder, or urethra.

<1. Non-Inclusion Type Cyclodextrin-Bonded Indocyanine Compound and Synthesis Thereof>

The non-inclusion type cyclodextrin-bonded indocyanine compound of the present invention may include the chemical formula 1, the chemical formula 3, the chemical formula 5, the chemical formula 7, the chemical formula 9 and the chemical formula 11, and a synthesis method thereof can be performed by reacting an indocyanine compound with a cyclodextrin compound in a solution.

In the chemical formulae 1 and 3, $R_1$ to $R_4$ and $R_{13}$ to $R_{16}$ desirably are not bulky so that they do not hinder the inclusion by the cyclodextrin, considering the inclusion in the area corresponding to the cyclodextrin. Examples thereof are hydrogen, and alkyl groups and alkoxy groups having about 1 to 3 carbon atoms. The hydrogen, methyl group and methoxy group are particularly desirable, and the hydrogen is more desirable. Also, $R_5$, $R_6$, $R_{11}$ and $R_{12}$ desirably are not bulky for the inclusion in the cyclodextrin, though not to the extent of $R_1$ to $R_4$ and $R_{13}$ to $R_{16}$. Examples thereof include hydrogen, and alkyl groups and alkoxy groups having about 1 to 6 carbon atoms. As $R_1$ to $R_6$ and $R_{11}$ to $R_{16}$ are moieties included by the cyclodextrin, the moiety is desirably hydrophobic as a whole, even when a hydrophilic functional group is introduced thereto. As $R_{17}$, $R_{18}$, $R_{22}$ and $R_{23}$ have a little influence on the inclusion in the cyclodextrin, they are not particularly limited so long as they are the substituents described above. $R_7$, $R_{10}$, $R_{19}$ and $R_{21}$ are desirably hydrogen in terms of the easy synthesis. In addition, $R_8$, $R_9$ and $R_{20}$ are not particularly limited so long as they are the substituents described above.

When the non-inclusion type cyclodextrin-bonded indocyanine compound of the present invention is formed by covalently bonding the indocyanine compound to the cyclodextrin compound through an amide bond, a synthesis method of the non-inclusion type cyclodextrin-bonded indocyanine compound can be performed by a dehydration-condensation reaction of the indocyaninecarboxylic acid compound with the aminocyclodextrin compound in a solution.

<2. Inclusion Type Cyclodextrin-Bonded Indocyanine Compound>

The cyclodextrin-bonded indocyanine compound of the present invention is a cyclodextrin-bonded indocyanine compound represented by the chemical formula 2 wherein an indocyanine is covalently bonded to a cyclic sugar chain cyclodextrin, which is characterized in that at least a part of the naphthyl group of the indocyanine is included in a cavity of the cyclodextrin. The compound may have a substituent on the indocyanine group so long as the naphthyl group of the indocyanine is included in the cavity of the cyclodextrin, and the compound exhibits near-infrared fluorescence. Although various kinds of cyclodextrins are known, it is necessary that the naphthyl group on the indocyanine is included in the cavity of the cyclodextrin. Examples thereof may include α-cyclodextrin, β-cyclodextrin and γ-cyclodextrin, preferably β-cyclodextrin. The cyclodextrin may have a substituent.

In the chemical formulae 2 and 4, $R_1$ to $R_4$ and $R_{13}$ to $R_{16}$ desirably are not bulky so that they do not hinder the inclusion in the cyclodextrin. Examples thereof are hydrogen, and alkyl groups and alkoxy groups having about 1 to 3 carbon atoms. The hydrogen, methyl group and methoxy group are particularly desirable, and the hydrogen is more desirable. Also, $R_5$, $R_6$, $R_{11}$ and $R_{12}$ desirably are not bulky for the inclusion in the cyclodextrin, though not to the extent of $R_1$ to $R_4$ and $R_{13}$ to $R_{16}$. Examples thereof include hydrogen, and alkyl groups and alkoxy groups having about 1 to 6 carbon atoms. As $R_1$ to $R_6$ and $R_{11}$ to $R_{16}$ are moieties included in the cyclodextrin, the moiety is desirably hydrophobic as a whole, even when a hydrophilic functional group is introduced thereto. As $R_{17}$, $R_{18}$, $R_{22}$ and $R_{23}$ have little influence on the inclusion in the cyclodextrin, they are not particularly limited so long as they are the substituents described above. $R_7$, $R_{10}$, $R_{19}$ and $R_{21}$ are desirably hydrogen in terms of the easy synthesis. In addition, $R_8$, $R_9$ and $R_{20}$ are not particularly limited so long as they are the substituents described above. It is enough that the bond between the indocyanine group and the cyclodextrin is a covalent bond, and it is not particularly limited. Examples thereof may include an alkyl bond, amino bond, amide bond, double bond, triple bond, ester bond, ether bond, and the like. If efficiency on the chemical synthesis is emphasized, the amide bond is preferred.

In order to include at least a part of the naphthyl group of the indocyanine in the cavity of the cyclodextrin, it is preferable to use a spacer and covalently bond the indocyanine to the cyclic sugar chain cyclodextrin through the spacer. At this time, when the length of the spacer in the chemical formula 2 is controlled, it is possible to control a degree of the inclusion of the naphthyl group of the indocyanine in the cavity of the cyclodextrin.

The cyclodextrin-bonded indocyanine compound which is characterized in that the indocyanine is covalently bonded to the cyclic sugar chain cyclodextrin through the spacer, and the naphthyl group of the indocyanine is included in the cavity of the cyclodextrin, accordingly, can be preferably exemplified by the compound represented by the chemical formula 4. In addition, preferable examples thereof are compounds of the chemical formula 6, the chemical formula 8, or the chemical formula 10. Furthermore, the compound of the chemical formula 12 is more preferable. With respect to m, n, p and q in the chemical formula 6, m+p and n+q are each desirably 5 or more and 7 or less. In every chemical formula (the chemical formulae 1 to 10), the structure (spacer) between the nitrogen atom in the structure corresponding to the indocyanine and the oxygen atom in the structure corresponding to the cyclodextrin has desirably 7 or more and 9 or less atoms, considering the easy inclusion in the cyclodextrin.

<3. Synthesis of Inclusion Type Cyclodextrin-Bonded Indocyanine Compound>

The inclusion type cyclodextrin-bonded indocyanine compound of the present invention are compounds as described above, and the synthesis method thereof can be performed by dissolving the non-inclusion type cyclodextrin-bonded indocyanine compound, which is synthesized as above and used as a synthesis precursor, in an aqueous solution. The aqueous solution may include any material so long as it does not hinder the inclusion, and the water content is not particularly limited. The suitable temperature at the inclusion is from −20° C. to 100° C., preferably from 0° C. to 50° C. The time required for the inclusion is about one month immediately after the addition to the aqueous solution. As described above, it is clear that the inclusion reaction may take various formats depending on the property of the non-inclusion type cyclodextrin-bonded indocyanine compound, the inclusion reaction temperature, the composition or the concentration of the aqueous solution, and the like.

The non-inclusion type cyclodextrin-bonded indocyanine compound of the present invention can be converted into the inclusion type cyclodextrin-bonded indocyanine compound by dissolving it in a medium including water. The water content in the medium is not particularly limited, and it is desirably 50% by mass or more because when the content is higher, the inclusion easily advances in principle. If there is a compound capable of forming the inclusion type cyclodextrin-bonded indocyanine compound in a medium other than the aqueous solution, it is not necessary to perform the inclusion using the aqueous solution.

The inclusion type cyclodextrin-bonded indocyanine compound may be formed at the stage of the synthesis of the non-inclusion type cyclodextrin-bonded indocyanine compound, and in such a case the inclusion reaction is not required again.

<4. Synthesis Method of Non-Inclusion Type Cyclodextrin-Bonded Indocyanine Compound (One Example of Synthesis)>

A synthesis of the compound represented by the chemical formula 11 is taken as an example. The indocyanine compound represented by the chemical formula 11 can be obtained, for example, by mixing the compound represented by the chemical formula 13, which is synthesized in a method described in Non Patent Document 5, the compound represented by the chemical formula 14, which is synthesized in a method described in Non Patent Document 6, a dehydration-condensing agent such as a water-soluble carbodiimide (WSC: for example, 1-ethyl-3-(3-dimethylaminopropyl)carbodiimide hydrochloride) or dicyclohexylcarbodiimide (DCC), and a medium such as pyridine, N,N-dimethylformamide or an aqueous solution; and reacting the mixture at −20° C. to 60° C. for 10 minutes to 100 hours. In addition, an activator such as 1-hydroxybenzotriazole (HOBt) may be added to activate the reaction. The amount of the dehydration-condensing agent is 2-fold or more moles of that of the compound represented by the chemical formula 13, and the amount of the medium used is not limited so long as the reaction products are dissolved and the dehydration-condensation reaction is not hindered. The activator is not limited so long as it activates the dehydration-condensation reaction, and the addition amount thereof is not limited so long as the dehydration-condensation reaction advances as expected.

[Chem. 13]

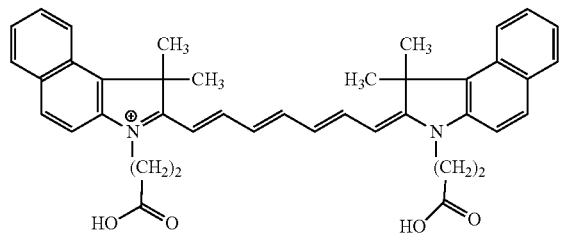

(13)

[Chem. 14]

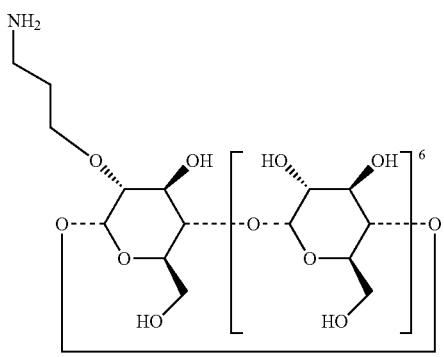

(14)

<5. Purification Method of Non-Inclusion Type Cyclodextrin-Bonded Indocyanine Compound>

A mixture including the non-inclusion type cyclodextrin-bonded indocyanine compound synthesized in the method described above is dissolved in an acidic aqueous solution, the resulting solution is applied to a reverse phase column chromatography, and elution thereof is performed using, as an eluate, for example, anyone of a mixed solution of water and methanol including an acid, a mixed solution of water and acetonitrile including an acid, a mixed solution of water and ethanol including an acid, and a mixed solution of water and acetone including an acid, whereby the non-inclusion type cyclodextrin-bonded indocyanine compound can be isolated and purified in a high purity. The acid is not limited so long as it does not decompose the non-inclusion type cyclodextrin-bonded indocyanine compound, the elution can be effectively performed and a post-treatment can be easily performed after the elution. Examples thereof may include hydrochloric acid, trifluoroacetic acid, acetic acid, sulfuric acid, nitric acid, formic acid, and the like. The hydrochloric acid, trifluoroacetic acid and acetic acid are preferable, and the hydrochloric acid is more preferable. The concentration of the acid is not limited, so long as it does not decompose the non-inclusion type cyclodextrin-bonded indocyanine compound, the elution can be effectively performed and a post-treatment can be easily performed after the elution. It is preferably from 0.01 mM to 10 mM, more preferably from 0.1 mM to 1 mM. When the concentration is adjusted to this range, the desired compound is not decomposed, and it can be quickly eluted. The medium is removed from the non-inclusion type cyclodextrin-bonded indocyanine compound eluted, whereby it can be obtained in a solid state. The medium can be removed by a lyophilization.

<6. Synthesis Method (One Example of Synthesis) and Purification Method (One Example of Purification) of Inclusion Type Cyclodextrin-Bonded Indocyanine Compound>

The non-inclusion type cyclodextrin-bonded indocyanine compound represented by the chemical formula 11 which has been synthesized and purified in the methods described above is the non-inclusion type, for example, in DMSO, but it is turned into the inclusion type compound represented by the chemical formula 12 immediately after it is dissolved in water. This phenomenon can be confirmed by an $^1$H NMR.

The inclusion type compound, accordingly, exists as the inclusion type compound in an aqueous solution, and can be used as the inclusion type compound. In addition, when water is removed from the aqueous solution including the inclusion type compound, it is possible to obtain the inclusion type compound in the solid state.

<7. Device for Measuring Biokinetics and Device for Visualizing Circulation Applied to Living Body to which Diagnostic Composition is Administered>

Device for Measuring Biokinetics

The present device is completed based on the feature in which the cyclodextrin-bonded indocyanine compound of the present invention employed as the diagnostic composition of the present invention (hereinafter may be arbitrarily referred to as the "compound of the present invention") has different biokinetics such as a degree of transfer into an interstitial tissue from that of ICG.

The compound of the present invention has difference from ICG in the metabolic rate and transfer speed from the circulatory system such as blood or lymph fluid into an interstitial tissue, and a proportion of the compound of the present invention which is uptaken into the interstitial tissue is relatively higher than that of ICG. When the kinetics of the compound of the present invention in a living body are analyzed, therefore, a mechanism of the body fluid shift in the living body (biokinetics) can be exactly evaluated. When the measurement conditions (an active state of a living body, an ambient temperature, and the like) are made stationary as much as possible upon the use of the present device, the biokinetics can be more exactly measured.

One form of an abnormal body fluid shift in a living body is generation of edema. Here, according to so-called "Starling hypothesis," it is generally considered that a body fluid (fluid) in a living body flows from an artery to an interstitial tissue, and then from the interstitial tissue to a vein.

It can be considered that this fluid shift from the artery to the vein can be calculated as (A)−(B)−(C)+(D) wherein (A) is a fluid shift flowing toward the outside of a circulatory system caused by a difference between an artery pressure and an interstitial tissue pressure, (B) is a fluid shift flowing toward the inside of the circulatory system caused by a difference between a vein pressure and the interstitial tissue pressure, (C) is a fluid shift flowing from an interstitial tissue into an artery caused by a difference between an osmotic pressure of interstitial tissue fluid and an osmotic pressure of arterial blood, and (D) is a fluid shift flowing from the interstitial tissue into a vein caused by a difference between an osmotic pressure of the interstitial tissue fluid and an osmotic pressure of venous blood.

When the difference between the artery pressure and the vein pressure becomes smaller due to heart failure, or the osmotic pressure of the interstitial tissue fluid lowers due to malnutrition, accordingly, the balance of the fluid shifts (A) to (D) breaks, thus resulting in generation of edema. In addition, when permeability of a capillary vessel becomes abnormal (abnormal selectivity of material penetration) as in diabetes mellitus, the balance of the fluid shifts (A) to (D) also breaks, thus resulting in generation of edema. Here, there has been a condition in which there is no simple method for directly evaluating an abnormal permeability of a capillary vessel, and therefore it has hitherto been difficult to specify a detail cause of generation of edema even if the generation of edema, which is a phenomenon, can be detected.

Under the finding described above, it can be expected that transfer of the compound of the present invention is changed by reduction of a difference between an artery pressure and a vein pressure or reduction of an osmotic pressure in a cell, compared to a case in which edema is generated, when material penetration becomes abnormal at a blood vessel wall of a capillary vessel. When the transfer of the compound of the present invention is observed in an amount equal to or more than (or less than) that corresponding to the fluid shift, accordingly, the generation of abnormal permeability of the capillary vessel can be determined. It can be considered that when the permeability of the capillary vessel does not become abnormal, the change of the transfer of the compound of the present invention corresponds to an extent of the fluid shift, and therefore it can be distinguished from the case in which the blood vessel wall becomes abnormal.

In particular, when two or more kinds of the compounds of the present invention having a transfer speed into the interstitial tissue different from each other are employed, and the biokinetics of these compounds are measured and compared with each other, the degree of change in the permeability of the capillary vessel may possibly be evaluated; in other words, when two or more kinds of the compounds of the present invention having a different permeability from each other through the blood vessel wall of the capillary vessel are employed, and the permeabilities thereof are measured, it becomes possible to more exactly evaluate whether or not the permeability becomes abnormal at the blood vessel wall. This means that the cause of the change in the fluid shift can be more exactly evaluated by employing two or more kinds of the compounds of the present invention having a different sensitivity to the abnormal permeability of the blood vessel wall to each other, and measuring the biokinetics thereof. In addition to the evaluation of the fluid shift by using the compound of the present invention, the fluid shift can be measured in a usual procedure.

The device for measuring biokinetics of the present invention has excitation light-irradiating means, fluorescence intensity-measuring means, biokinetics-calculating means, and other means. The other means is selected as occasion demand, and example thereof is concentration in a living body-calculating means of calculating a concentration of the cyclodextrin-bonded indocyanine compound from the fluorescence intensity measured by the fluorescence intensity-measuring means.

The present device is a device used for measuring at least a part of a living body to which the diagnostic composition of the present invention described above is administered. The amount of the diagnostic composition administered is an amount at which fluorescence can be observed when excitation light is irradiated to the moiety to be measured. The appropriate amount, accordingly, varies depending on the measurement moiety. The kind of the compound of the present invention included in the diagnostic composition is not particularly limited. The compounds of the present invention may be used alone or as a mixture of two or more kinds. A diagnostic composition having the same or different composition may be additionally administered in the course of the measurement.

The excitation light-irradiating means is means of irradiating excitation light having a wavelength capable of generating fluorescence from the compound of the present invention included in the diagnostic composition administered. The wavelength of the excitation light irradiated can be restricted to an appropriate range. When the wavelength is restricted to a range as narrow as possible, the fluorescence can be certainly separated from the excitation light. The wavelength can be restricted by selecting a light source capable of emitting light having an appropriate wavelength, or restricting a wavelength through a filter.

The mode of irradiation of the excitation light is not particularly limited so long as the fluorescence generated can be measured by the fluorescence intensity-measuring means described below. Example thereof may include contiguous excitation lights, pulsatile excitation light, excitation light whose intensity is variable, and the like. When the intensity is changed, the intensity of the excitation light can be modulated by irradiating pulses of the excitation light in a predetermined interval, and the like. It is desirable to modulate the intensity of the excitation light by employing pulse-amplitude modulation.

The excitation light is irradiated to a moiety to be irradiated by an appropriate optical system. The moiety to be irradiated is a moiety which requires measurement of biokinetics, for example, when an evaluation of a moiety in which edema is generated is intended, it is desirable to directly irradiate the excitation light to the moiety where the edema is generated.

A range to which the excitation light is irradiated is not particularly limited. The irradiation range is determined according to the need. When the light is irradiated to a narrow range, subdivided biokinetics can be precisely measured in the narrow range irradiated. When the light is irradiated to a wide range, a relative amount of the compound of the present invention which emits the fluorescence by the irradiation of the excitation light is increased, and thus the fluorescence intensity can be more precisely measured.

Further, it is preferable to irradiate the excitation light by the excitation light-irradiating means under a condition in which influence of ambient light is suppressed. For example, it is preferable to irradiate the excitation light in a dark place, or in a condition in which an area to which the excitation light is irradiated is covered from light from outside.

The fluorescence intensity-measuring means is means of measuring an intensity of the fluorescence emitted from a moiety in which the excitation light is irradiated by the excitation light-irradiating means. It is preferable to measure light from which light other than the fluorescence (ambient light, excitation light, and the like) is removed through a filter capable of selectively passing the fluorescence emitted.

When means of irradiating excitation light having a modulated intensity is employed as the excitation light-irradiating means, a component showing a change corresponding to the modulation can be separated from light intensity measured, which can be used as the fluorescence intensity. For example, when the intensity of the excitation light is modulated by pulse-amplitude modulation, a component of light which changes depending on the intensity of the pulse modulated is demodulated, and its intensity is measured, thereby separating the fluorescence intensity. This can reduce the influence by ambient light on the measurement results of the fluorescence intensity.

The concentration in a living body-calculating means is means of calculating a concentration of the compound of the present invention in the living body based on the fluorescence intensity measured by the fluorescence intensity-measuring means. The relationship between the fluorescence intensity and the concentration of the compound of the present invention in the living body can be calculated in an appropriate method. For example, a calibration curve is previously made, and a concentration of the compound of the present invention in a living body can be calculated based on the calibration curve. The absolute value of the fluorescence intensity can also be used as it is as a value relating to a concentration of the compound of the present invention in a living body. The concentration in a living body-calculating means calculates with time a concentration of the compound of the present invention in a living body.

The biokinetics-calculating means is means of obtaining a time-rate of change in the concentration of the compound of the present invention in a living body from the data of the concentrations in the living body acquired with time by the concentration in a living body-calculating means. The biokinetics-calculating means calculates a transfer speed of the compound of the present invention from the circulatory system into the interstitial tissue or from the interstitial tissue into the circulatory system in the part of the living body, from the resulting time-rate of change in the concentration in the living body. The transfer speed into or out of the interstitial tissue may also directly be calculated from the change in the fluorescence intensity obtained with time by the fluorescence intensity-measuring means, without using the concentrations in the living body.

Here, it can be assumed that there is a high correlation between the transfer of the compound of the present invention toward the inside (outside) of the interstitial tissue and the fluid shift in the body fluid, and therefore a state of fluid shift in a measurement moiety can be evaluated by measuring biokinetics of the compound of the present invention. In addition, it can be considered that when the blood vessel wall becomes abnormal and the material permeability is not normal, the kinetics of the compound of the present invention are changed in a living body. The permeability of the blood vessel, therefore, can be evaluated by the evaluation of the kinetics of the compound of the present invention.

The time-rate of change in the fluorescence intensity (or the concentration in the living body) can be obtained by differentiating the change with time in the fluorescence intensity (or the concentration in the living body) with time, or by calculating a fluorescence intensity (a concentration in a living body) per predetermined time to obtain a difference from a fluorescence intensity (or a concentration in a living body) before the predetermined time (after the predetermined time).

An uptake or excretion speed into or out of the interstitial tissue fluid of the compound of the present invention in a part of the living body is calculated, from the resulting time-rate of changes in the fluorescence intensity (or the concentration in the living body). Here, the uptake or excretion speed into or out of the interstitial tissue fluid can be obtained as a relative value from the fluorescence intensity, and also it can be calculated based on the concentration of the compound of the present invention in the interstitial tissue and the amount of the interstitial tissue fluid, when it is desired to obtain it more precisely. In addition, when the concentration and the amount of the compound of the present invention in blood or lymph fluid are taken into account, more precise calculation can be performed. The concentration of the compound of the present invention in blood or the like can be precisely measured by actually sampling the blood.

The method for calculating a concentration in the interstitial tissue fluid may be exemplified by the following methods. A first method is a method in which the concentration of the compound of the present invention in the living body calculated is approximated as the concentration thereof in interstitial tissue fluid in a part of a living body as it is. The concentration in the interstitial tissue fluid can be calculated in consideration of the amount of the interstitial tissue fluid as a method relevant to the first method. A second method is a method in which a concentration of the compound of the present invention in blood is actually measured, a proportion of contribution by materials in the blood vessel to a value measured by the fluorescence intensity-measuring means is calculated by a method using another standard substance which does not transfer to the interstitial tissue (such as ICG), and a concentration in the interstitial tissue fluid can be calculated by subtracting the influence caused by the concentration of the compound of the present invention in blood actually measured.

The time-rate of change in the concentration of the compound of the present invention in the interstitial tissue fluid can be calculated by subtracting the transfer speed out of the interstitial tissue from the transfer speed into the interstitial tissue. Here, when it is assumed that the transfer of the compound of the present invention into (or out of) the interstitial tissue advances in a speed correlating to a shift speed of fluid in body fluid and the fluid shift reaches equilibrium, the transfer speed into the interstitial tissue and the transfer speed out of the interstitial tissue can be considered as constants. The transfer speeds, therefore, can be calculated from the change in the concentration of the compound of the present invention in blood (the change caused by metabolism, excretion, transfer to tissues, and the like), and the time-rate of change in the concentration in the interstitial tissue fluid. Even if these transfer speeds vary, the transfer speeds can be calculated by making a model corresponding to the change and applying thereto.

When the transfer speed calculated is out of a range of values shown by a normal blood vessel wall, it can be considered that the blood vessel wall may become abnormal. There can be a case in which the permeability of the compound of the present invention is increased as well as a case in which it is decreased resulting from the abnormality of the blood vessel wall.

It is a well-known fact that tissue becomes acutely tumescent due to various tissue injuries such as acute inflammation, ischemia or trauma, and this is a very important tissue reaction in the medical setting, regardless of the region.

It is an item relevant to whole organs, for example, in an evaluation of suture of an intestine during an operation, an evaluation of a degree of an inflammation such as pneumonia, an evaluation of compatibility in an organ transplant, an evaluation of dysfunction in brain, kidney, and the like, in addition to the case in which the generation of tumescence itself becomes problems.

However, there is no means of exactly predicting a possibility or a degree of tissue tumescence at the current moment, and it is only empirically predicted from a degree of a tissue injury. In most cases, accordingly, a treatment must be considered after the generation of tumescence is confirmed, which is a big therapeutic restrictions.

If the possibility of tumescence generated can be early predicted in a high precision, a treatment of reducing the tumescence can be early performed whereby the influence can be suppressed to the minimum. For example, if a degree of a brain edema, which will be caused later, can be exactly predicted immediately after bleeding from the brain, the influence can be kept to the minimum by early performing a decompression treatment or a treatment for reducing a blood vessel permeability. Similarly, if an influence caused by ischemia stress can be predicted in advance, a secondary damage caused by myocardial infarction or extremity injury can be kept to the minimum. As stated above, a technique of highly precision, quantitative prediction of tumescence has a potential to provide considerable impact on the entirety of the medical practice.

The quantification of tumescence of tissues including edema has hitherto been qualitatively evaluated from an appearance. The quantification has been tried, but it can be performed only under very limited conditions, and has a defect in which the evaluation can be performed only after the generation of the tumescence.

In order to solve these problems, when the device for measuring biokinetics of the present invention is used, the tumescence progression can be predicted by calculating a fluid shift speed into or out of the interstitial tissue. As described in detail in Examples, it is known that ICG does not transfer to the interstitial tissue during the tumescence progression. On the other hand, it is known that the cyclodextrin-bonded indocyanine compound of the present invention can transfer into or out of the interstitial tissue, and the transfer into the interstitial tissue is further promoted with the fluid shift during the tumescence progression. The tumescence progression, accordingly, can be predicted by evaluating the transfer of the cyclodextrin-bonded indocyanine compound of the present invention into the interstitial tissue.

As it is considered that the fluid shift speed into or out of the interstitial tissue exerts influence on how big tumescence finally formed is, evaluation of the transfer speed of the cyclodextrin-bonded indocyanine compound of the present invention, which is relevant to the fluid shift speed, can leads to the evaluation of a degree of final tumescence progression. The transfer speed can be obtained by calculating a concentration of the cyclodextrin-bonded indocyanine compound, or it may be calculated by using the fluorescence intensity as it is. The transfer speed into or out of the interstitial tissue can be calculated as an absolute value needless to say, and also a relative value (for example, a rate of change in the fluorescence intensity may be adopted as a value relevant to the transfer speed as it is) is calculated and tumescence progression can be predicted according to the relative value.

The calculation of the tumescence progression is desirably performed based on a transfer speed into the interstitial tissue in a normal period in which the tumescence does not advance. There are, however, cases in which the transfer speed into the interstitial tissue is not found in the normal period, and in such cases, therefore, a moiety in which the tumescence does not advance is selected as a control moiety, and a transfer speed obtained in that moiety can be used instead thereof. The degree of the transfer of the cyclodextrin-bonded indocyanine compound of the present invention into the interstitial tissue may also be evaluated by evaluating an amount of blood circulating and a degree of metabolism using ICG which does not transfer into the interstitial tissue.

The degree of transfer of the cyclodextrin-bonded indocyanine compound of the present invention into the interstitial tissue is measured after a predetermined time course from the administration of the diagnostic composition of the present invention to a living body. The predetermined time refers to a time necessary for distribution of the diagnostic composition of the present invention in blood. The reason why the evaluation is performed using data after the predetermined time course is that there is almost no difference in the change of fluorescence intensity regardless of the tumescence progression, because the concentration in blood is quickly elevated with almost no influence caused by a degree of tumescence progression until the diagnostic composition is distributed in blood over the predetermined time after the administration thereof. Once it is distributed in blood, the transfer speed into the interstitial tissue is changed depending on the presence or absence of the tumescence progression, and accordingly it can be observed selective increase of the fluorescence intensity in a moiety in which the transfer advances (i.e., a moiety in which the tumescence advances).

A concrete method for presuming the tumescence progression may include, for example, a method in which a blood volume is presumed from a body weight or the like, a size of a peak of the fluorescence intensity and a time reaching the peak are calculated from the blood volume presumed. Considering the time and the intensity, a fluorescence intensity is measured at a time when the intensity will be changed with generation of edema, and a degree of edema progression and a degree of edema which will be probably generated in future are predicted from the obtained results.

Device for Visualizing Circulation

The device is completed based on the fact in which the cyclodextrin-bonded indocyanine compound of the invention (hereinafter may be arbitrarily refereed to as the "compound of the present invention") employed in the diagnostic composition of the invention is different from ICG in biokinetics such as a degree of transfer into an interstitial tissue.

The compound of the present invention easily transfers into interstitial tissue fluid, and thus it becomes possible to visualize a circulation of blood or lymph fluid by tracing the behavior of the compound of the present invention.

The device for visualizing circulation of the present invention has excitation light-irradiating means, fluorescence-imaging means, morphological imaging means and displaying means. The device is a device used for measuring at least a part of the living body to which the diagnostic composition of the invention described above is administered. The amount of the diagnostic composition administered is an amount at which fluorescence can be observed when excitation light is irradiated to the moiety to be measured. The appropriate amount, accordingly, varies depending on the measurement moiety. The kind of the compound of the present invention included in the diagnostic composition is not particularly limited. The compounds of the present invention may be used alone or as a mixture of the two or more kinds. A diagnostic composition having the same or different composition may be additionally administered in the course of the measurement.

The excitation light-irradiating means is means of irradiating excitation light having a wavelength capable of generating fluorescence from the compound of the present invention included in the diagnostic composition administered. The wavelength of the excitation light irradiated can be restricted to an appropriate range. When the wavelength is restricted to a range as narrow as possible, the fluorescence can be certainly separated from the excitation light. The wavelength can be restricted by selecting a light source capable of emitting light having an appropriate wavelength, or restricting a wavelength through a filter.

The mode of irradiation of the excitation light is not particularly limited so long as the fluorescence generated can be measured by the fluorescence-imaging means described below. Example thereof may include contiguous excitation lights, pulsatile excitation light, excitation light whose intensity is variable, and the like. When the intensity is changed, the intensity of the excitation light can be modulated by irradiating pulses of the excitation light in a predetermined interval, and the like. It is desirable to modulate the intensity of the excitation light by employing pulse-amplitude modulation.

The excitation light is irradiated to a moiety to be irradiated by an appropriate optical system. The moiety to be irradiated is a moiety in which the visualization of circulation is required in a living body, and may include, for example, a moiety at which necrosis of tissue is advancing due to thermal injury, frostbite, inflammation, wound or infarction, and periphery thereof. As Blood is not circulated in the moiety in which the tissue is necrotized and there is little advantage even if that moiety is left as it is, the removal thereof is thought. In such a case, it is ideal to completely remove the necrosis area alone among the normal area and the necrosis area.

The identification of the necrosis area has hitherto been performed by a blood vessel angiography in which a contrast agent is administered, or a method in which hypothermia is detected with decrease of blood circulation. The blood vessel angiography, however, has a defect in which it is not easy to handle devices such as X-ray irradiation device, and according to the evaluation method based on the body temperature, it is not easy to obtain an exact determination.

The device of the present invention can be used for an application in which evaluation of the necrosis area and the normal area is performed due to presence or absence of the circulation of body fluid (blood). If a moiety with no circulation can be visualized, then the moiety can be easily removed. In addition to the visualization of the necrosis area, it becomes possible to easily evaluate occurrence of abnormality in the circulatory function, because the blood circulation can be directly observed. For example, a moiety in which necrosis does not occur yet, but a circulatory function is decreased due to infarction can be visualized.

The range to be irradiated by the excitation light is decided so as to include an area requiring the visualization of the circulation as occasion demands.

Further, it is preferable to irradiate the excitation light by the excitation light-irradiating means under a condition in which influence of ambient light is suppressed. For example, it is preferable to irradiate the excitation light in a dark place, or in a condition in which an area to which the excitation light is irradiated is covered from light from outside.

The fluorescence-imaging means is a means of two-dimensionally acquiring an intensity of fluorescence emitted by the compound of the present invention which has been excited by the excitation light-irradiating means to obtain distribution state data of the compound of the present invention in a living body; i.e., this means is means of acquiring the distribution state data showing the distribution of the compound of the present invention in a part of a living body as two-dimensional image data.

It may be formed of, for example, a combination of an appropriate optical system and an image pick-up device such as CCD. A resolution of the data two-dimensionally acquired is set to a necessary value depending on the purpose. It is preferable to measure the fluorescence intensity of light from which light other than the fluorescence (ambient light, excitation light, and the like) is removed through a filter capable of selectively passing the fluorescence emitted.

When means of irradiating excitation light having a modulated intensity is employed as the excitation light-irradiating means, a component showing a change corresponding to the modulation can be separated from light intensity measured, which can be used as the fluorescence intensity. For example, when the intensity of the excitation light is modulated by pulse-amplitude modulation, a component of light which changes depending on the intensity of the pulse modulated is demodulated, and its intensity is measured, thereby separating the fluorescence intensity. This can reduce the influence by ambient light on the measurement results of the fluorescence intensity.

The morphological imaging means is means of two-dimensionally acquiring an intensity of light having a wavelength other than the wavelength of the fluorescence emitted by the compound of the present invention to obtain morphological data of a part of a living body, i.e., the means is means of acquiring morphological data showing the morphology of the part of the living body as two-dimensional image data.

The morphological imaging means can be formed of an appropriate optical system and an image pick-up device such as CCD. A resolution of the data two-dimensionally acquired is set to a necessary value depending on the purpose. In such a case, it is set so that the fluorescence emitted from the excitation light is not detected (or the detection sensitivity is lowered). As the morphological imaging means, a structure in which most of the optical system is used for this means and the fluorescence imaging means described above, and the light having a wavelength corresponding to the fluorescence is introduced into the fluorescence-imaging means and lights having other wavelengths is introduced in to the morphological imaging means through a spectral prism in an optical path before final introduction into the image pick-up device can be adopted. The spectral prism can appropriately control the wavelength of light to be separated by appropriately forming a dichroic film.

Further, one imaging device can be used as the fluorescence-imaging means and as the morphological-imaging means. The fluorescence may be mathematically separated from other lights after two-dimensional image data are obtained. Furthermore, the distribution state data can also be obtained as multiple image data from a surface of apart of a living body in a depth direction. A focal point in the optical system adopted in the fluorescence-imaging means is shifted in the depth direction, whereby multiple two-dimensional image data can be obtained in a depth direction. In addition, an optical system capable of changing a focal length is adopted as the excitation light-irradiating means, and the focal point is shifted not only on the surface of the part of the living body but also in the depth direction, or excitation light thinly stopped is irradiated to the part of the living body, whereby the fluorescence can be selectively generated not only on the surface of the living body but also on the inside in the depth direction of the living body, and the circulation at that area can be visualized.

The displaying means is means of displaying a distribution state of the compound of the present invention in a part of a living body by overlapping the distribution state data obtained by the fluorescence-imaging means with the morphological data obtained by the morphological imaging means. When a wavelength of fluorescence is not within a range of visible light, the wavelength of fluorescence is converted to an appropriated wavelength of visible light, which is displayed. It is desirable to display the distribution state data in preference to the morphological data in terms of the visualization of the circulation. In particular, an area in which a distribution quantity (i.e., a fluorescence intensity) of the compound of the present invention is low (whether it is low or not is decided in accordance with the purpose of visualizing the circulation. For example, for the purpose of visualizing a necrosis area, it is an area in which the circulation is not observed, i.e., an area in which fluorescence is not observed) is displayed so that it can be distinguished from other area. For example, the area can be displayed by a color different from that in another area, or can be displayed by blinking it. The overlapping of the distribution state data with the morphological data can be realized by logic on a computer. The two-dimensional data can be displayed by using a usual display device. When the display device is placed between a living body and a measurer, a living body can be treated while looking at the display device.

<8. Definitions, and the Like>

In the present invention, "alkyl group" refers to a linear or branched alkyl group having 1 to 20 carbon atoms, which may have a substituent, and examples thereof may include linear groups or branched groups including methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and icosanyl.

In the present invention, "alkoxyl group" may include linear or branched alkoxyl group having 1 to 20 carbon atoms, such as methoxy, ethoxy, propoxy, butoxy, pentyloxy, hexyloxy, methoxyethoxy, methoxypropoxy, ethoxyethoxy, ethoxypropoxy and methoxyethoxyethoxy groups.

In the present invention, "aryl group" may include aromatic hydrocarbons having 6 to 20 carbon atoms, such as phenyl and naphthyl.

EXAMPLE

The preferable embodiments of the present invention will be specifically explained by means of Examples, but the technical scope of the present invention is not limited to embodiments described below, and various modifications thereof can be carried out in the scope of the present invention.

<Test 1: Synthesis and Purification of Compounds Represented by Chemical Formula 15 and Chemical Formula 16>

A mixture of 0.20 g of compound represented by the chemical formula 13, 0.94 g of a compound represented by the chemical formula 14, 0.18 g of WSC, 0.12 g of HOBt, 4.0 mL of pyridine and 2.0 mL of N,N-dimethylformamide was stirred at 0° C. for 6 hours in a dark place. After that, 50 mL of acetone was added thereto, a precipitate was filtered under a reduced pressure. The precipitate was dissolved in an aqueous solution of 0.1% trifluoroacetic acid, and the solution was subjected to an ODS column chromatography. A mixed liquid of water and methanol including 1 mM hydrochloric acid was used as an eluate, and a compound represented by the chemical formula 15 was eluted. The eluate is concentrated under a reduced pressure to obtain 0.65 g of a green inclusion type compound represented by the chemical formula 16 in a solid state (In the concentration of the eluate under reduced pressure, the product is naturally turned into an inclusion type, because a water content is high at the end of the concentration).

[Chem. 15]

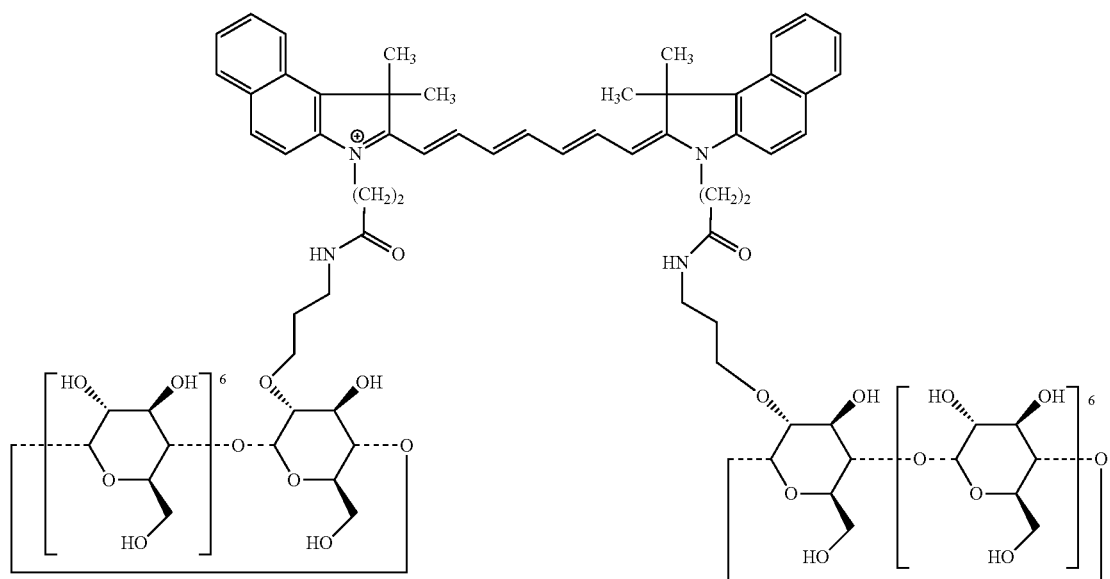

(15)

[Chem. 16]

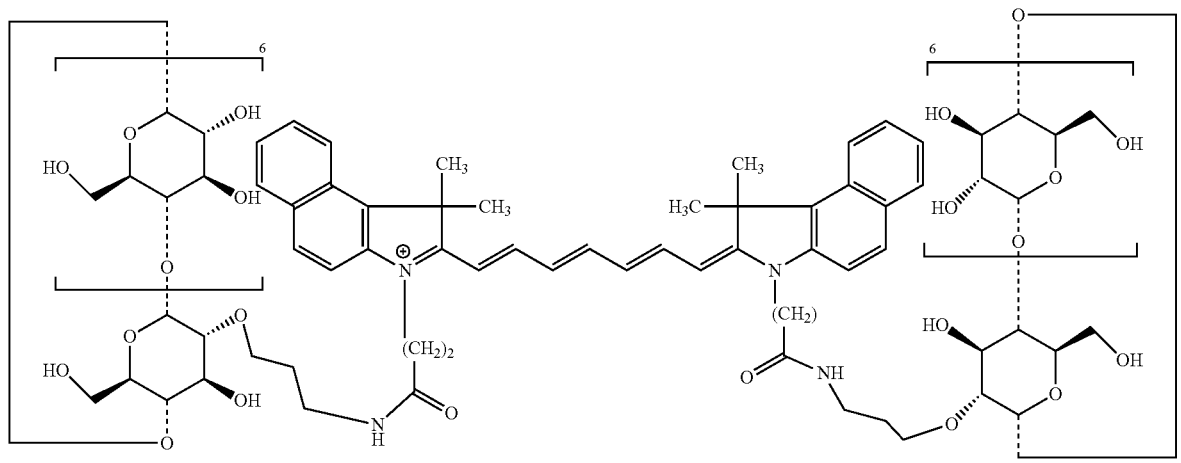

(16)

Mechanical analysis data of the desired product represented by the chemical formula 16 are shown below.

$^1$H NMR (500 MHz, D$_2$O, 26° C., Acetone: 2.10 ppm) 1.43 (2H, m), 1.55 (2H, m), 1.99 (6H, s), 2.09 (6H, s), 2.63 (6H, m), 2.80 (6H, m), 2.92 (2H, m), 3.02 (2H, dd, J=3.7, 9.8 Hz), 3.08 (2H, t, J=9.2 Hz), 3.2-4.1 (m), 4.19 (2H, t, J=9.8 Hz), 4.26 (2H, t, J=9.8 Hz), 4.33 (2H, m), 4.43 (2H, m), 4.71 (2H, d, J=2.4 Hz), 4.81 (4H, d, J=3.7 Hz), 4.91 (2H, d, J=3.7 Hz), 4.99 (2H, d, J=3.7 Hz), 5.08 (2H, d, J=3.7 Hz), 5.13 (2H, d, J=3.1 Hz), 6.15 (2H, d, J=13 Hz), 6.52 (2H, t, J=12 Hz), 7.43 (4H, m), 7.57 (1H, d, J=12 Hz), 7.57 (2H, d, J=9.2 Hz), 7.78 (2H, m), 8.06 (3H, m), 8.15 (2H, d, J=8.5 Hz). ESI-MS m/z calcd for C$_{131}$H$_{191}$N$_4$O$_{72}$ 2972, found 2973 [M]$^+$.

<Test 2: Synthesis and Purification of Compounds Represented by Chemical Formula 19 and Chemical Formula 20>

A mixture of 0.17 g of a compound represented by the chemical formula 17, 5 mL of methanol, and 0.30 g of t-BuOK was stirred at room temperature for 12 hours. After that, 3 mL of 1 M of hydrochloric acid, and then 50 mL of water were added thereto. A precipitate was filtered, washed with water, and dried under a reduced pressure to obtain 0.17 g of a compound represented by the chemical formula 18.

[Chem. 17]

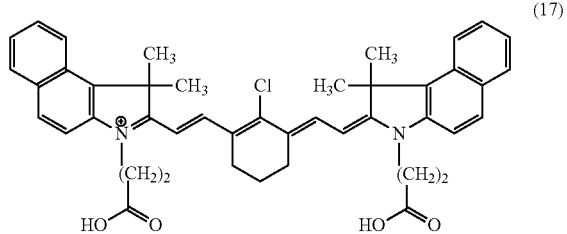

(17)

[Chem. 18]

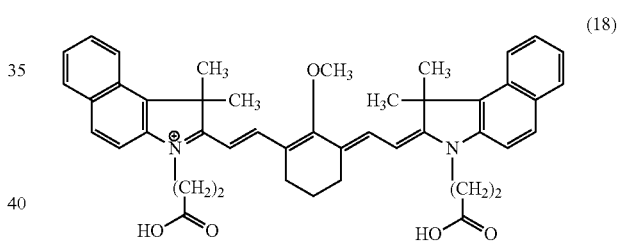

(18)

A mixture of 0.02 g of the compound represented by the chemical formula 18, 0.081 g of a compound represented by the chemical formula 14, 0.016 g of WSC, 0.011 g of HOBt, 0.3 mL of pyridine and 0.2 mL of N,N-dimethylformamide was stirred at 0° C. for 6 hours in a dark place. After that, 5 mL of acetone was added thereto, and a precipitate was filtered under a reduced pressure. The precipitate was dissolved in an aqueous solution of 0.1% trifluoroacetic acid, and the solution was subjected to an ODS column chromatography. A mixed liquid of water and methanol including 1 mM hydrochloric acid was used as an eluate, and a compound represented by the chemical formula 19 was eluted. The eluate was concentrated under a reduced pressure to obtain 0.045 g of a green inclusion type compound represented by the chemical formula 20 in a solid state. (In the concentration of the eluate under a reduced pressure, the product is naturally turned into an inclusion type, because a water content is high at the end of the concentration.)

[Chem. 19]

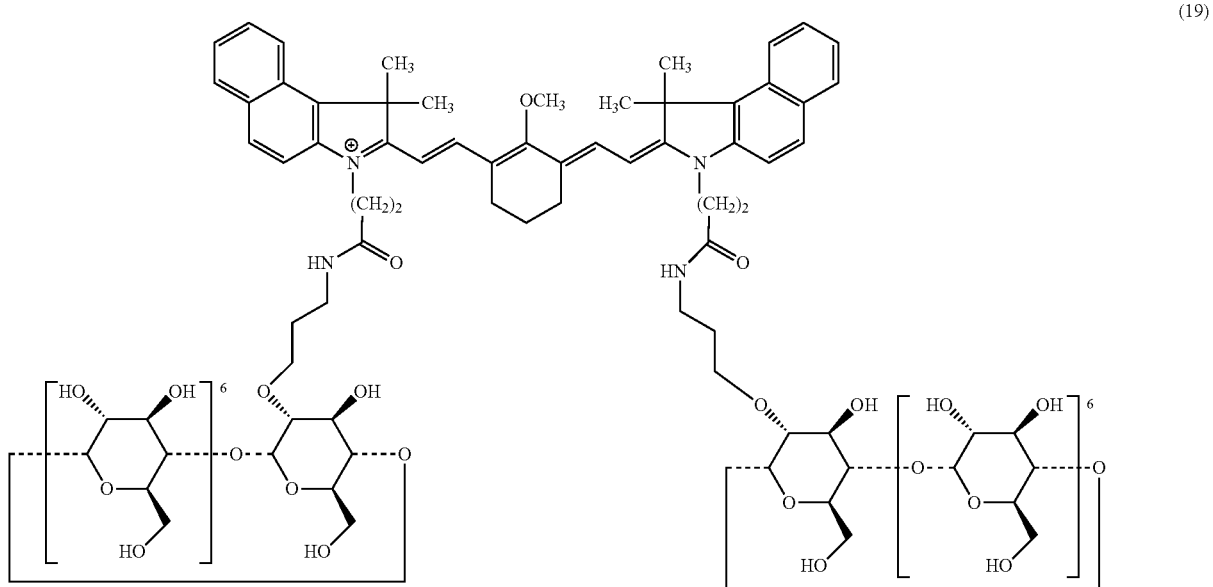

(19)

[Chem. 20]

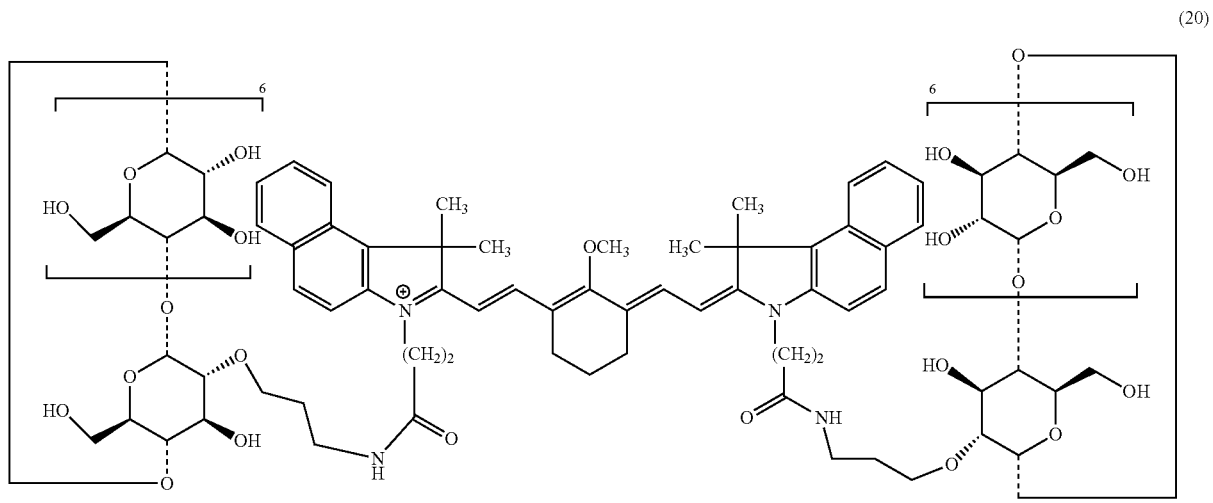

(20)

Mechanical analysis data of the desired product represented by the chemical formula 20 are shown below.

$^1$H NMR (500 MHz, D$_2$O, 40° C., Acetone: 2.26 ppm) 1.54 (2H, m), 1.68 (2H, m), 1.98 (2H, m), 2.19 (6H, s), 2.20 (2H, m), 2.30 (6H, s), 2.6-2.85 (10H, m), 2.95 (2H, m), 3.00 (4H, m), 3.08 (2H, t, J=12 Hz), 3.17 (2H, dd, J=3.7, 9.8 Hz), 3.26 (2H, t, J=9.8 Hz), 3.35-4.30 (m), 4.35 (2H, t, J=9.2 Hz), 4.50 (2H, t, J=9.2H), 4.52 (2H, m), 4.63 (2H, m), 4.87 (2H, d, J=3.7 Hz), 4.95 (d, J=3.1 Hz), 4.97 (2H, d, J=3.7 Hz), 5.08 (2H, d, J=3.7 Hz), 5.15 (2H, d, J=4.3 Hz), 5.25 (2H, d, J=3.7 Hz), 5.29 (2H, d, J=3.7 Hz), 6.30 (2H, d, J=14.6 Hz), 7.58 (4H, m), 7.73 (2H, d, J=8.5 Hz), 7.95 (2H, m), 8.25 (2H, m), 8.32 (2H, d, J=14.6 Hz), 8.35 (2H, d, J=8.5 Hz). ESI-MS m/z calcd for C$_{135}$H$_{197}$N$_4$O$_{73}$ 3042, found 3042 [M]$^+$.

<Test 3: Synthesis and Purification of Compound Represented by Chemical Formula 21>

A mixture of 0.04 g of a compound represented by the chemical formula 13, 0.18 g of mono-6-amino-6-deoxy-β-cyclodextrin, 0.05 g of WSC, 0.025 g of HOBt, 0.8 mL of pyridine and 0.4 mL of N,N-dimethylformamide was stirred at 0° C. for 3 hours in a dark place. After that, 10 mL of acetone was added thereto, and a precipitate was filtered under a reduced pressure. The precipitate was dissolved in an aqueous solution of 0.1% trifluoroacetic acid, and the solution was subjected to an ODS column chromatography. A mixed liquid of water and methanol including 1 mM hydrochloric acid was used as an eluate, and a compound represented by the chemical formula 21 was eluted. The eluate was concentrated under a reduced pressure to obtain 0.11 g of the green compound represented by the chemical formula 21 in a solid state.

[Chem. 21]

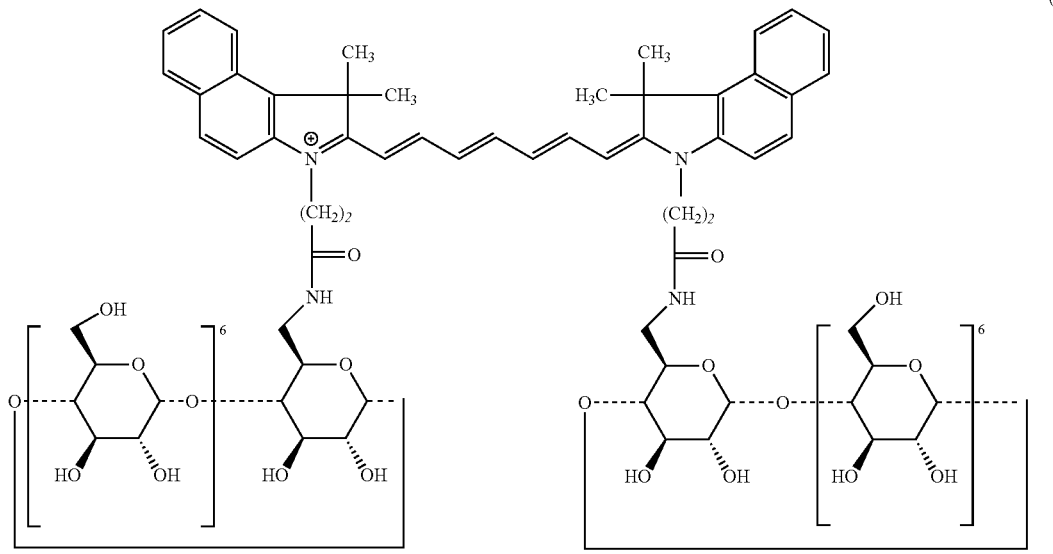

(21)

Mechanical analysis data of the desired product represented by the chemical formula 21 are shown below.

$^1$H NMR (500 MHz, $D_2O$, 29° C., Acetone: 2.10 ppm) 1.79 (12H, br.), 2.68 (4H, br.), 3.0-4.5 (98H, br.), 4.4 (4H, br.), 4.5-5.3 (14H, br.), 6.18 (2H, br.), 6.46 (2H, br.), 7.3-8.2 (15H). ESI-MS m/z calcd for $C_{125}H_{179}N_4O_{70}$ 2856, found 2856 $[M]^+$.

<Test 4: Synthesis and Purification of Compound Represented by Chemical Formula 23>

A mixture of 0.02 g of a compound represented by the chemical formula 22, 0.096 g of mono-6-amino-6-deoxy-β-cyclodextrin, 0.032 g of WSC, 0.5 mL of pyridine and 0.05 mL of 0.1 M phosphoric acid buffer was stirred at room temperature for 24 hours in a dark place. After that, 10 mL of acetone was added thereto, and a precipitate was filtered under a reduced pressure. The precipitate was dissolved in an aqueous solution of 0.1% trifluoroacetic acid, and the solution was subjected to an ODS column chromatography. A compound represented by the chemical formula 23 was eluted from the eluate using a mixed liquid of water and acetonitrile. The eluate was concentrated under a reduced pressure to obtain 0.014 g of the green compound represented by the chemical formula 23 in a solid state.

[Chem. 22]

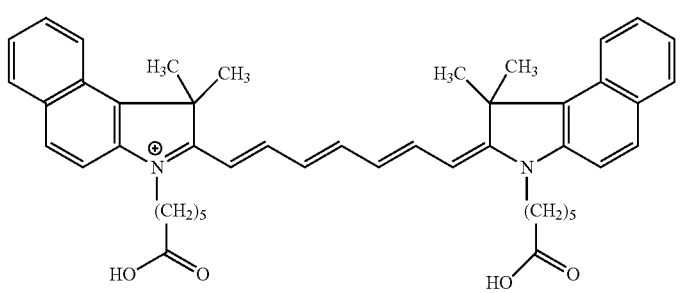

(22)

[Chem. 23]

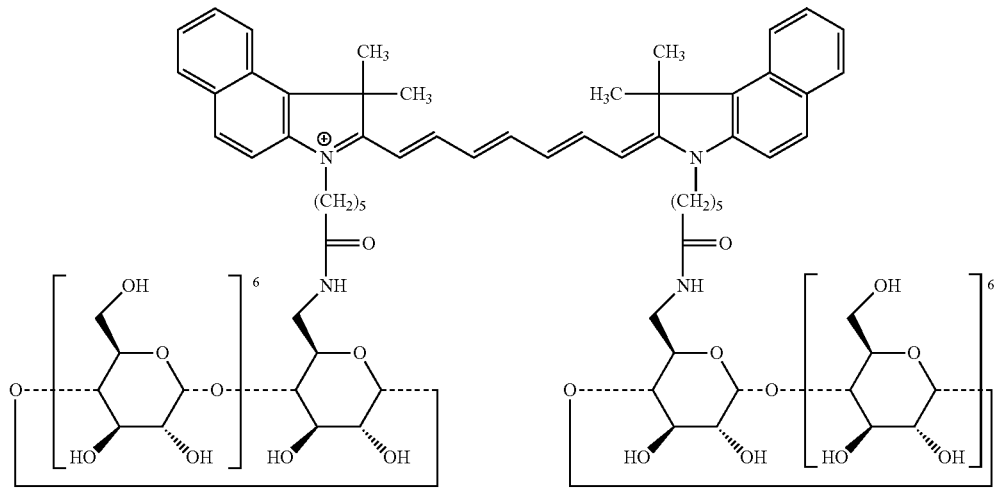

(23)

Mechanical analysis data of the desired product represented by the chemical formula 23 are shown below.

$^1$H NMR (500 MHz, D$_2$O, 26° C., Acetone: 2.15 ppm) 1.26 (4H, m), 1.5-2.25 (24H, br), 2.7-4.2 (88H), 4.82 (2H, br), 4.90 (8H, br), 4.97 (2H, br), 5.03 (2H, br), 6.11 (2H, br), 6.36 (2H, br), 7.3-8.01 (15H, br). ESI-MS m/z calcd for C$_{131}$H$_{191}$N$_4$O$_{70}$ 2940, found 2940 [M]$^+$.

<Test 5: Synthesis and Purification of Compound Represented by Chemical Formula 24>

[Chem. 24]

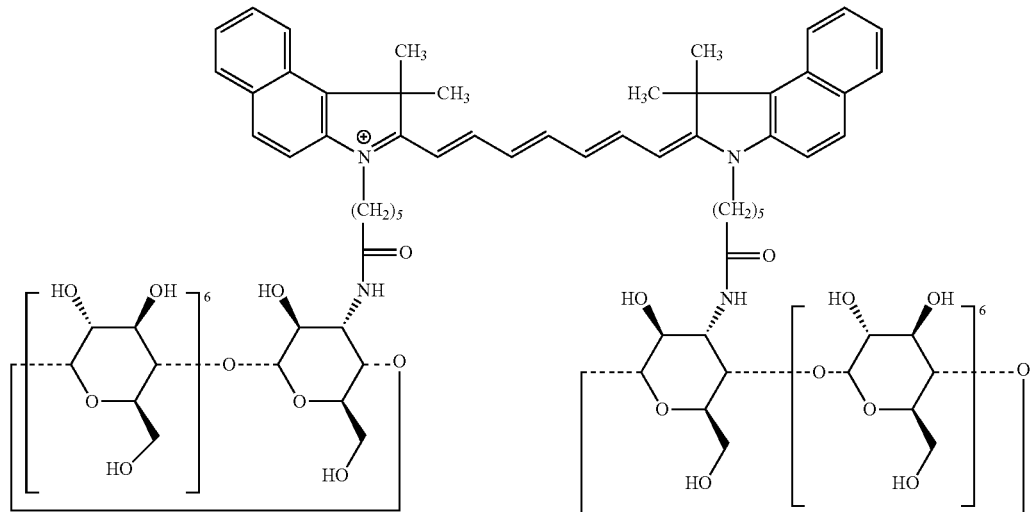

(24)

A mixture of 0.20 g of a compound represented by the chemical formula 22, 0.02 g of 3-amino-3-deoxy-β-cyclodextrin, 0.096 g of WSC, 0.013 g of HOBt, 0.4 mL of pyridine and 0.2 mL of N,N-dimethylformamide was stirred at room temperature for one hour in a dark place. After that, 10 mL of acetone was added thereto, and a precipitate was filtered under a reduced pressure. The precipitate was dissolved in an aqueous solution of 0.1% trifluoroacetic acid, and the solution was subjected to an ODS column chromatography. A compound represented by the chemical formula 24 was eluted from the eluate using a mixed liquid of water and methanol. The eluate was concentrated under a reduced pressure to obtain 0.013 g of the green compound represented by the chemical formula 24 in a solid state.

Mechanical analysis data of the desired product represented by the chemical formula 24 are shown below.

$^1$H NMR (500 MHz, D$_2$O, 29° C., Acetone: 2.10 ppm) 1.1-2.5 (28H), 3.0-4.25 (88H), 4.5-5.2 (14H), 7.3-8.02 (15H). ESI-MS m/z calcd for C$_{131}$H$_{191}$N$_4$O$_{70}$ 2940, found 2940 [M]$^+$.

<Test 6: Synthesis and Purification of Compound Represented by Chemical Formula 25>

A mixture of 0.02 g of a compound represented by the chemical formula 22, 0.1 g of a compound represented by the chemical formula 14, 0.032 g of WSC, 0.5 mL of pyridine and 0.05 mL of 0.1 M phosphoric acid buffer was stirred at room temperature for 24 hours in a dark place. After that, 10 mL of acetone was added thereto, and a precipitate was filtered under a reduced pressure. The precipitate was dissolved in an aqueous solution of 0.1% trifluoroacetic acid, and the solution was subjected to an ODS column chromatography. A compound represented by the chemical formula 25 was eluted from the eluate using a mixed liquid of water and methanol. The eluate was concentrated under a reduced pressure to obtain 0.021 g of the green compound represented by the chemical formula 25 in a solid state.

[Chem. 25]

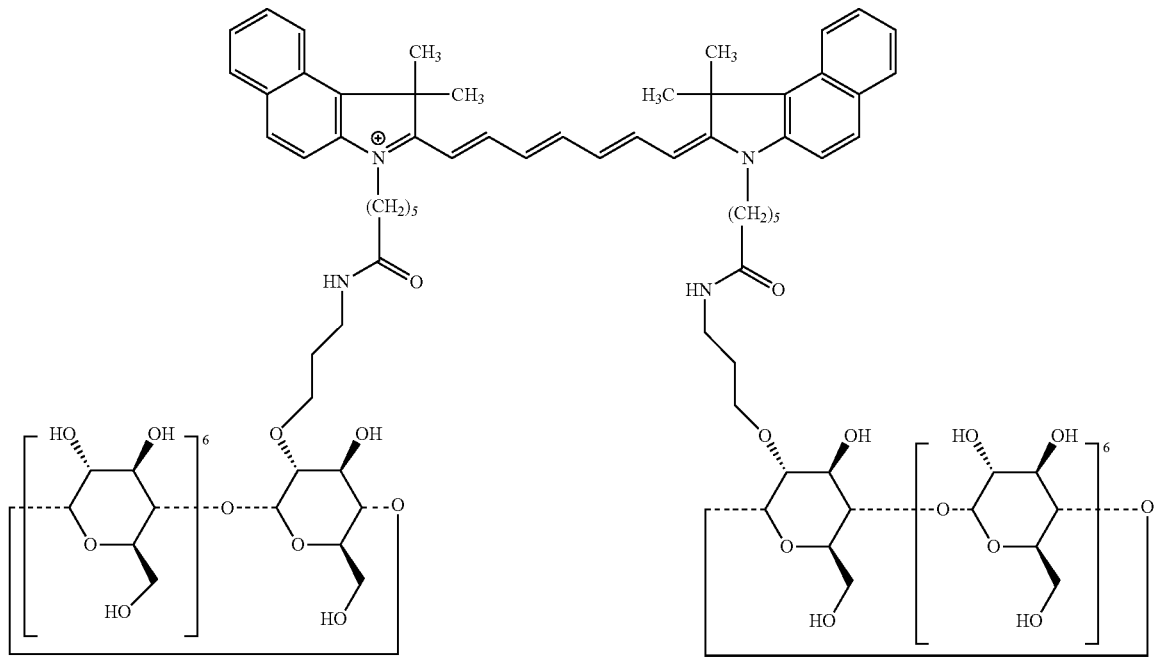

(25)

Mechanical analysis data of the desired product represented by the chemical formula 25 are shown below.

$^1$H NMR (500 MHz, D$_2$O, 25° C., Acetone: 2.10 ppm) 1.0-2.5 (32H), 3.0-4.5 (96H), 4.8-5.2 (14H), 6.09 (2H, br), 6.37 (2H, br), 7.3-8.02 (15H, br). ESI-MS m/z calcd for C$_{137}$H$_{203}$N$_4$O$_{72}$ 3056, found 3056 [M]$^+$.

<Test 7: Solubility of Cyclodextrin-Bonded Indocyanine Compound of Present Invention>

Solubility tests of ICG and the cyclodextrin-bonded indocyanine compounds of the present invention (the chemical formulae 16, 20, 21, and 23 to 25) in water or physiological saline were performed. About one minute violent vibration-stirring was necessary for dissolving powdery ICG from Molecular Probe Inc. in water or physiological saline. On the other hand, the vibration-stirring was not necessary for dissolving the cyclodextrin-bonded indocyanine compounds of the present invention, in particular, the compounds represented by the chemical formula 16 and the chemical formula 20, and they were quickly dissolved.

<Test 8: Adsorption of Cyclodextrin-Bonded Indocyanine Compound of Present Invention to Human Skin>

Adsorption tests of ICG and the cyclodextrin-bonded indocyanine compounds (the chemical formulae 16, 20, 21, and 23 to 25) of the present invention to human skin were performed. A 1 mM aqueous solution (0.03 mL) including ICG or each of the cyclodextrin-bonded indocyanine compounds of the present invention (the chemical formulae 16, 20, 21, and 23 to 25) was put on an arm, and it was washed with water after 5 minutes, rubbed it and further washed with water. The results were that ICG was not completely washed out with water; whereas, the cyclodextrin-bonded indocyanine compounds of the present invention, in particular the compounds represented by the chemical formula 16 and the chemical formula 20 could be easily washed out. It was shown that the adsorption of the cyclodextrin-bonded indocyanine compound of the present invention to the human skin was much lower than that of ICG (FIG. 1).

<Test 9: Adsorption of Cyclodextrin-Bonded Indocyanine Compound of Present Invention to Cellulose Fiber>

Figure 2:
FIG. 2 shows results of adsorption tests of ICG and the isomerization equilibrium compound (TK1) represented by the chemical formula 19 or 20 to a cellulose fiber. It shows a state immediately after application of 1 mM aqueous solution (0.05 mL) including ICG or the isomerization equilibrium compound (TK1) represented by the chemical formula 19 or 20 to a cotton swab (an upper photograph), and a state immediately after 5-second washing with running water after 3 minutes (a lower photograph).
Figure 2:
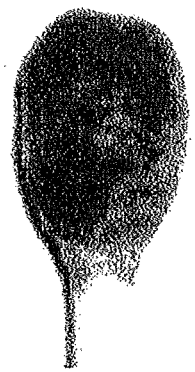
Figure 2:
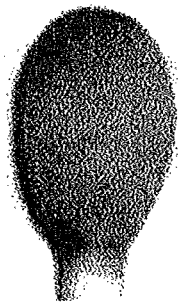
Figure 2:
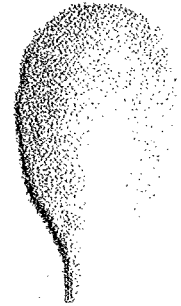

Adsorption tests of ICG and the cyclodextrin-bonded indocyanine compounds of the present invention (the chemical formulae 16, 20, 21, and 23 to 25) to a cellulose fiber were performed. Using a cotton swab (Sanyo Co., Ltd.) as a cellulose fiber model, a 1 mM aqueous solution (0.05 mL) including ICG or each of the cyclodextrin-bonded indocyanine compounds of the present invention (the chemical formulae 16, 20, 21, and 23 to 25) was applied to the model, and it was washed with running water (tap water, 1 L/minute) for 5 seconds after 3 minutes. The results were that ICG was not completely washed out with water; whereas, the cyclodextrin-bonded indocyanine compounds of the present invention, in particular the compounds represented by the chemical formula 16 and the chemical formula 20 could be easily washed out. It was shown that the adsorption of the cyclodextrin-bonded indocyanine compound of the present invention to the cellulose fiber was much lower than that of ICG (FIG. 2).

<Test 10: Adsorption of Cyclodextrin-Bonded Indocyanine Compound of Present Invention to Meat Model of Living Body>

Figure 3:
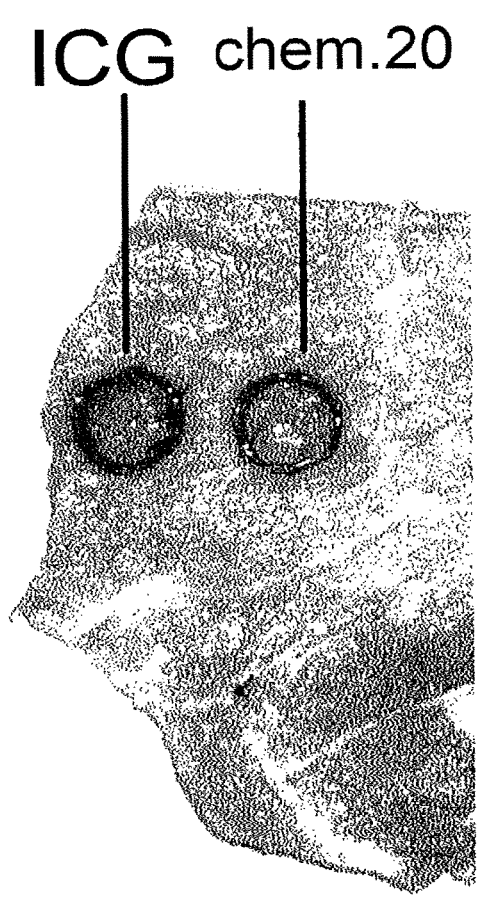
FIG. 3 shows results of adsorption tests of ICG and the isomerization equilibrium compound (TK1) represented by the chemical formula 19 or 20 to a meat model of a living body. It shows a state immediately after application of 1 mM aqueous solution (0.05 mL) including ICG or the compound represented by the chemical formula 20 to a depression part with a diameter of 5 mm of a pork loin meat (a left photograph), and a state immediately after 10-second washing with running water after 3 minutes (a right photograph).
Figure 3:

Adsorption tests of ICG and the cyclodextrin-bonded indocyanine compounds of the present invention (the chemical formulae 16, 20, 21, and 23 to 25) to a meat model of a living body were performed. Using a commercially available pork loin meat as the meat model of the living body, a depression part with a diameter of 5 mm was made on the pork loin meat, and a 1 mM aqueous solution (0.05 mL) including ICG or each of the cyclodextrin-bonded indocyanine compounds of the present invention (the chemical formulae 16, 20, 21, and 23 to 25) was applied to the depression part, and it was washed with running water (tap water, 1 L/minute) for 10 seconds after 3 minutes. The results were that ICG was not completely washed out with water; whereas, the cyclodextrin-bonded indocyanine compounds of the present invention, in particular the compounds represented by the chemical formula 16 and the chemical formula 20, could be easily washed out. It was shown that the adsorption of the cyclodextrin-bonded indocyanine compound of the present invention to the meat model of the living body was much lower than that of ICG (FIG. 3).

<Test 11: Adsorption of Cyclodextrin-Bonded Indocyanine Compound of Present Invention to Protein Model of Living Body>

Figure 4:
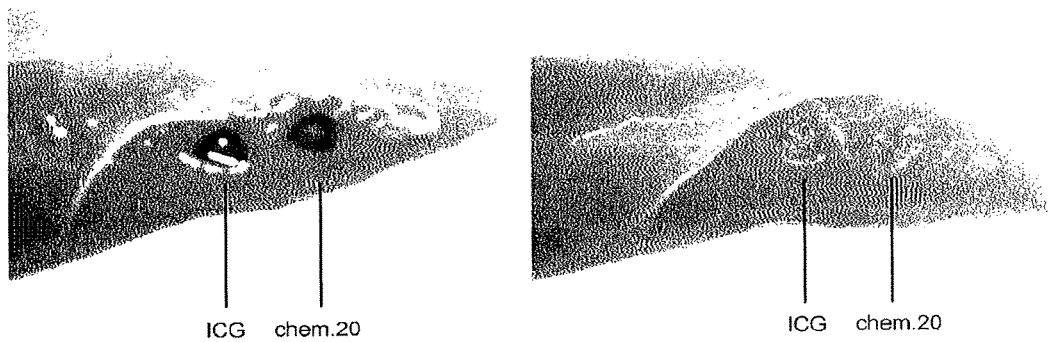
FIG. 4 shows results of adsorption tests of ICG and the isomerization equilibrium compound (TK1) represented by the chemical formula 19 or 20 to a protein model of a living body. It shows a state immediately after application of 1 mM aqueous solution (0.05 mL) including ICG or the isomerization equilibrium compound (TK1) represented by the chemical formula 19 or 20 to a depression part with a diameter of 5 mm of a chicken breast meat (a left photograph), and a state immediately after 10-second washing with running water after 3 minutes (a right photograph).

Adsorption tests of ICG and the cyclodextrin-bonded indocyanine compounds of the present invention (the chemical formulae 16, 20, 21, and 23 to 25) to a protein model of a living body. Using a commercially available chicken breast meat as the protein model of the living body, a depression part with a diameter of 5 mm was made on the chicken breast meat, and a 1 mM aqueous solution (0.05 mL) including ICG or each of the cyclodextrin-bonded indocyanine compounds of the present invention (the chemical formulae 16, 20, 21, and 23 to 25) was applied to the depression part, and it was washed with running water (tap water, 1 L/minute) for 10 seconds after 3 minutes. The results were that ICG was not completely washed out with water; whereas, the cyclodextrin-bonded indocyanine compounds of the present invention, in particular the compounds represented by the chemical formula 16 and the chemical formula 20, could be easily washed out. It was shown that the adsorption of the cyclodextrin-bonded indocyanine compound of the present invention to the protein model of the living body was much lower than that of ICG (FIG. 4).

<Test 12: Adsorption of Cyclodextrin-Bonded Indocyanine Compound of Present Invention to Hydrophobic Chemical Fiber>

Figure 5:
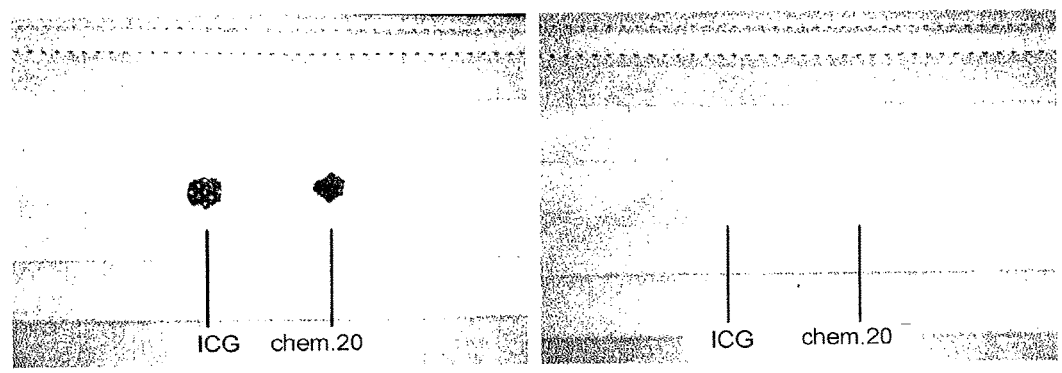
FIG. 5 shows results of adsorption tests of ICG and the isomerization equilibrium compound (TK1) represented by the chemical formula 19 or 20 to a hydrophobic chemical fiber. It shows a state immediately after application of 1 mM aqueous solution (0.05 mL) including ICG or the isomerization equilibrium compound (TK1) represented by the chemical formula 19 or 20 to a polypropylene mask (a left photograph), and a state immediately after one-second washing with running water after 20 minutes (a right photograph).

Adsorption tests of ICG and the cyclodextrin-bonded indocyanine compounds of the present invention (the chemical formulae 16, 20, 21, and 23 to 25) to a hydrophobic chemical fiber were performed. Using a polypropylene mask (Tamagawa-Eizai Co., Ltd.) as a model of hydrophobic chemical fiber, a 1 mM aqueous solution (0.05 mL) including ICG or each of the cyclodextrin-bonded indocyanine compounds of the present invention (the chemical formulae 16, 20, 21, and 23 to 25) was applied to the model, and it was washed with running water (tap water, 1 L/minute) for one second after it was allowed to stand for 20 minutes (it was allowed to stand for 20 minutes for removing moisture, because if the sample has moisture, the compound is not adhered to the mask). The results were that ICG was not completely washed out with water; whereas, the cyclodextrin-bonded indocyanine compounds of the present invention, in particular the compounds represented by the chemical formula 16 and the chemical formula 20, could be easily washed out. It was shown that the adsorption of the cyclodextrin-bonded indocyanine compound of the present invention to the hydrophobic chemical fiber was much lower than that of ICG (FIG. 5).

<Test 13: Molecule Association of Cyclodextrin-Bonded Indocyanine Compound of Present Invention in Aqueous Solution>

Figure 6:
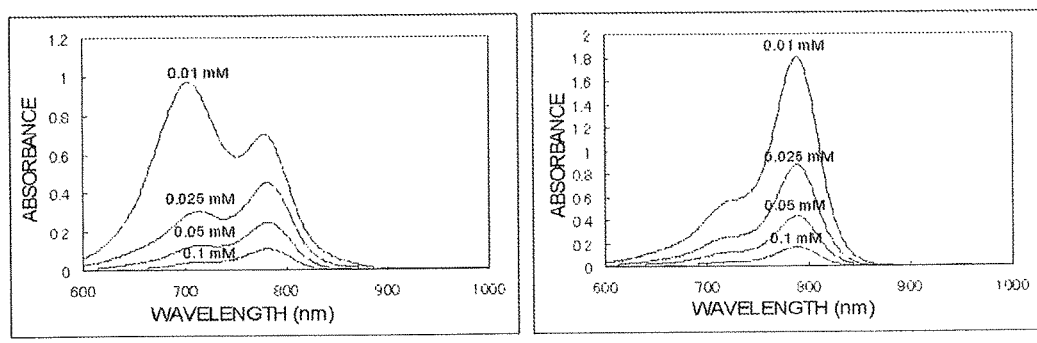
FIG. 6 shows results of molecule association tests of ICG and the isomerization equilibrium compound (TK1) represented by the chemical formula 19 or 20. A left graph shows results of ICG, and a right graph shows results of the isomerization equilibrium compound (TK1) represented by the chemical formula 19 or 20.

The molecule association of ICG and the cyclodextrin-bonded indocyanine compounds of the present invention (the chemical formulae 16, 20, 21, and 23 to 25) in an aqueous solution was studied. Each of 0.01 mM, 0.025 mM, 0.05 mM, and 0.1 mM aqueous solutions including ICG or the cyclodextrin-bonded indocyanine compound of the present invention (each chemical formula 16, 20, 21, and 23 to 25) was prepared, it was put in a quartz cell having a length of an optical path of 1 mm, and an optical absorption spectrum at 600 nm to 1000 nm was measured at 25° C. The results showed that molecule association, called as "H-aggregation," occurred for ICG in this concentration range (FIG. 6, the left graph); whereas the molecule association, called as "H-aggregation," did not occur for the cyclodextrin-bonded indocyanine compounds of the present invention, in particular, the compounds represented by the chemical formula 16 and the chemical formula 20, in this concentration range (FIG. 6, the right graph).

<Test 14: Fluorescence of Cyclodextrin-Bonded Indocyanine Compound of Present Invention in Aqueous Solution>

The fluorescence of ICG and the cyclodextrin-bonded indocyanine compounds of the present invention (the chemical formulae 16, 20, 21, and 23 to 25) in an aqueous solution was studied. A 0.1 µM aqueous solution including ICG or each of the cyclodextrin-bonded indocyanine compounds of the present invention (the chemical formulae 16, 20, 21, and 23 to 25) was put in a 1 cm square quartz cell at 25° C., which was excited with 720 nm excitation light (bandpass: 10 nm), and a fluorescence spectrum (bandpass: 10 nm) was measured. A fluorescence efficiency was calculated based on a fluorescence efficiency of ICG, 0.13 (in DMSO, at 25° C.). The results were that ICG had a fluorescence quantum efficiency of 0.021; whereas the cyclodextrin-bonded indocyanine compounds of the present invention, in particular, the compounds represented by the chemical formula 16 and the chemical formula 20 had fluorescence quantum efficiencies of 0.054 and 0.042, respectively. The fluorescence quantum efficiencies thereof were respectively 2.6-fold and 2-fold of that of ICG.

<Test 15: Fluorescence of Cyclodextrin-Bonded Indocyanine Compound of Present Invention in Blood>

The fluorescence of ICG and the cyclodextrin-bonded indocyanine compounds of the present invention (the chemical formulae 16, 20, 21, and 23 to 25) in blood was studied. ICG and the cyclodextrin-bonded indocyanine compounds of the present invention (the chemical formulae 16, 20, 21, and 23 to 25) were respectively dissolved in blood (human) in a concentration of 100 µM. The resulting blood was put in a triangular quartz cell at 25° C., which was excited with 760 nm excitation light (bandpass: 10 nm), and a surface fluorescence spectrum (bandpass: 10 nm) was measured. ICG had a fluorescence intensity of 58 (arbitrary unit) at the maximum fluorescence wavelength. The cyclodextrin-bonded indocyanine compounds of the present invention, in particular, the compounds represented by the chemical formula 16 and the chemical formula 20 had respectively fluorescence intensities of 270 (arbitrary unit) and 190 (arbitrary unit), which were 4.7-fold and 3.3-fold of that of ICG. It could be considered that this is caused because the emission of light from the cyclodextrin-bonded indocyanine compound of the present invention was not hindered in the living body.

<Test 16: Behavior of Cyclodextrin-Bonded Indocyanine Compound of Present Invention in Living Body>

The behavior of the isomerization equilibrium compound (TK1) represented by the chemical formula 19 or 20 or the isomerization equilibrium compound (TK2) represented by the chemical formula 15 or 16, which were typical examples, was evaluated in human blood and a rat body, which were living bodies of interest.

Fluorescence Behavior in Human Blood

The concentration dependence in the surface fluorescence intensity of ICG, TK1, or TK2 was evaluated in human venous blood in a triangle cell. Specifically, 1.0 mL of human venous blood was put in a triangle quartz cell, and ICG, TK1 or TK2 was added thereto in a given concentration. Excitation light of 760 nm (bandpass: 10 nm) was irradiated thereto at 25° C., and a surface fluorescence (bandpass: 10 nm) was measured. The results are shown in FIG. 7.

Figure 7:
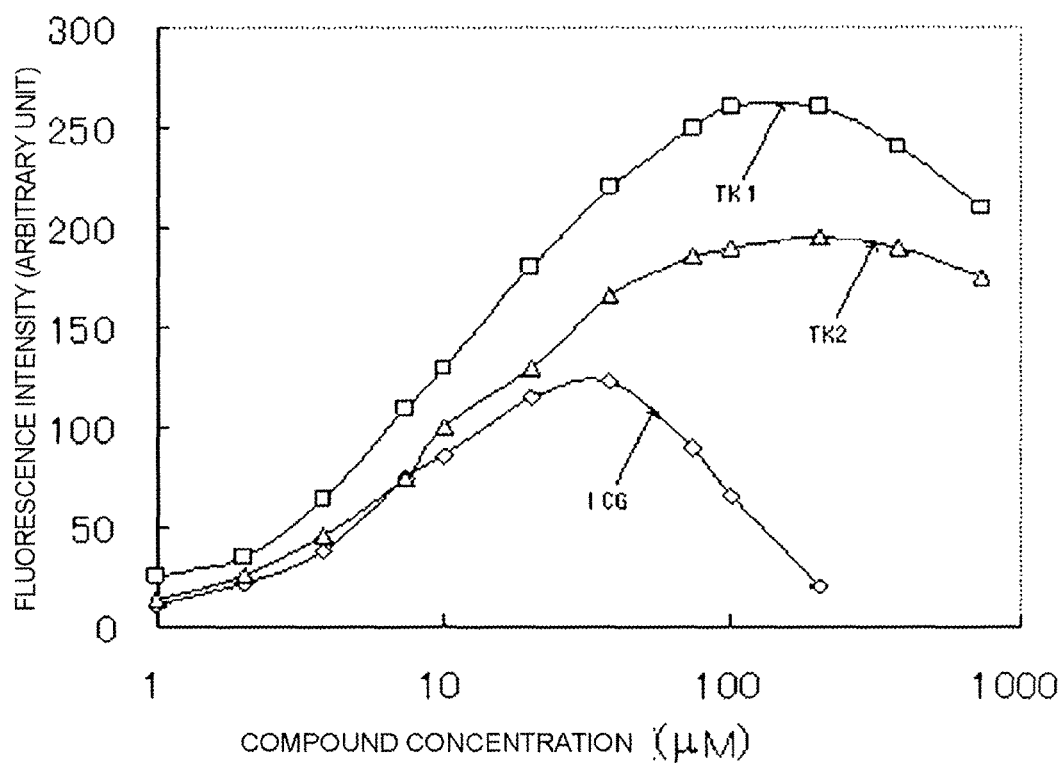
FIG. 7 is a graph showing concentration dependence of a fluorescence intensity in human venous blood of ICG, the isomerization equilibrium compound (TK1) represented by the chemical formula 19 or 20, and the isomerization equilibrium compound (TK2) represented by the chemical formula 15 or 16.

As apparent from FIG. 7, it was found that both TK1 and TK2 emitted fluorescence in the human venous blood by the irradiation of the excitation light.

Study of Possibility of Administration into Rat Body

An aqueous solution including ICG, TK1, or TK2 in a concentration of 1 mM was prepared, and 0.1 mL of the solution was injected into a femoral vein exposed in a rat which had undergone laparotomy. After that, 760 nm of excitation light was irradiated into the abdomen opened, and presence or absence of fluorescence was evaluated.

As a result, the fluorescence was observed from internal organs in the abdomen opened. It was observed that the TK1 and TK2 were highly accumulated in kidney (as already known, ICG is highly accumulated in liver). Severe influences on the rat by the administration were not observed, and it was confirmed that they could be administered relatively safely to the living body.

Observation of Distribution in Rat Body

Figure 8:
FIG. 8 is a view showing an observation state when ICG, isomerization equilibrium compound (TK1) represented by the chemical formula 19 or 20, or the isomerization equilibrium compound (TK2) represented by the chemical formula 15 or 16 is administered to a rat.
Figure 12:
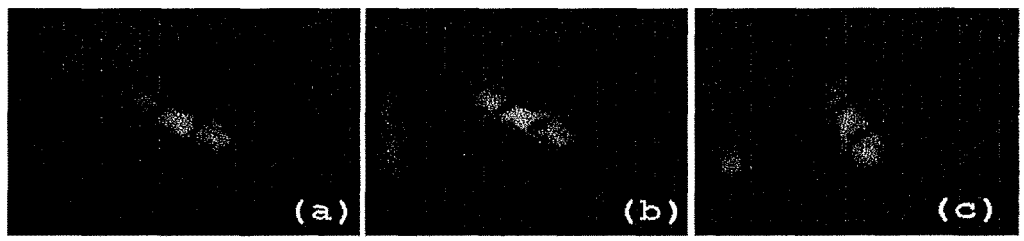
FIG. 12 shows views of fluorescence states in a dorsal region of foot when ICG (FIG. 12(a)), the isomerization equilibrium compound (TK1) represented by the chemical formula 19 or 20 (FIG. 12(b)) or the isomerization equilibrium compound (TK2) represented by the chemical formula 15 or 16 is administered to a rat (FIG. 12(c)).

After Wistar male rat (9-week old, a body weight of 350 g) was ether-anesthetized, 0.1 mL of Nembutal was intraperitoneally administered using a 26 G needle to perform the anesthesia. A base of the rat's tail was wrapped tightly with a rubber band to prevent the flow of blood, and the caudate vein was secured with a 24 G Therflow needle and a peripheral line were secured by inserting a three-way stopcock and an extension tube. The rat was fixed on a flat stand in a supine position (FIG. 8). A PDE camera unit manufactured by Hamamatsu Photonics K. K. was set at exactly 16 cm from the body of the rat. When the whole body was extensively photographed, the distance was 20 cm. The observation range was an about range shown by black dots in FIG. 8. After that, ICG, TK1 or TK2 was administered in a concentration of 1 mM from the peripheral line secured. The administration amount was 0.1 mL. After 20 minutes from the administration, the fluorescence state of the abdominal cavity which was opened is shown in FIG. 9, and the fluorescence state (images at the maximum luminance) of the dorsal region of foot was shown in FIG. 12.

Figure 9:
FIG. 9 shows views showing fluorescence states in an abdominal cavity when ICG, the isomerization equilibrium compound (TK1) represented by the chemical formula 19 or 20, or the isomerization equilibrium compound (TK2) represented by the chemical formula 15 or 16 is administered to a rat.
Figure 10:
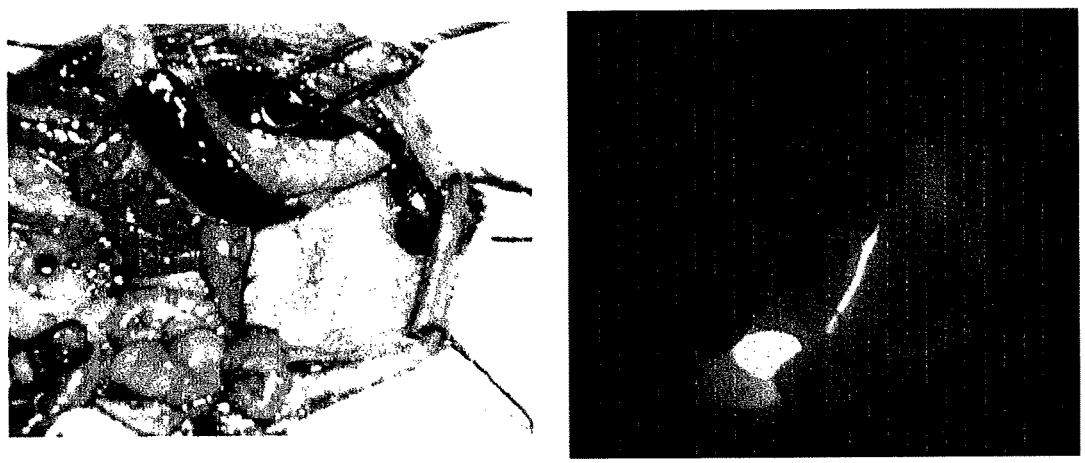
FIG. 10 shows views obtained by administrating a 0.1 mM aqueous solution (0.075 mL) including the isomerization equilibrium compound (TK2) represented by the chemical formula 15 or 16 to a caudate vein of a male Wistar rat (14-week old, 300 g), and taking an image thereof by using a near-infrared observation system PDE manufactured by Hamamatsu Photonics K. K. Left is a monochrome image through visible light, and right is a fluorescence image.
Figure 11:
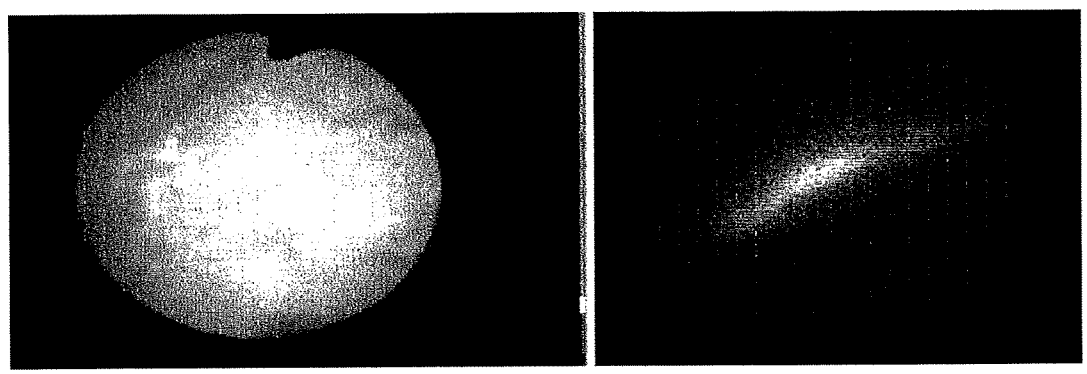
FIG. 11 shows views obtained by administrating a 0.1 mM aqueous solution (0.075 mL) including the isomerization equilibrium compound (TK2) represented by the chemical formula 15 or 16 to a caudate vein of a male Wistar rat (14-week old, 300 g), and taking an image thereof by using a near-infrared fluorescent endoscope. Left is a monochrome image through visible light, and right is a fluorescence image.

FIG. 9 shows that ICG was mainly accumulated in the liver (FIG. 9 (a)), and TK1 and TK2 were mainly accumulated in the kidney (FIG. 9 (b) and FIG. 9 (C)). The near-infrared imaging of the internal organs immediately after the administration showed that the kidney, ureter and bladder were clearly imaged (FIG. 10). In addition, it also shown that the ureter could be imaged by the near-infrared endoscope (FIG. 11).

As apparent from the image view 12, the state in which the fluorescence was emitted in accordance with the blood flow was clear in the dorsal region of foot. It was also found that when ICG, TK1 or TK2 was administered as above and fluorescence was observed in an ischemia model of a lower limbs which was caused by ligation of a right femoral artery of a rat, the fluorescence was not observed in the ischemia area, and therefore it was found that a degree of blood flow could be evaluated based on the presence or absence of the fluorescence, though it was not shown in a figure.

Figure 13:
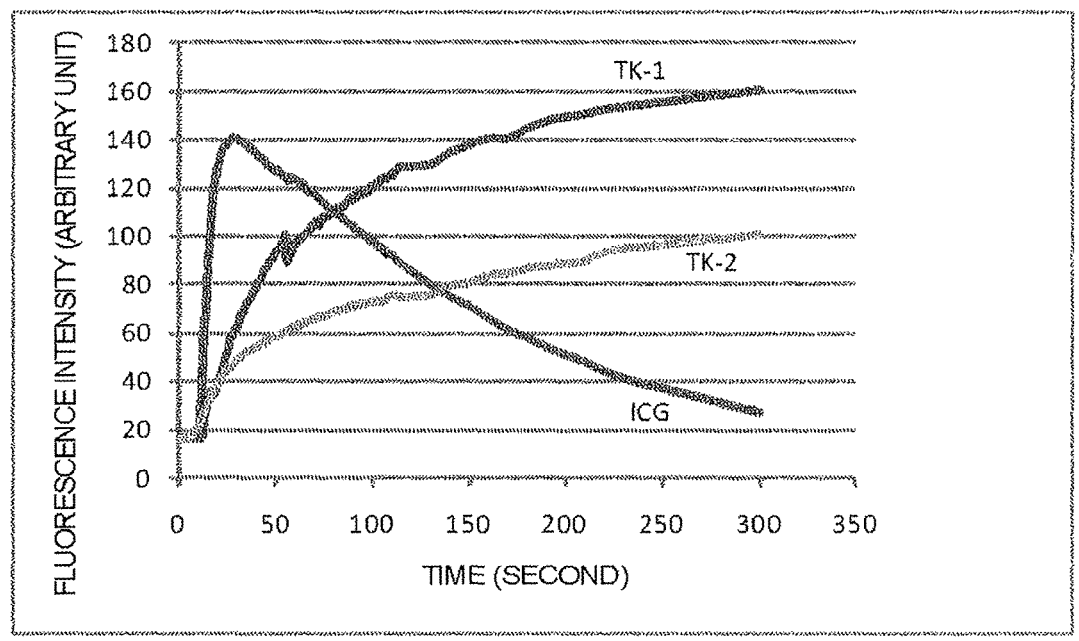
FIG. 13 is a graph showing changes with time in the fluorescence intensity in a dorsal region of foot when ICG, the isomerization equilibrium compound (TK1) represented by the chemical formula 19 or 20, or the isomerization equilibrium compound (TK2) represented by the chemical formula 15 or 16 is administered to a rat.
Figure 14:
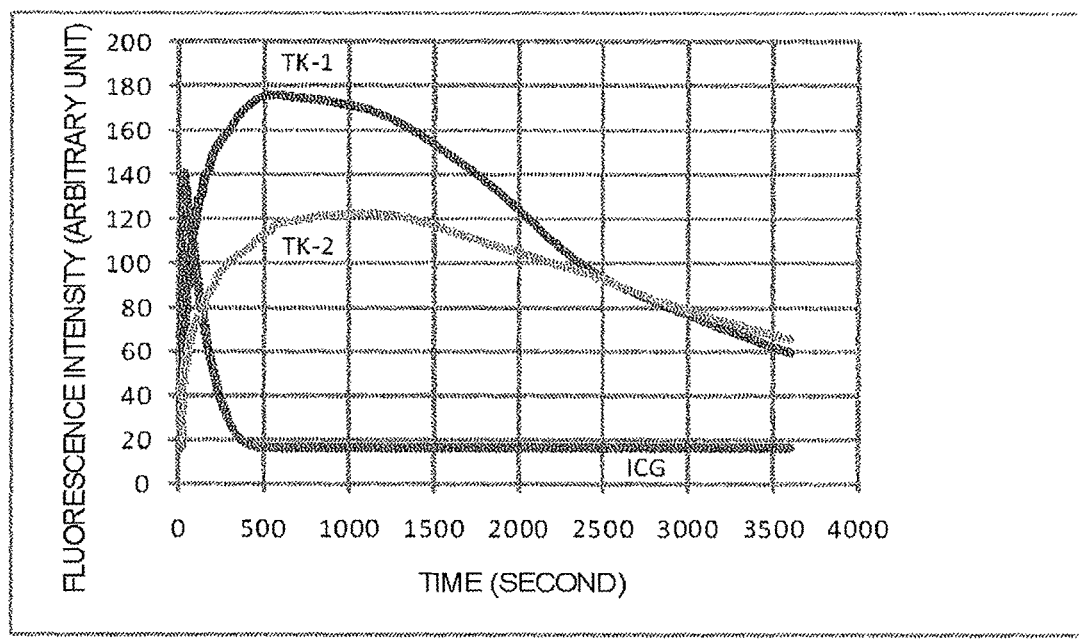
FIG. 14 is a graph showing changes with time in the fluorescence intensity in a dorsal region of foot when ICG, the isomerization equilibrium compound (TK1) represented by the chemical formula 19 or 20, or the isomerization equilibrium compound (TK2) represented by the chemical formula 15 or 16 is administered to a rat.

Here, the changes with time in the fluorescence intensity of the dorsal region of foot were shown in FIG. 13 and FIG. 14. In addition, a time reaching the maximum fluorescence intensity value (Imax), Imax value and a time at which the value reached a half of the Imax value (t½) are shown in Table 1.

TABLE 1

| Compound | Time for $I_{max}$ | $I_{max}$* | $t_{1/2}$ |
|---|---|---|---|
| ICG | 0.5 min | 124 | 2.3 min |
| TK-1 | 10 min | 160 | 40 min |
| TK-2 | 15 min | 106 | 55 min |

As apparent from Table 1, FIG. 13 and FIG. 14, it was found that the times necessary for reaching the maximum fluorescence intensity value and the times necessary for reducing it by half of TK1 and TK2 were longer than those of ICG, in other words, they could emit the fluorescence for a long time in the body. It was found that, for example, the fluorescence intensity of ICG was reduced to an about initial value thereof in less than 10 minutes after the administration; whereas, TK1 and TK2 showed a high fluorescence intensity even after one hour from the administration.

Observation at Blood Vessel Level

Figure 15:
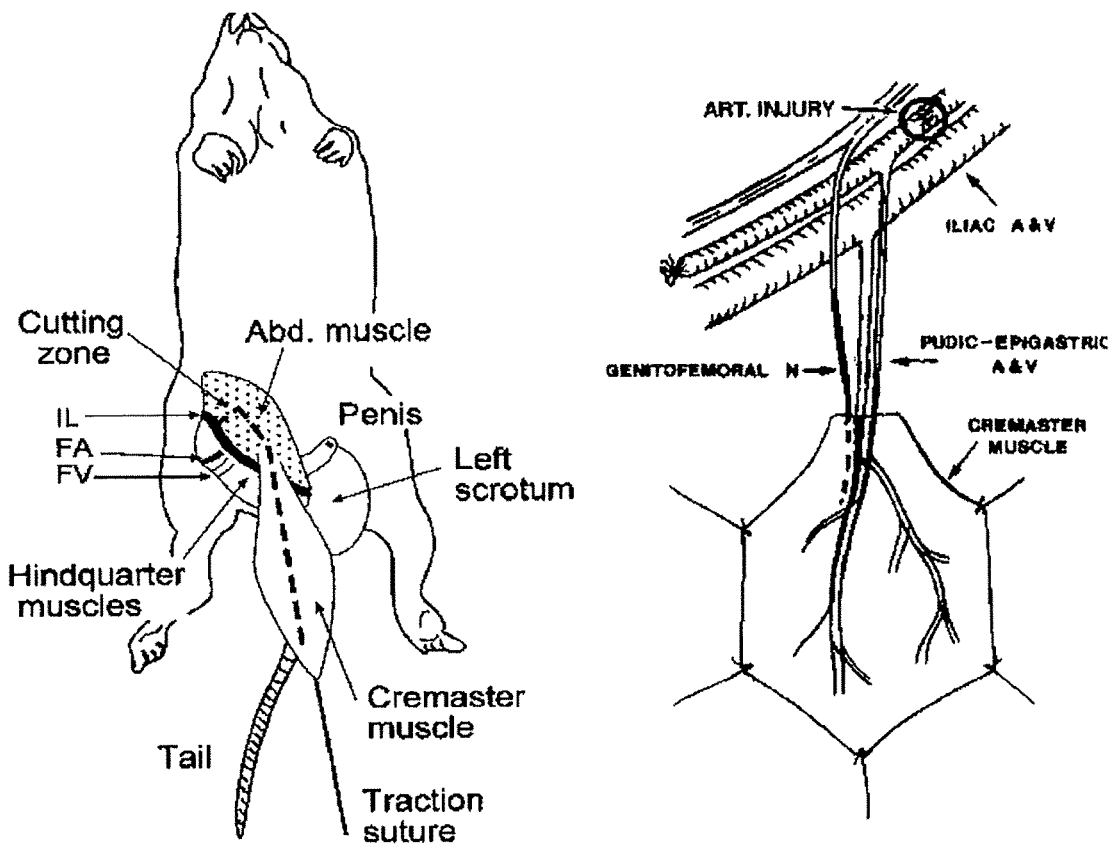
FIG. 15 is an illustration showing a procedure for directly observing a blood vessel of a rat.
Figure 16:
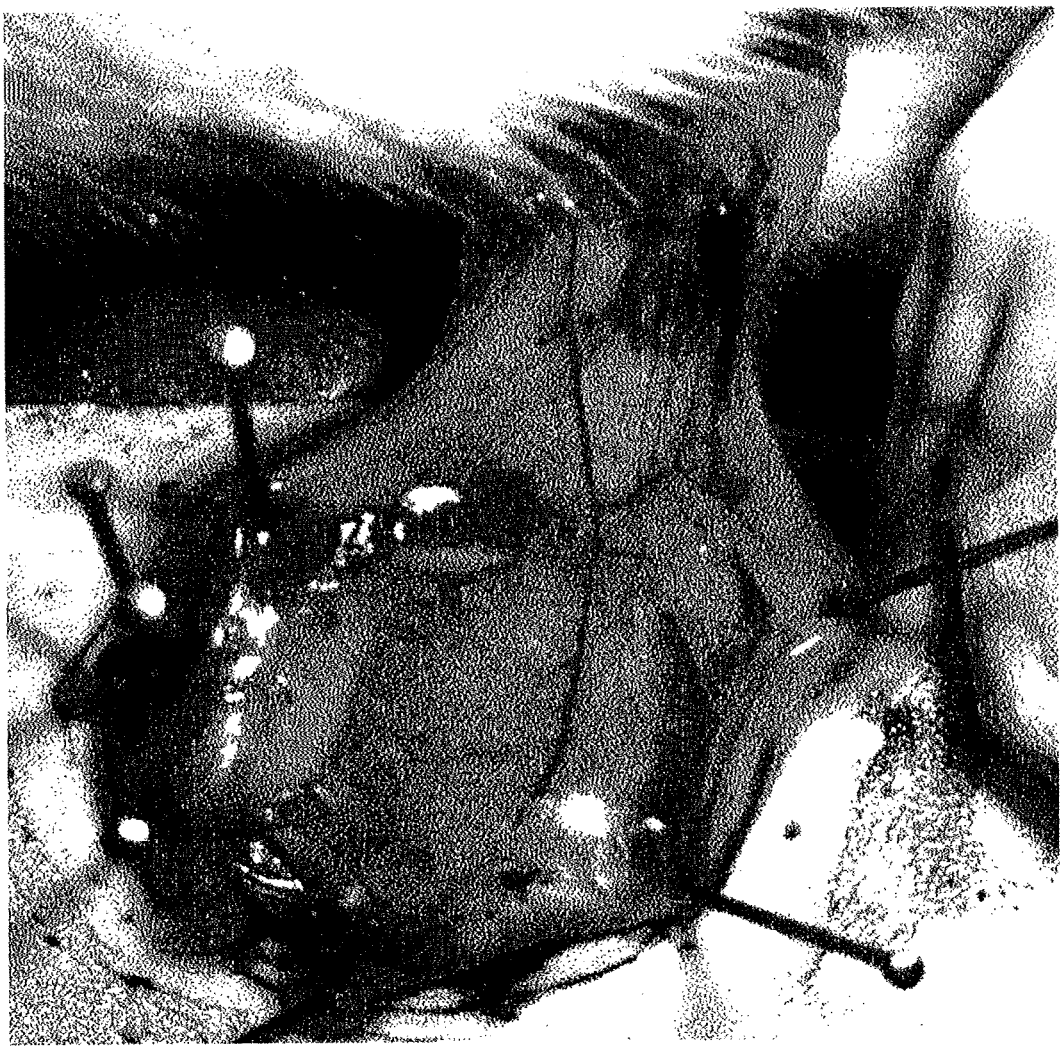
FIG. 16 is a view showing an area (cremaster skin flap) directly observed in a blood vessel of a rat.
Figure 17:
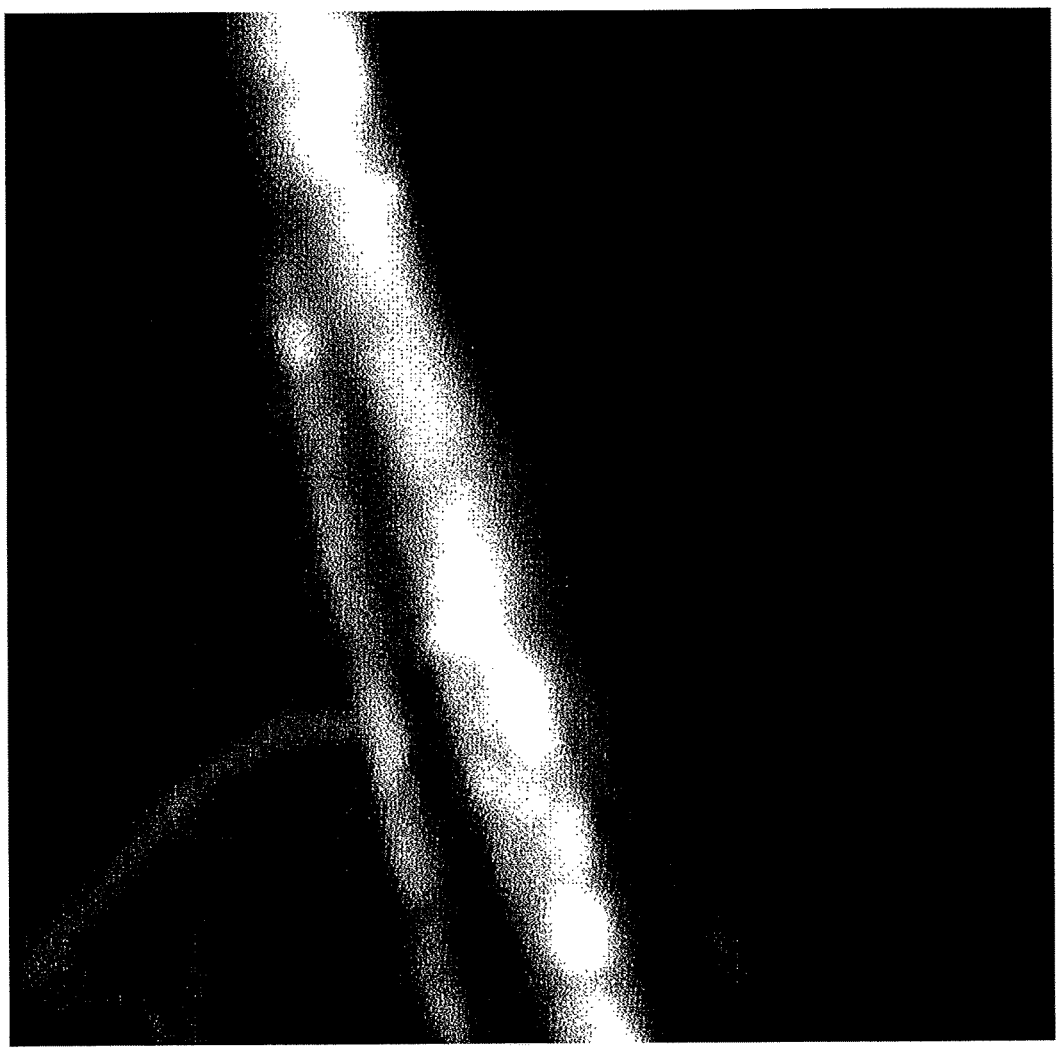
FIG. 17 is a view showing fluorescence states of a blood vessel of a rat to which ICG is administered and tissues around it.
Figure 18:
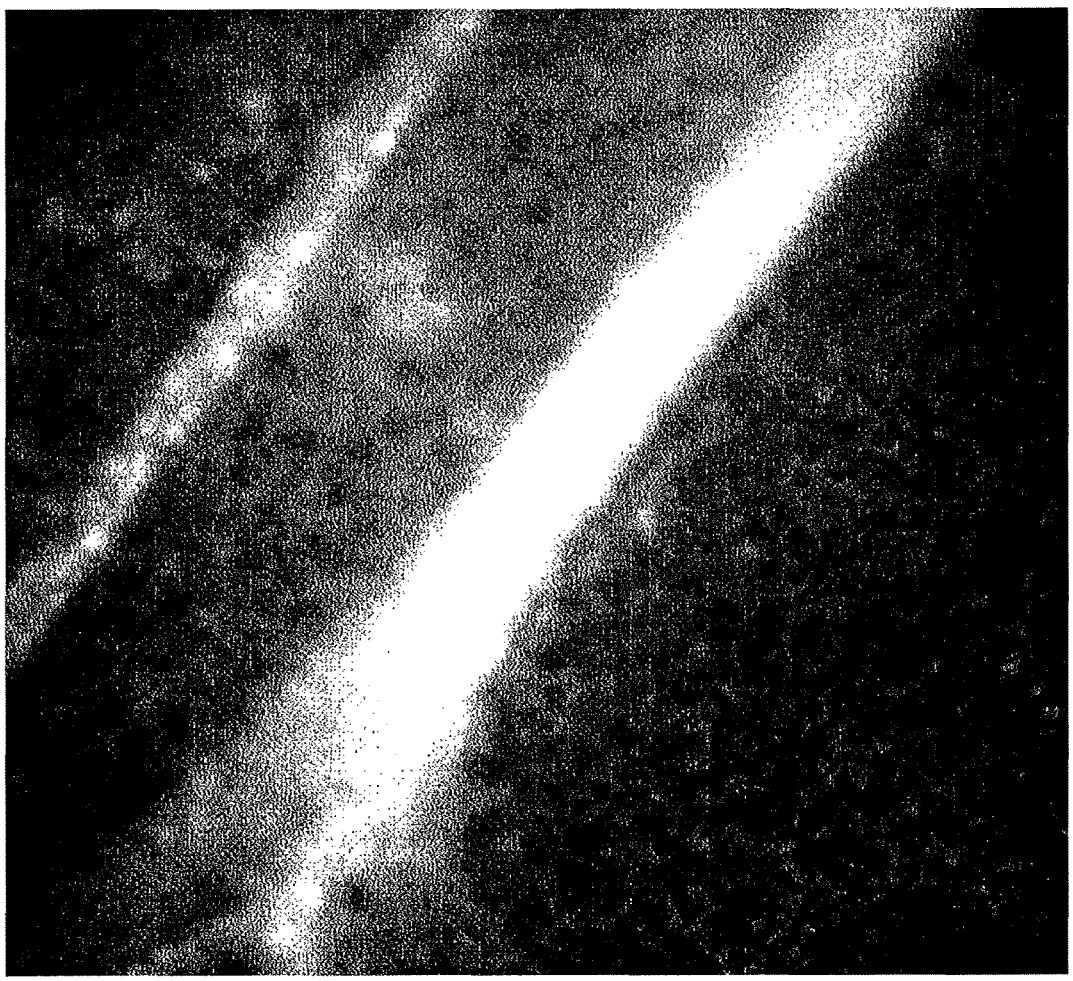
FIG. 18 is a view showing fluorescence states of a blood vessel of a rat to which the isomerization equilibrium compound (TK1) represented by the chemical formula 19 or 20 is administered and tissues around it.

ICG or TK1 was administered in a state in which a blood vessel of a rat was directly exposed and observed by methods disclosed in Non Patent Documents 7 and 8 (FIG. 15), and a state of a cremaster skin flap after the exposure is shown in FIG. 16. ICG or TK1 was administered in the state in which the blood vessel was exposed, and the observation was performed. As a result, it was observed that ICG was unevenly distributed in the blood vessel, compared to TK1. It was found therefore that TK1 transferred from the blood vessel into the interstitial tissue fluid. In order to more precisely study it, photomicrographs of the blood vessel after the administration are shown in FIG. 17 (ICG) and FIG. 18 (TK1). As apparent from FIGS. 17 and 18, in comparison of them in the fluorescence intensity in the blood vessel and the fluorescence intensity in the surrounding tissues thereof, the fluorescence was hardly observed in the interstitial tissue for ICG; whereas the fluorescence was observed in the interstitial tissue for TK1, and the increase of the fluorescence intensity with time was also observed in the interstitial tissue, though it is not described in detail. It was found therefore that ICG hardly transferred from the blood vessel into the interstitial tissue fluid; whereas TK1 transferred from the blood vessel into the interstitial tissue fluid.

Evaluation of Relationship Between Degree of Transfer of Cyclodextrin-Bonded Indocyanine Compound of Present Invention into Interstitial Tissue and Size of Edema Formed (Evaluation Method)

Rats (male, Wister rat) which were 10-week old and about 350 g were selected as a test animal (n=4). The rat was generally anesthetized with isoflurane, and 0.1 mL of 0.5% λ-carrageenin was injected to a left posterior footpad using a 26 G needle, thus resulting quick generation of edema on the foot. After 15 minutes, a volume of the left foot of the rat was measured using a rat footpad volume-measuring device (MK-101 CMP PLETHYSMOMETER manufactured by Muromachi Kikai Co., Ltd.).

After that, the isoflurane was off and the emergence of the rat was confirmed. After Von Frey test was performed, the rat was generally anesthetized with isoflurane again. The caudate vein of the rat was secured with a 24 G Therflow needle, and then it was fixed on a horizontal stand in a supine position. A PDE camera manufactured by Hamamatsu Photonics K. K. was set and fixed at a height of 16 cm from a *dorsalis pedis* of the rat.

A moiety (ROI) to be measured by the PDE camera was set at a central part of the *dorsalis pedis* and light was turned off. After the measurement was started, 0.1 mL of an aqueous solution including 1 mmol TK1 was infused from a caudate vein, and 1 mL of physiological saline was flushed over 5 seconds. A continuous imaging was performed for initial 5 minutes after the infusion to measure luminances in the ROI. After that, luminance was measured for one minute at 5 minute-intervals and the measurement was continued until 120 minutes from the infusion. After the measurement was finished, the isoflurane was off to bring the rat out of the anesthesia, and it was returned into a cage (acute inflammation experiment).

After 7 days, a Von Frey test was performed and then the rat was quickly generally anesthetized with isoflurane, and the volume of the left foot of the rat was measured by using the rat footpad volume-measuring device. The caudate vein of the rat was secured with a 24 G Therflow needle, and then it was fixed on a horizontal stand in a supine position. A PDE camera manufactured by Hamamatsu Photonics K. K. was set and fixed at a height of 16 cm from the *dorsalis pedis* of the rat. After the ROI was set at the central part of the *dorsalis pedis* and light was turned off, the measurement was started. An aqueous solution including 1 mmol TK1, 0.1 mL, was infused from a caudate vein, and 1 mL of physiological saline was flushed over 5 seconds. A continuous imaging was performed for initial 5 minutes after the infusion to measure luminances in the ROI. After that, luminance was measured for one minute at 5 minute-intervals and the measurement was continued until 120 minutes from the infusion. After the measurement was finished, the isoflurane was off to bring the rat out of the anesthesia, and it was returned into the cage. A group to which λ-carrageenin was not injected was subjected to the same test.

The same procedures as above were performed for ICG.

(Results)

Figure 19:
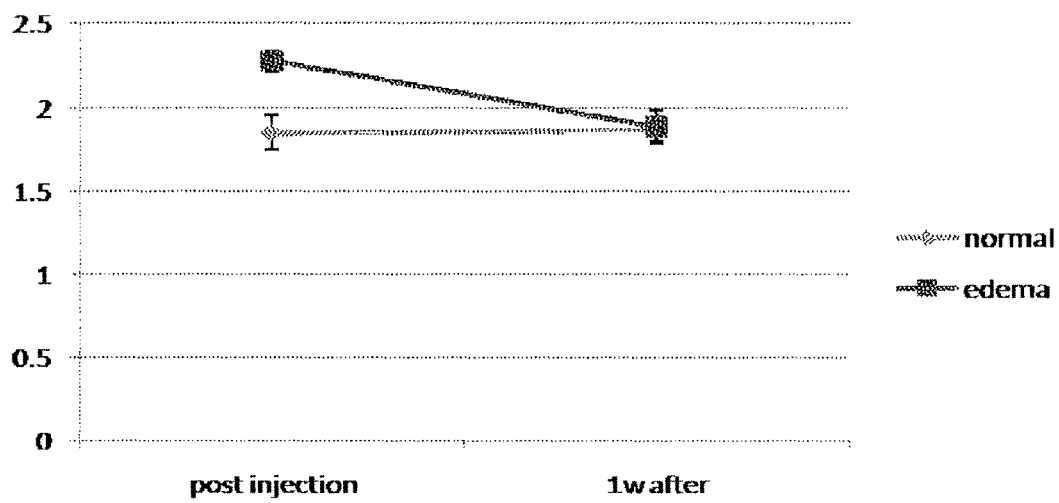
FIG. 19 is a graph showing volumes of a left foot of a rat measured immediately after an administration (post injection) and at one week after the administration (1 w after) in a group in which carrageenin administration is performed (edema) and a group in which the administration is not performed (normal) in experiment groups using TK1, wherein a vertical axis shows a volume (mL).
Figure 20:
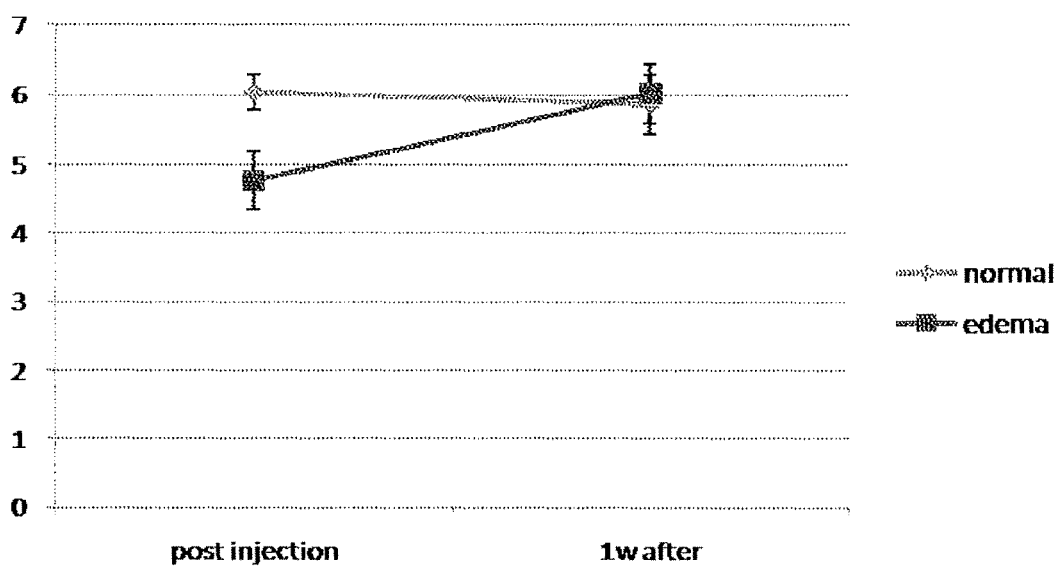
FIG. 20 is a graph showing results of Von Frey tests of a left foot of a rat measured immediately after an administration (post injection) and at one week after the administration (1 w after) in a group in which carrageenin administration is performed (edema) and a group in which the administration is not performed (normal) in experiment groups using TK1, wherein a vertical axis shows a load (g) when a response is obtained.
Figure 21:
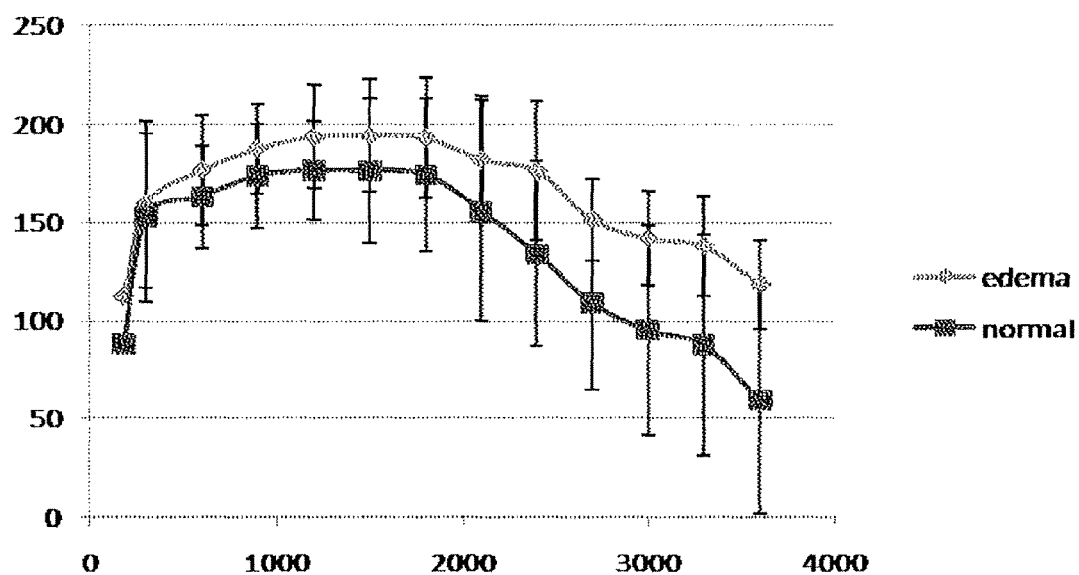
FIG. 21 is a graph showing changes in a luminance of a left foot surface after TK1 was injected immediately after injection of carrageenin in a group in which the carrageenin administration is performed (edema) and a group in which the administration is not performed (normal), wherein a vertical axis shows a luminance (arbitrary unit) and a horizontal axis shows a time (second).
Figure 22:
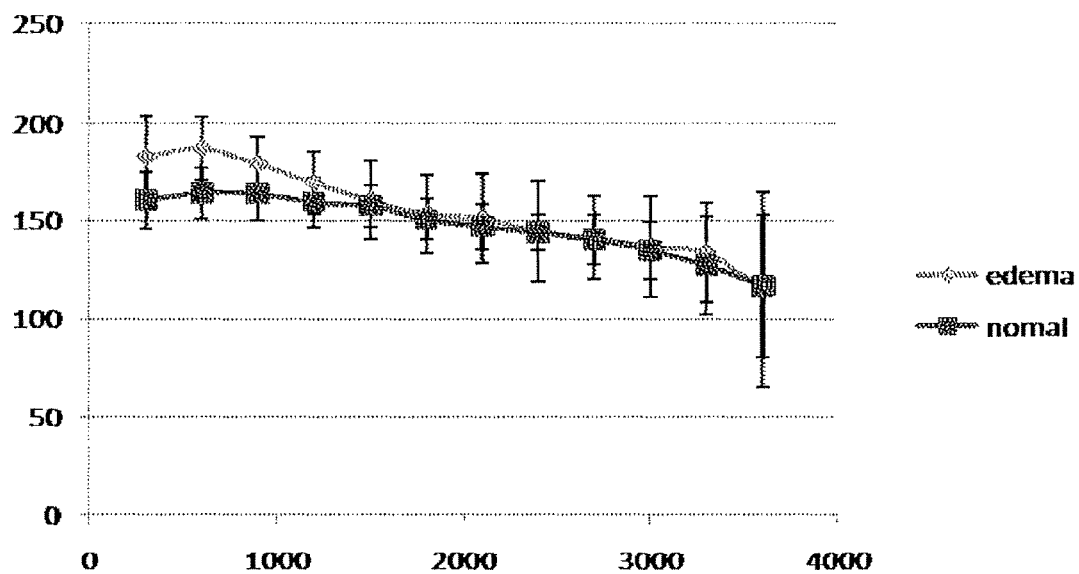
FIG. 22 is a graph showing changes in a luminance of a left foot surface after TK1 was injected one week after injection of carrageenin in a group in which the carrageenin administration is performed (edema) and a group in which the administration is not performed (normal), wherein a vertical axis shows a luminance (arbitrary unit) and a horizontal axis shows a time (second).
Figure 23:
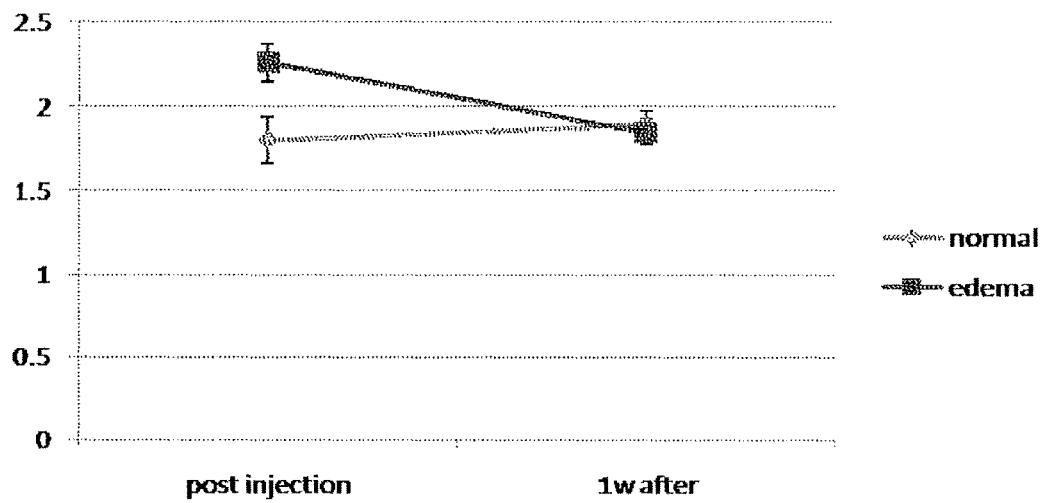
FIG. 23 is a graph showing volumes of a left foot of a rat measured immediately after an administration (post injection) and at one week after the administration (1 w after) in a group in which carrageenin administration is performed (edema) and a group in which the administration is not performed (normal) in experiment groups using ICG, wherein a vertical axis shows a volume (mL).
Figure 24:
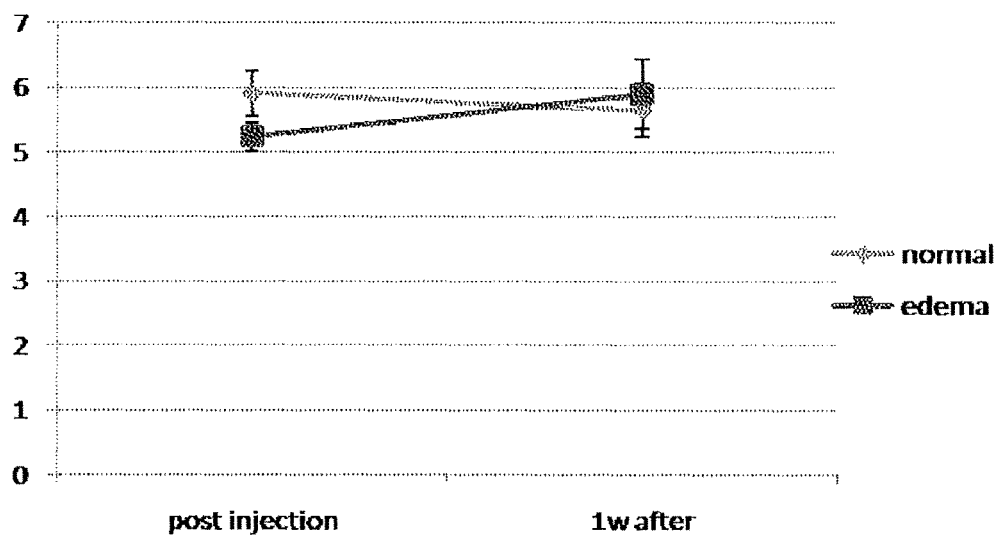
FIG. 24 is a graph showing results of Von Frey tests of a left foot of a rat measured immediately after an administration (post injection) and at one week after the administration (1 w after) in a group in which carrageenin administration is performed (edema) and a group in which the administration is not performed (normal) in experiment groups using ICG, wherein a vertical axis shows a load (g) when a response is obtained.
Figure 25:
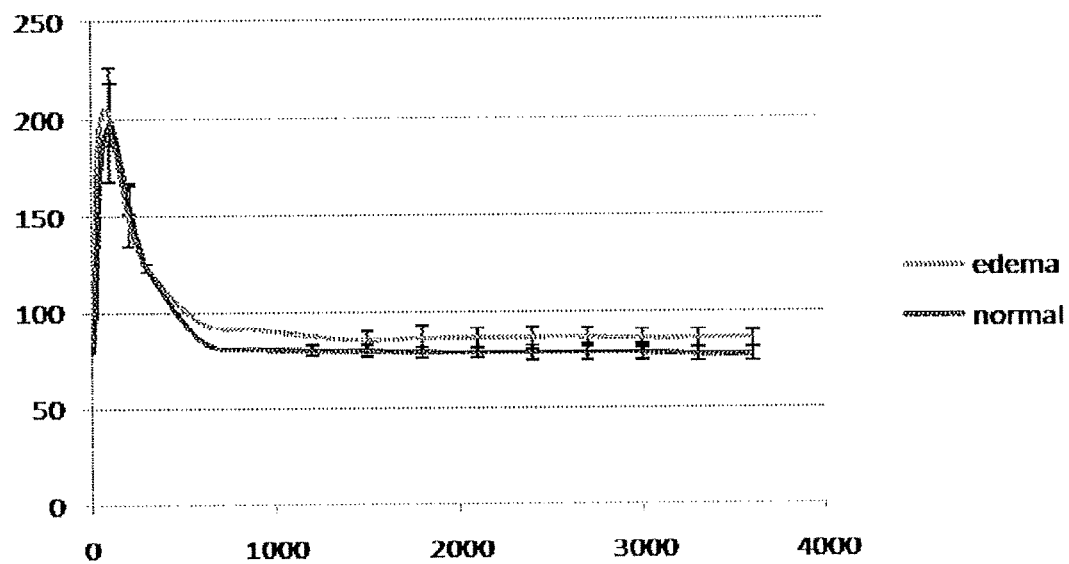
FIG. 25 is a graph showing changes in a luminance of a left foot surface after ICG was injected immediately after injection of carrageenin in a group in which carrageenin administration is performed (edema) and a group in which the administration is not performed (normal), wherein a vertical axis shows a luminance (arbitrary unit) and a horizontal axis shows a time (second).
Figure 26:
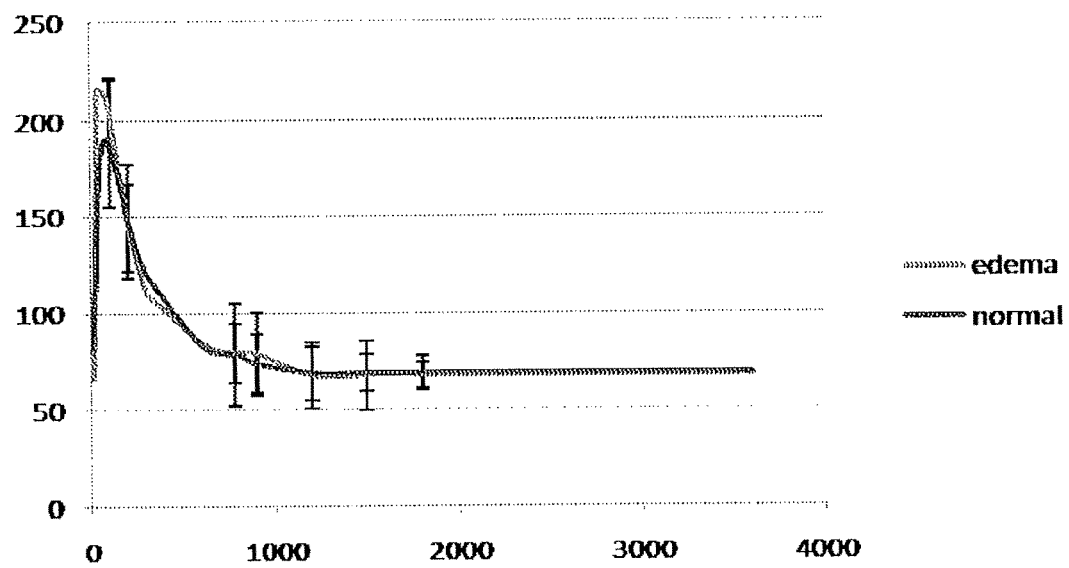
FIG. 26 is a graph showing changes in a luminance of a left foot surface after ICG was injected one week after injection of carrageenin in a group in which carrageenin administration is performed (edema) and a group in which the administration is not performed (normal), wherein a vertical axis shows a luminance (arbitrary unit) and a horizontal axis shows a time (second).

The results are shown in FIGS. 19 to 26. The volume of the left foot of the rat in the group to which TK1 was administered are shown in FIG. 19 (the higher the vertical axis, the larger the volume); the results of the Von Frey test are shown in FIG. 20 (the lower the vertical axis, the higher the hyperalgesia); the change in the luminance immediately after the injection is shown in FIG. 21 (the higher the vertical axis, the higher the luminance); and the change in the luminance after one week from the carrageenin injection is shown in FIG. 23 (the higher the vertical axis, the higher the luminance). The volume of the left foot of the rat in the group to which ICG was administered is shown in FIG. 23 (the higher the vertical axis, the larger the volume); the results of the Von Frey test are shown in FIG. 24 (the lower the vertical axis, the higher the hyperalgesia); the change in the luminance immediately after the injection is shown in FIG. 25 (the higher the vertical axis, the higher the luminance); and the change in the luminance after one week from the carrageenin injection is shown in FIG. 26 (the higher the vertical axis, the higher the luminance). The values on the vertical axes in all of the graphs are arbitrary units.

A large difference was observed between ICG and TK1 in the change pattern in luminance in the ROI. The luminance was increased in a short time after the administration of ICG, and then it was quickly turned into decrease and decreased to the base line in about 10 minutes. On the other hand, the TK1 showed the similar trajectory to that of ICG in the increase of the luminance in the early state after the administration, but after that the luminance was stopped at a high level, and it took 6 hours to return to the base line. From these results, it was considered that ICG stayed in the blood vessel without leakage into the interstitial tissue, and the passage in the blood vessel distributed in ROI caused the quick increase of the luminance and the subsequent quick decrease thereof. On the other hand, it could be considered that TK1 reflected two phases of a part in which the quick passage in the blood vessel at the first stage was reflected (hereinafter referred to as a "blood vessel phase") and a phase in which TK1, which gradually leaked to the interstitial tissue after that, emitted the fluorescence (hereinafter referred to as an "interstitial tissue phase"). A time necessary for transfer from the blood vessel phase to the interstitial tissue phase corresponds to a predetermined time.

In the acute inflammation experiment, the remarkable increase of the foot volume of the rat was observed after the λ-carrageenin injection in both TK1 and ICG groups, and the volume was normalized to that at a tendon side after one week (FIGS. 19 and 23). In the Von Frey test, the remarkable hyperalgesia was observed after the λ-carrageenin injection in both TK1 and ICG groups, and the hyperalgesia was normalized to that at the tendon side after one week (FIGS. 20 and 24).

It was observed that in the luminance of the *dorsalis pedis*, the luminance change in the TK1 group was not different from that of the control group in the blood vessel phase, but the faster luminance increase in the λ-carrageenin administration group was observed in the interstitial tissue phase, and it was observed TK1 group maintained high values during the evaluation time (FIG. 21). After one week from the λ-carrageenin administration, at which the inflammation caused by the administration disappeared, difference in the luminance change was not observed between the carrageenin administration side and the tendon side in the interstitial tissue phase (FIG. 22). As clearly shown in the graph of FIG. 21, the change in the luminance showed a smooth curve in the interstitial tissue phase, and it was found that the height of the peak depended on a rate of change of rising in the interstitial tissue phase, in other words, it shows that a change of values in the interstitial tissue phase can be predicted in a high precision by a time series analysis, and shows important grounds for proving our working hypothesis.

In ICG group, the difference in the luminance was not observed between the immediately after the λ-carrageenin injection and after one week from the administration (FIG. 25 and FIG. 26). From this result, it was found that ICG, which is highly hydrophobic and has hitherto been clinically used, did not cause the leakage of the fluorescence substance out of the blood vessel, even if there was a severe acute inflammation caused by, for example, λ-carrageenin.

From the results described above, it became apparent that when the fluorescence intensity of the moiety in which tumescence progression is predicted is measured with time during a term corresponding to the interstitial tissue phase after TK1 was administered to a living body, the change in the subsequent fluorescence intensity can be predicted, and the change in the fluorescence intensity is relevant to the tumescence progression in that moiety. It can be found accordingly that TK1 can be used in the prediction of tumescence which cannot be predicted by using ICG.

INDUSTRIAL APPLICABILITY

According to the cyclodextrin-bonded indocyanine compound represented by the chemical formula 1 or chemical formula 2 of the present invention, a compound which is a green pigment and emits near-infrared fluorescence, which characterized by having a higher solubility in water or physiological saline, easier removal from biological tissues, lower molecule association in an aqueous solution, and higher near-infrared fluorescence intensity in an aqueous solution compared to ICG, and including no iodine can be provided. Also according to the synthesis method of the cyclodextrin-bonded indocyanine compound of the present invention, a useful synthesis of the cyclodextrin-bonded indocyanine compound can be provided. Further according to the purification method of the cyclodextrin-bonded indocyanine compound of the present invention, a useful purification of the cyclodextrin-bonded indocyanine compound can be provided. Furthermore, the cyclodextrin-bonded indocyanine compound of the present invention can provide a diagnostic composition including no iodine which causes iodine hypersensitivity, because the compound shows a sufficient solubility even if the iodine is not included. The diagnostic composition shows a biobehavior different from that of a conventional diagnostic composition including ICG alone, and thus various useful diagnosis methods and diagnosis devices can be provided utilizing the properties.

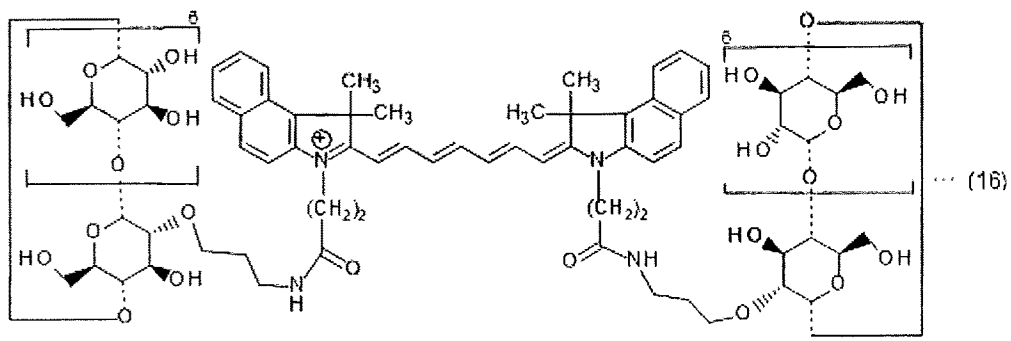

The invention claimed is:
1. A solid cyclodextrin-bonded indocyanine of formula (16):

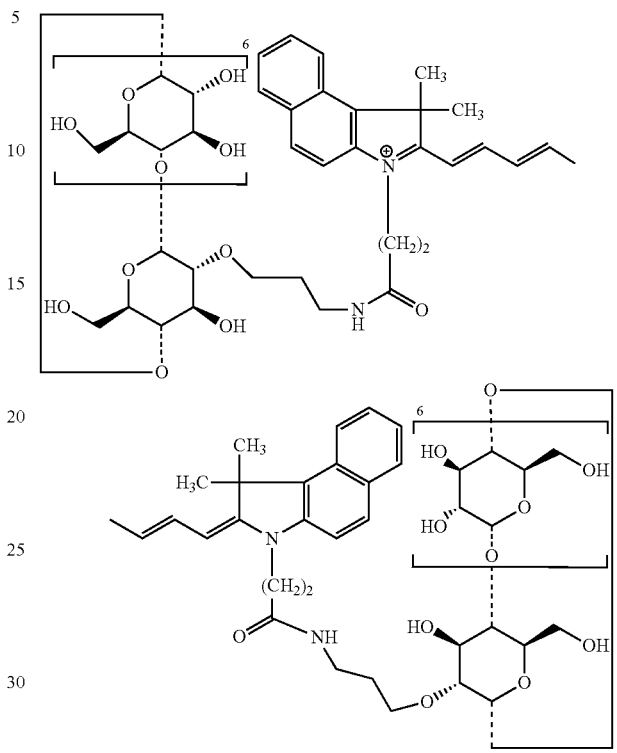

wherein:
at least a portion of a naphthyl group of the indocyanine is included in a cavity of the cyclodextrin; and
the indocyanine has a counter anion.
2. A composition, comprising the solid cyclodextrin-bonded indocyanine of claim 1.
3. The solid cyclodextrin-bonded indocyanine of claim 1, wherein the counter anion is a chloride anion.
4. A composition, comprising the solid cyclodextrin-bonded indocyanine of claim 3.
5. A solid cyclodextrin-bonded indocyanine of formula (20):

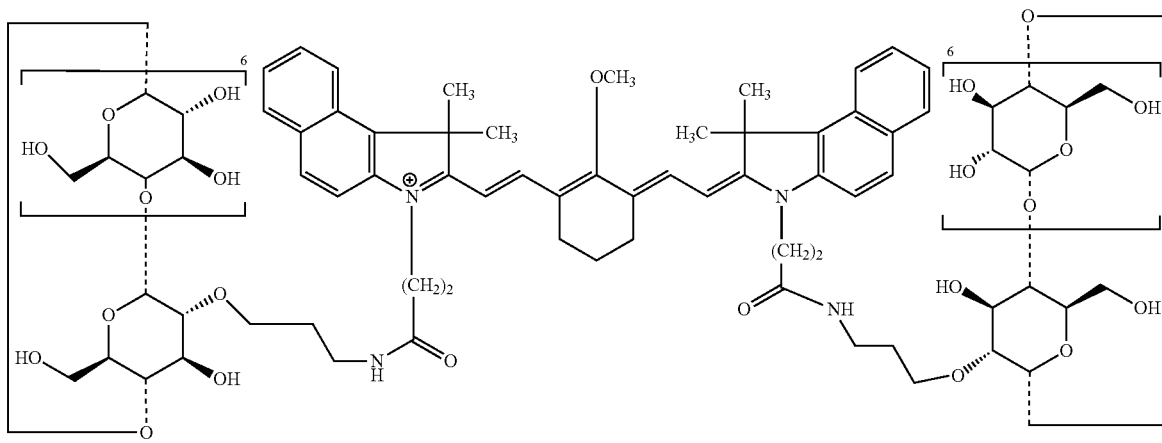

wherein:
   at least a portion of a naphthyl group of the indocyanine is included in a cavity of the cyclodextrin; and
   the indocyanine has a counter anion.

6. A composition, comprising the solid cyclodextrin-bonded indocyanine of claim 5.

7. The solid cyclodextrin-bonded indocyanine of claim 5, wherein the counter anion is a chloride anion.

8. A composition, comprising the solid cyclodextrin-bonded indocyanine of claim 7.

* * * * *

UNITED STATES PATENT AND TRADEMARK OFFICE
CERTIFICATE OF CORRECTION

PATENT NO. : 10,350,310 B2
APPLICATION NO. : 16/101544
DATED : July 16, 2019
INVENTOR(S) : Katsunori Teranishi et al.

Page 1 of 9

It is certified that error appears in the above-identified patent and that said Letters Patent is hereby corrected as shown below:

In the Specification

Columns 9 and 10, Line 13, Formula (6):

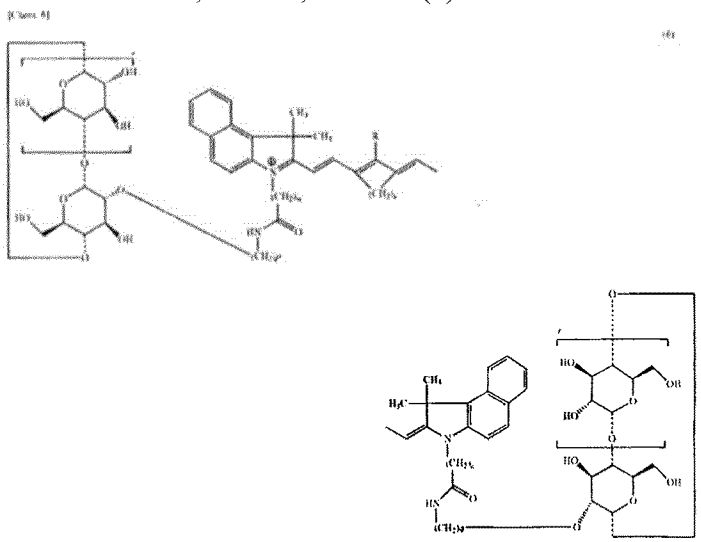

Should read as one formula:

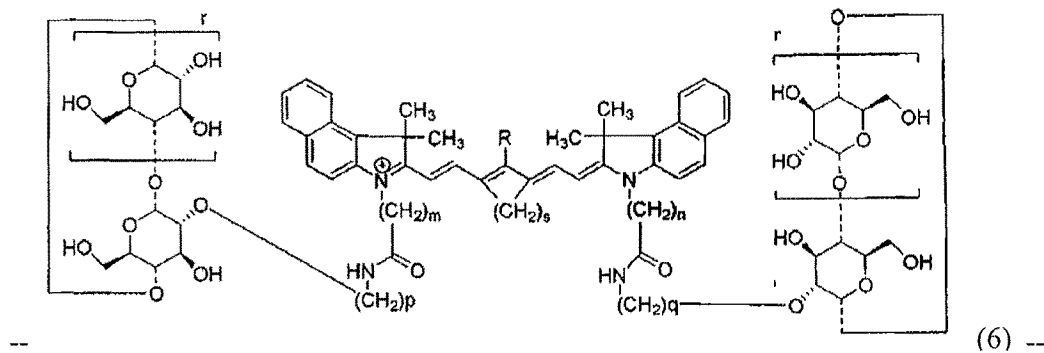

(6) --

Signed and Sealed this
Third Day of December, 2019

Andrei Iancu
*Director of the United States Patent and Trademark Office*

CERTIFICATE OF CORRECTION (continued)
U.S. Pat. No. 10,350,310 B2

Columns 11 to 14, Line 36, Formula (8):

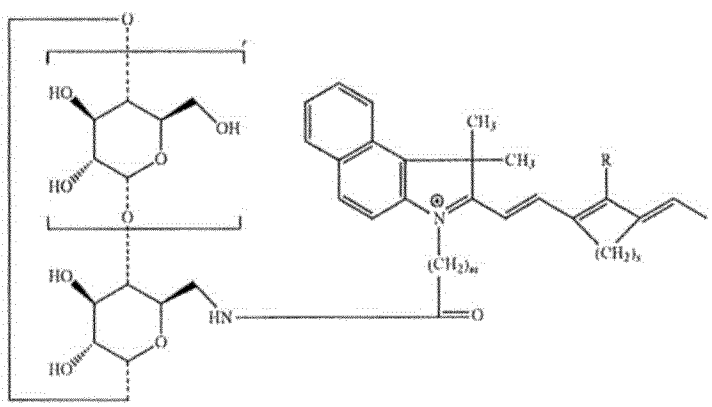

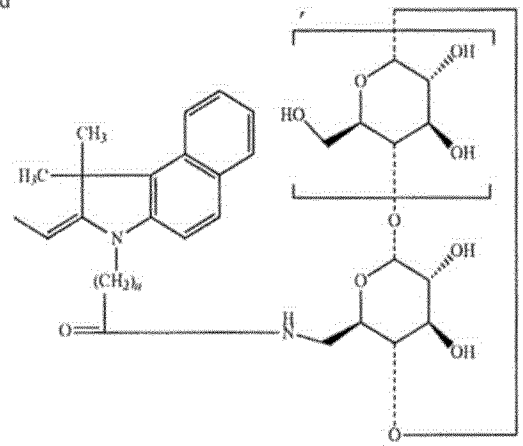

Should read as one formula:

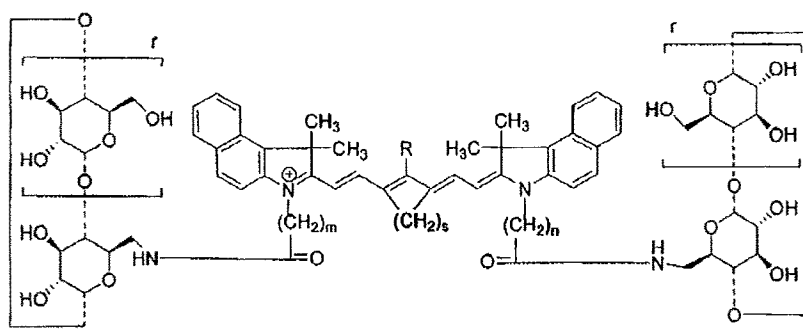

Columns 15 and 16, Line 1, Formula (10):
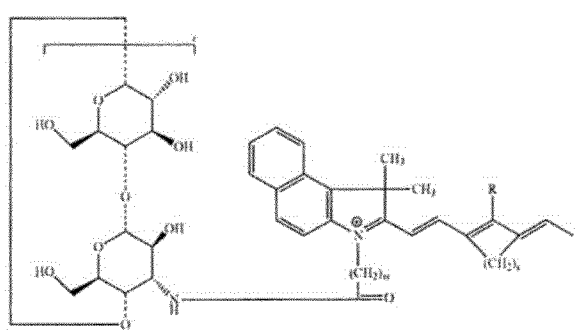
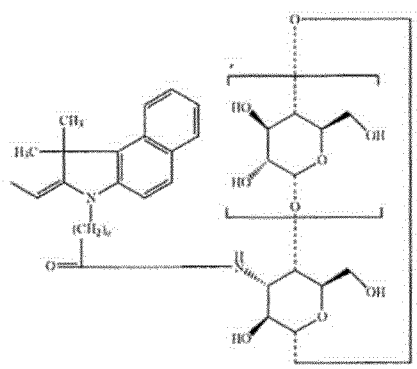
Should read as one formula:
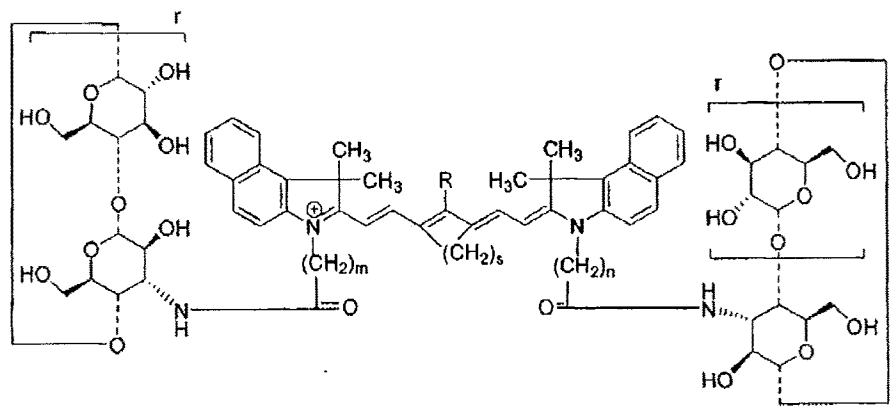

CERTIFICATE OF CORRECTION (continued)
U.S. Pat. No. 10,350,310 B2

Page 4 of 9

Columns 37 and 38, Line 38, Formula (15):

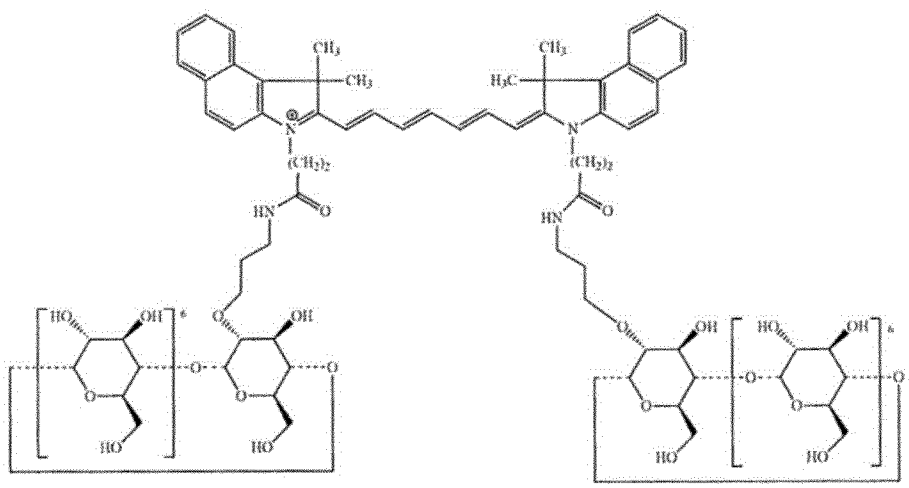

Should read:

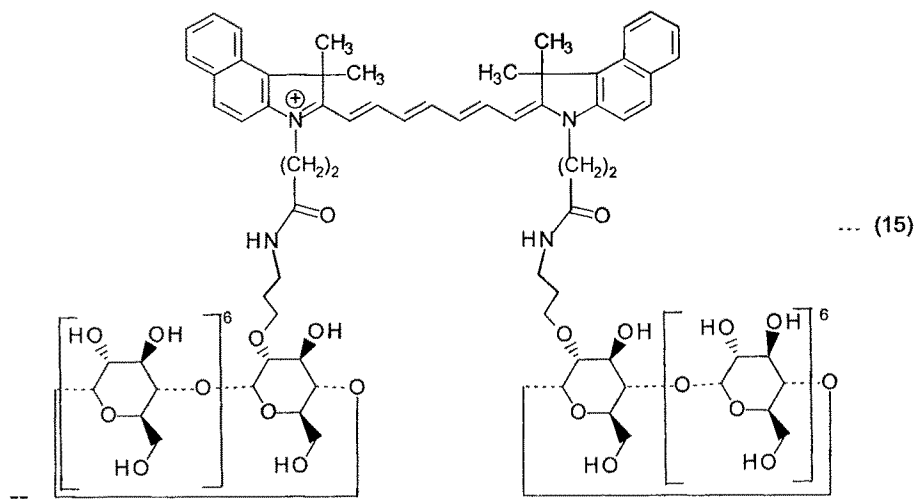

CERTIFICATE OF CORRECTION (continued)
U.S. Pat. No. 10,350,310 B2

Columns 41 and 42, Line 1, Formula (19):

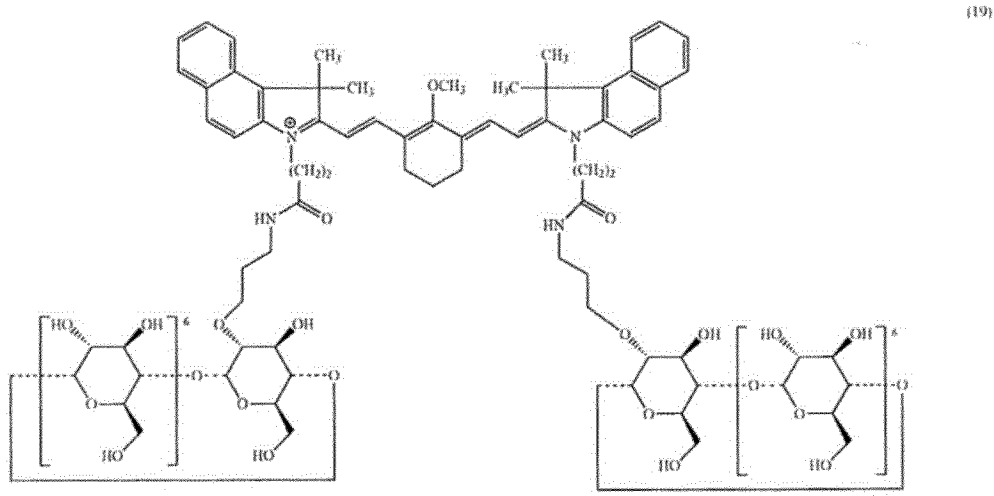

Should read:

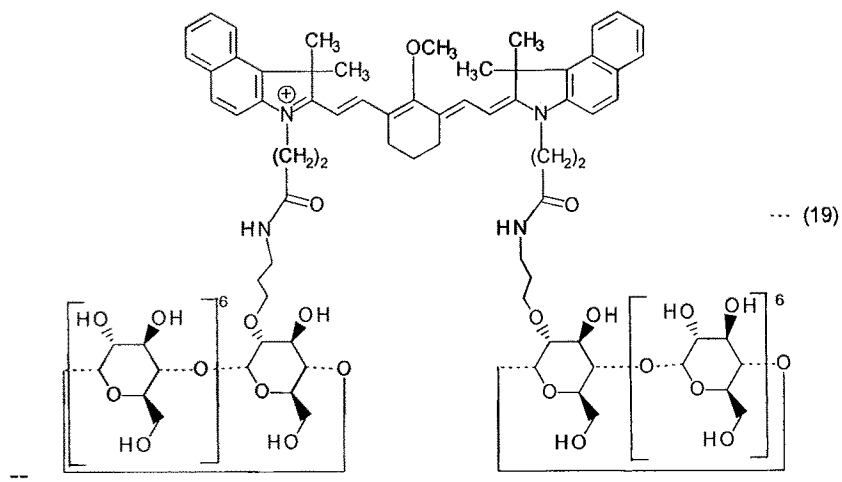

Columns 41 and 42, Formula (20):

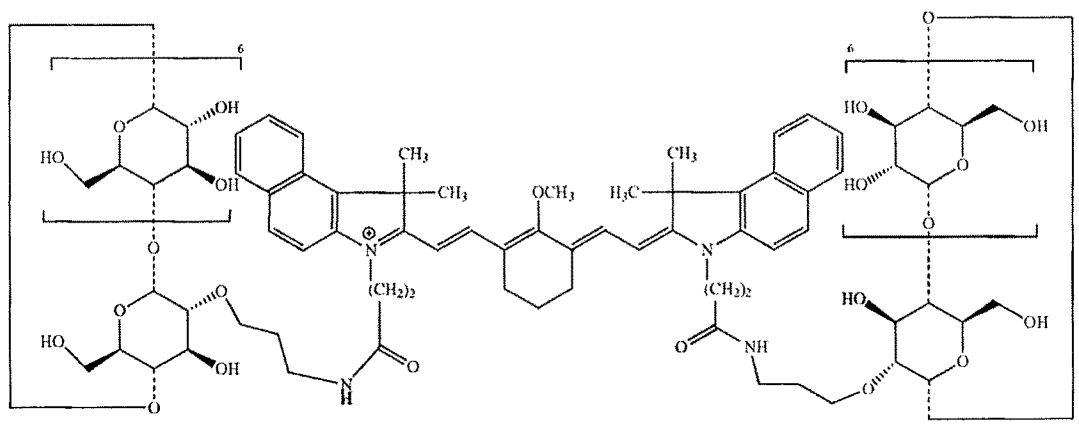

CERTIFICATE OF CORRECTION (continued)
U.S. Pat. No. 10,350,310 B2

Should read:

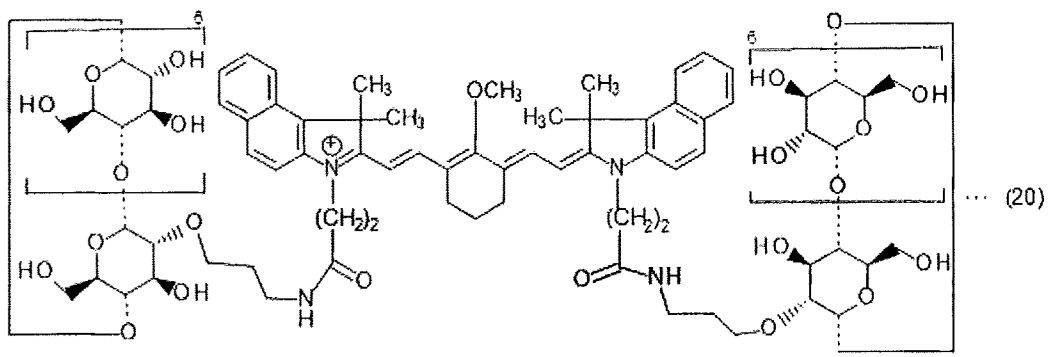
··· (20)

Columns 43 and 44, Line 1, Formula (21):

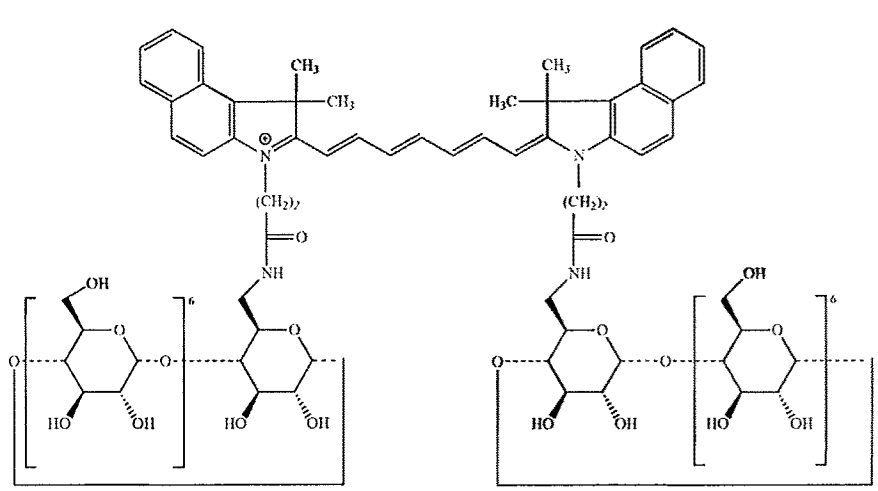
(21)

Should read:

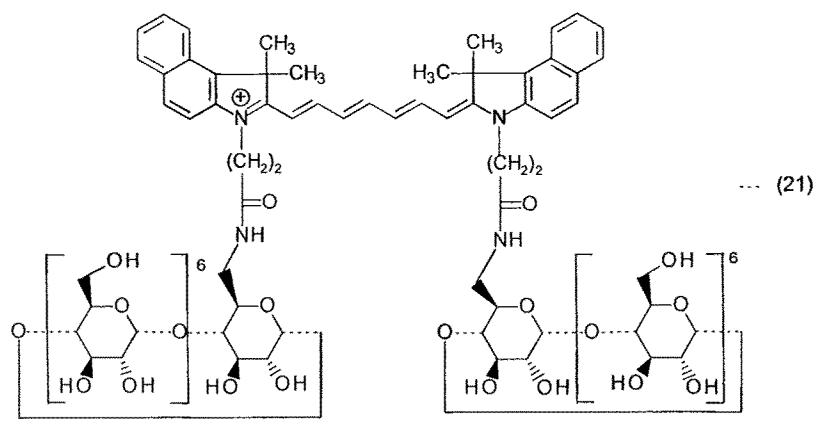
··· (21)

Columns 45 and 46, Line 1, Formula (23):
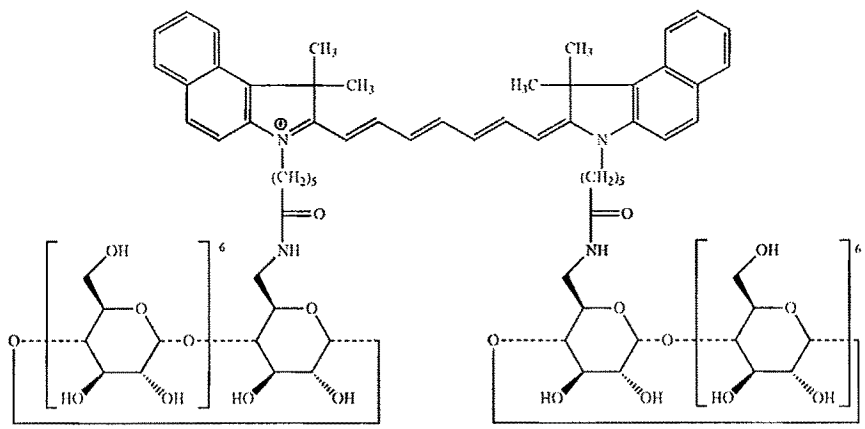
Should read:
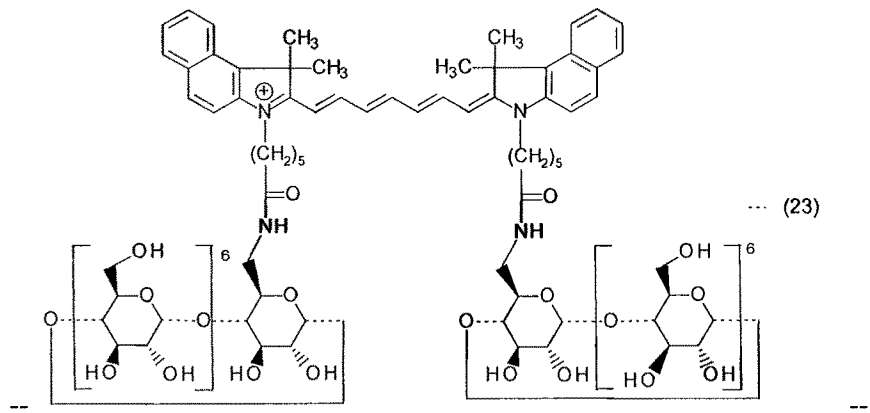
Columns 45 and 46, Line 34, Formula (24):
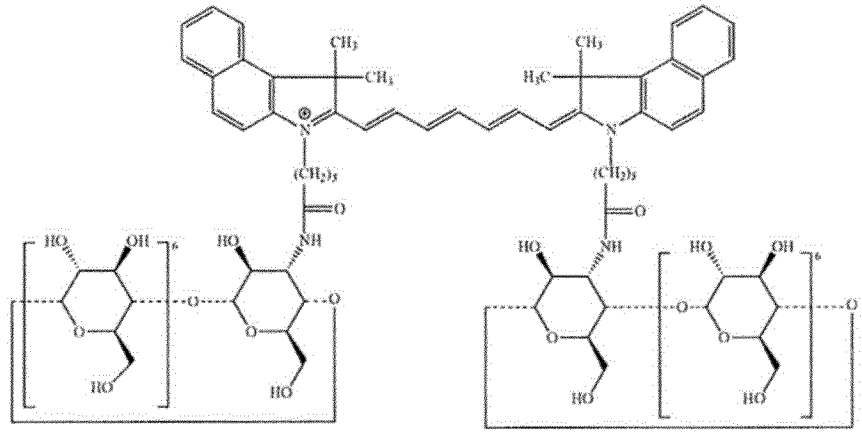

CERTIFICATE OF CORRECTION (continued)
U.S. Pat. No. 10,350,310 B2

Should read:

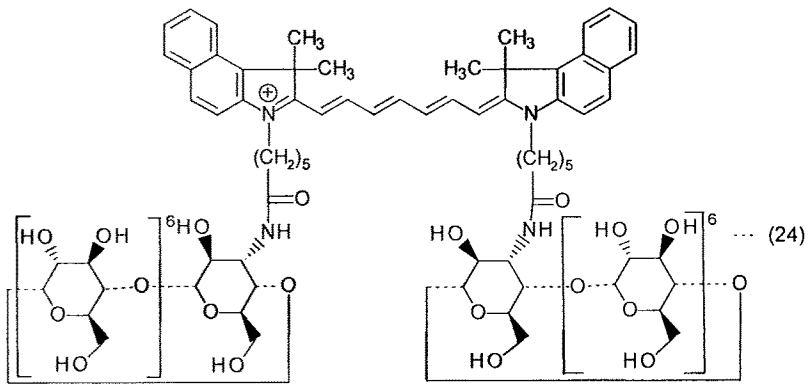

... (24)

Columns 47 and 48, Line 18, Formula (25):

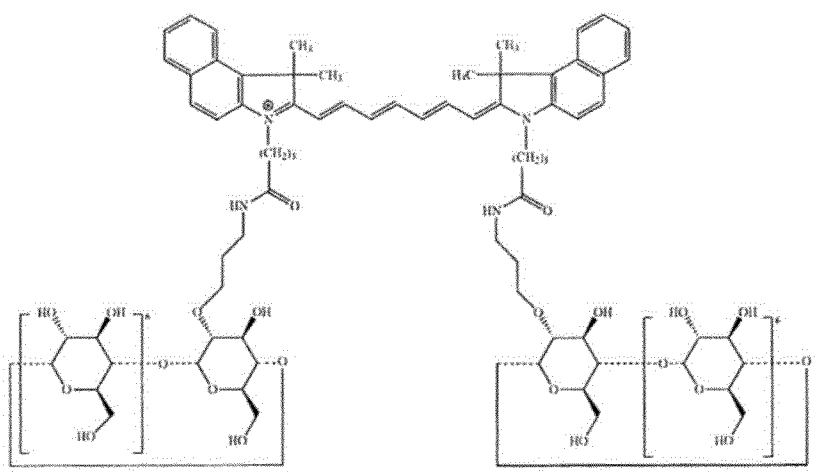

Should read:

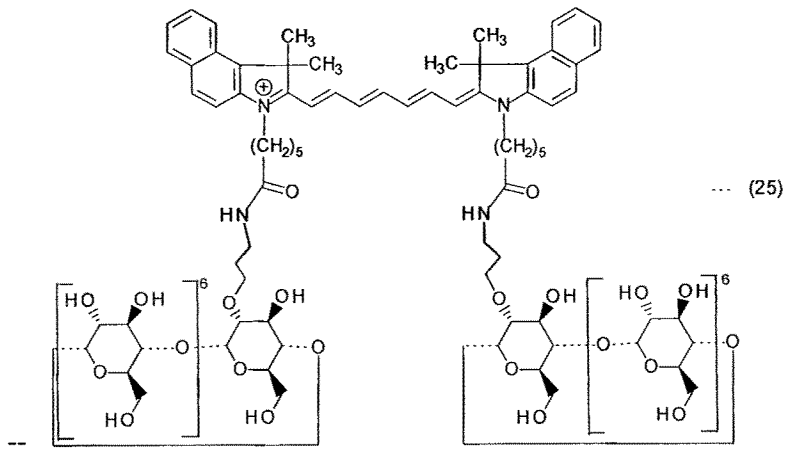

... (25)

CERTIFICATE OF CORRECTION (continued)
U.S. Pat. No. 10,350,310 B2

In the Claims

Column 56, Line 3, Formula (16):

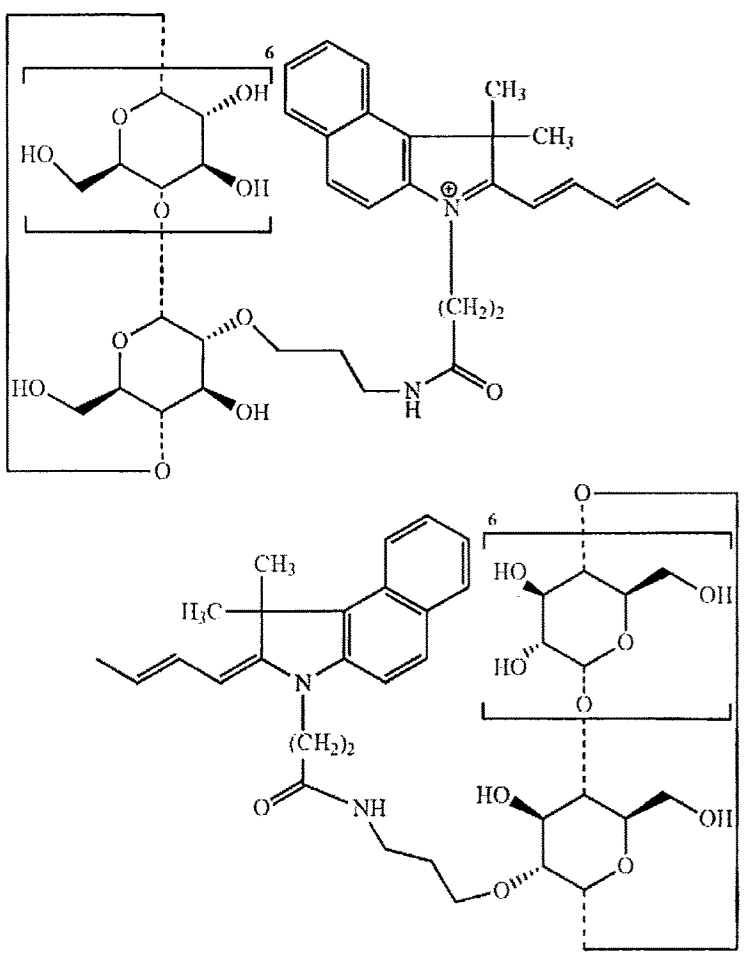

Should read as one formula: